US010596251B2

(12) United States Patent
Fattom et al.

(10) Patent No.: US 10,596,251 B2
(45) Date of Patent: *Mar. 24, 2020

(54) NANOEMULSION RESPIRATORY SYNCYTIAL VIRUS (RSV) SUBUNIT VACCINE

(71) Applicant: NanoBio Corporation, Ann Arbor, MI (US)

(72) Inventors: Ali I. Fattom, Ann Arbor, MI (US); Tarek Hamouda, Milan, MI (US); Vira Bitko, Ann Arbor, MI (US); James R. Baker, Jr., Ann Arbor, MI (US)

(73) Assignee: NanoBio Corporation, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/418,626

(22) Filed: Jan. 27, 2017

(65) Prior Publication Data
US 2017/0360919 A1 Dec. 21, 2017

Related U.S. Application Data

(63) Continuation of application No. 13/608,317, filed on Sep. 10, 2012, now Pat. No. 9,561,271.

(60) Provisional application No. 61/533,062, filed on Sep. 9, 2011.

(51) Int. Cl.
| A61K 39/155 | (2006.01) |
| A61K 39/12 | (2006.01) |
| A61K 47/10 | (2017.01) |
| A61K 47/18 | (2017.01) |
| A61K 47/26 | (2006.01) |
| A61K 9/107 | (2006.01) |
| A61K 47/44 | (2017.01) |
| A61K 39/00 | (2006.01) |

(52) U.S. Cl.
CPC .......... *A61K 39/155* (2013.01); *A61K 9/1075* (2013.01); *A61K 39/12* (2013.01); *A61K 47/10* (2013.01); *A61K 47/186* (2013.01); *A61K 47/26* (2013.01); *A61K 47/44* (2013.01); *A61K 2039/5252* (2013.01); *A61K 2039/543* (2013.01); *A61K 2039/55555* (2013.01); *A61K 2039/55566* (2013.01); *C12N 2760/18034* (2013.01)

(58) Field of Classification Search
None
See application file for complete search history.

(56) References Cited

U.S. PATENT DOCUMENTS

| 4,895,452 A | 1/1990 | Yiournas et al. |
| 5,103,497 A | 4/1992 | Hicks |
| 6,015,832 A | 1/2000 | Baker, Jr. et al. |
| 6,077,514 A | 6/2000 | Maassab et al. |
| 6,146,632 A | 11/2000 | Momin et al. |
| 6,372,227 B1 | 4/2002 | Garcon et al. |
| 6,451,325 B1 | 9/2002 | Van Nest et al. |
| 6,506,803 B1 | 1/2003 | Baker, Jr. et al. |
| 6,559,189 B2 | 5/2003 | Baker, Jr. et al. |
| 6,623,739 B1 | 9/2003 | Momin et al. |
| 6,635,676 B2 | 10/2003 | Baker, Jr. et al. |
| 6,867,000 B2 | 3/2005 | Mishkin et al. |
| 7,314,624 B2 * | 1/2008 | Baker ................. A01N 25/04 424/192.1 |
| 7,323,182 B2 | 1/2008 | Garcon et al. |
| 7,357,936 B1 | 4/2008 | Garcon |
| 7,731,967 B2 | 6/2010 | O'Hagan et al. |
| 8,226,965 B2 | 7/2012 | Baker, Jr. et al. |
| 9,492,525 B2 * | 11/2016 | Fattom ............. A61K 9/5115 |
| 9,561,271 B2 * | 2/2017 | Fattom ............. A61K 39/155 |
| 2004/0043041 A1 | 3/2004 | Baker, Jr. et al. |
| 2004/0151734 A1 | 8/2004 | Slaoui et al. |
| 2005/0208083 A1 | 9/2005 | Annis |
| 2006/0251684 A1 | 11/2006 | Annis et al. |
| 2007/0036831 A1 | 2/2007 | Baker |
| 2007/0054834 A1 | 3/2007 | Baker |
| 2008/0248057 A1 | 10/2008 | Cates et al. |
| 2008/0317799 A1 * | 12/2008 | Baker ................. A23L 33/135 424/405 |
| 2009/0269394 A1 | 10/2009 | Baker, Jr. et al. |
| 2010/0028433 A1 | 2/2010 | Baker et al. |
| 2010/0075914 A1 | 3/2010 | Flack et al. |
| 2010/0092526 A1 | 4/2010 | Baker, Jr. et al. |
| 2010/0226983 A1 | 9/2010 | Sutcliffe et al. |

(Continued)

FOREIGN PATENT DOCUMENTS

| WO | WO 98/43668 | 10/1998 |
| WO | WO 2011/148111 A1 | 6/2010 |

(Continued)

OTHER PUBLICATIONS

Herlocher et al. 1999 Vaccine vol. 17, pp. 172-181.*
Herlocher et al. 1999 Vaccine vol. 17, pp. 172-181 (Year: 1999).*
European Office Action issued in related European Patent Application No. 12735418.1, dated Jan. 25, 2017.
Office Action issued in related Japanese Patent Application No. 2014-519070, dated Mar. 21, 2017.
Notice of Reasons for Rejection issued in related Japanese Patent Application No. 2014-529937, dated Jun. 7, 2016.
Notice of Allowance issued in related U.S. Appl. No. 13/543,493, dated Jun. 27, 2016.
McGinnes, et al., "Assembly and Immunological Properties of Newcastle disease Virus-Like Particles Containing the Respiratory Syncytial Virus F and G Proteins," *Journ. of Viroglogy*, pp. 366-377 (2011).

(Continued)

*Primary Examiner* — Shanon A. Foley
*Assistant Examiner* — Myron G Hill
(74) *Attorney, Agent, or Firm* — Foley & Lardner LLP

(57) ABSTRACT

The present application relates to the field of immunology, in particular, a vaccine composition of respiratory syncytial virus (RSV) surface proteins, Fusion (F) and Glycoprotein (G) proteins subunit vaccine preferentially mixed with the immune cell targeting and enhancer, nanoemulsion to induce a protective immune response and avoid vaccine-induce disease enhancement.

19 Claims, 39 Drawing Sheets

Specification includes a Sequence Listing.

(56) References Cited

U.S. PATENT DOCUMENTS

| | | |
|---|---|---|
| 2010/0316673 A1 | 12/2010 | Lukacs et al. |
| 2011/0200657 A1 | 8/2011 | Baker |
| 2012/0064136 A1 | 3/2012 | Baker, Jr. et al. |
| 2012/0171249 A1 | 7/2012 | Annis et al. |

FOREIGN PATENT DOCUMENTS

| | | |
|---|---|---|
| WO | WO 2010/148111 A1 | 12/2010 |
| WO | WO 2013/006797 A1 | 1/2013 |

OTHER PUBLICATIONS

Passmore et al., "Intranasal immunization with $W_{80}5EC$ adjuvanted recombinant RSV rF-ptn enhances clearance of respiratory syncytial virus in a mouse model," *Human Vaccines & Immunotherapeutics*, vol. 10, No. 3, pp. 615-622 (2014).

European Search Report issued in related European Patent Application No. 12829559, dated Mar. 17, 2015.

Office Action issued in related U.S. Appl. No. 13/543,493, dated Jun. 4, 2015.

Office Action issued in related U.S. Appl. No. 15/543,493, dated Nov. 19, 2014.

Gomez et al., "Phase-I studay MEDI-534, of a live attenuated intranasal vaccine against respiratory syncytial virus and parainfluenza-3 virus seropositive children," *Ped Infect J.*, vol. 28, pp. 655-658 (2009).

Graham, B., "Biological challenges and technological opportunities for respiratory syncytial virus vaccine development,"*Immunological Reviews*, vol. 239, pp. 149-166 (2011).

Hacking et al., "Respiratory syncytial virus—virus biology and host response," *J. Infection.*, vol. 45 pp. 18-24 (2002).

Haung et al., "Recombinant respiratory syncytial virus F protein expression is hindered by inefficient nuclear export and mRNA processing," *Virus Genes*, vol. 40, pp. 212-221 (2010).

Kim et al.,"Single mucosal immunization of recombinant adenovirus-based vaccine expressing F1 protein fragment induces protective mucosal immunity against respiratory syncytial virus infection," *Vaccine*, vol. 28, pp. 3801-3808 (2010).

Kruijens et al., "Local innate and adaptive immune responses regulate inflammatory cell influx into the lungs after vaccination with formalin inactivated RSV," *Vaccine*, vol. 29, pp. 2730-2741 (2011).

Langley et al., "A dose ranging study of a subunit Respiratory Syncytial Virus subtype A vaccine with and without aluminum phosphate adjuvantation in adults ≥ 65 years of age," *Vaccine*, vol. 27, pp. 5913-5919 (2009).

Makidon et al., "Pre Clinical Evaluation of a Novel Nanoemulsion-Based Hepatitis B Mucosal Vaccine," *PLoS ONE*, vol. 3, No. 8, pp. 2954; 1-15 (2008).

McLellan et al., "Structure of the Respiratory Syncytial Virus Fusion glycoprotein in the post-fusion conformation reveals preservation of neutralizing epitopes," *J Virology*, pp. 7788-7796 (2011).

[Abstract] Boyoglu, S, Komal, Vo, et al. 2009. Enhanced delivery and expression of a nanoencapsulated DNA vaccine vector for respiratory sycytial virus. 5:463-472.

[Abstract] Castilow, E, Olson M, et al. 2007. Understanding respiratory syncytial (RSV) vaccine-enhanced disease. Immunol Res. 39:225-239.

[Abstract] Cyr, S, Jones, T et al. 2007. Intranasal proteosome-based respiratory syncytial virus (RSV) vaccine protect BALB/c mice against challenge without eosinophilla or enhanced pathology. Vaccine. 25:5378-5389.

[Abstract] Olszeska, W, Suezer, Y, et al. 2004. Protective and disease-enhancing immune responses induced by recombinant modified vaccinia Ankara (MVA) expressing respiratory syncytial virus protein. vaccine. 23:215-221.

Becker, Y. 2006. Respiratory syncytial virus (RSV) evades the human adaptive immunity system by skewing the Th1/Th2 cytokine balance toward increased levels of Th2 cytokines and IgE, markers of allergy—a review. Virus Genes. 33:235-252.

Bielinska, A, Gerber M, Blanco L, et al. Induction of Th17 cellular immunity with a novel nanoemulsion adjuvant. 2010. Crit Rev Immunol. 30:189-199.

Conti HR, Shen F, et al., Th17 and IL-17 receptor signaling are essential for mucosal host defenses against oral candidiasis. J Exp Med. 2009. 206:299-311.

DeLyrica E, Raymond WR, et al., Vaccination of mice with H pylori induces a strong Th-17 response and immunity that is neutrophil dependent. Gastroent. 2009. 136:247-256.

Fu, Y, He, J, et al. 2009. Intranasal Immunization with a replication0defucuebt adenoviral vector expressing the fusion glycoprotein of respiratory syncytial virus elicits protective immunity in BALB/c mice. Biochem & Biophys Res Comm. 381:528-532.

Hamouda T, Chepurnov A, Mank N, et al. Efficacy, immunogenicity and stability of a novel intranasal nanoemulsion adjuvanted influenza vaccine in a murine model. Hum Vaccine. 2010. 6:585-594.

Haynes, L, Caidi, H. et al. 2009. Therapeutic monoclonal antibody treatment targeting respiratory syncytial virus (RSV) G protein mediates viral clearance and reduces pathogenesis of RSV infection in BALB/c mice. J Infect Dis. 200:439-447.

International Search Report and Written Opinion issued in related International Patent Application No. PCT/US12/54395, dated Jan. 18, 2013.

Johnson, T, and Graham, B. 2004. Contribution of respiratory syncytial virus G antigenicity to vaccine-enhanced illness and the implication for severe disease during primary respiratory syncytial virus infection. Pediatr Infect Dis J. 23:46-57.

Johnson, T, Teng, M, et al. 2004. Respiratory syncytial virus (RSV) G glycoprotein is not necessary for vaccine-enhanced disease induced by immunization with formalin-inactivated RSV. J Virol. 78:6024-6032.

Lindell D, Morris S, White M, et al. A novel inactivated intranasal respiratory syncytial virus vaccine promotes viral clearance without Th2 associated vaccine-enhanced disease. PLoS One. 2011. 7e21823, 14 pages.

Lukacs et al., "Differential immune responses and pulmonary pathophysiology are induced by two different strains of respiratory syncytial virus," *Am J Pathol*, vol. 169, No. 3, pp. 977-986 (2006).

Lukacs, N, Smit J, et al. 2010, Respiratory virus-induced TLR7 activation controls IL-17-associated increased mucus via IL-23 regulation. J Immunol. 185:2231-2239.

Moore et al., "A Chimeric A2 Strain of Respiratory Syncytial Virus (RSV) with the Fusion Protein of RSV Strain Line 19 Exhibits Enhanced Viral Load, Mucus and Airway Dysfunction," *J. Virol.*, vol. 83, No. 9, pp. 4185-4194 (2009).

Munir, S, Hillyer, P, et al. 2011. Respiratory syncytial virus interferon antagonist NS1 protein suppresses and skews the human T lymphocyte response. PLoS Pathog 7(4): e1001336. Doi:10.1371/journal.ppat.1001.6, 17 pages.

Nallet et al., Respiratory Syncytial Virus subunit vaccine based on a recombinant fusion protein expressed transiently in mammalian cells, vol. 27, pp. 6415-6419 (2009).

Olson, M, Hartiwg, S, et al. 2011. The number of respiratory syncytial virus (RSV)-specific memory CD8 T cells in the lung is critical for their ability to inhibit RSV vaccine-enhanced pulmonary eosinophilia. J Immunol. 181-7958-7968.

Radu, G, Caidi, H. et al. 2010. Prophylactic treatment with a G glycoprotein monoclonal antibody reduces inflammatuion in a respiratory syncytial virus (RSV-G) challenge naive and formalin-inactivated RSV-immunized BALB/c mice. J Virol. 84:9632-9636.

Rixon, H., Brown, C. et al. 2002. Mulitple glycosylated forms of the respiratory syncytial virus fusion protein are expressed in virus-infected cells. J Gen Virology. 83: 61-66.

Schlender, J., Zimmer, G. 2003. Respiratory Syncytial Virus (RSV) fusion protein subunit F2, not attachment protein G, determines the specificity of RSV infection. J Virology. 77: 4609-4616.

Singh et al.,"Immuogenicity and efficacy of recombinant RSV-F vaccine in a mouse model," *Vaccine*, vol. 25, pp. 6211-6223 (2007).

(56) References Cited

OTHER PUBLICATIONS

Swanson et al., "Structural basis for immunization with potfusion respiratory syncytial virus fusion F glycoprotein (RSV F) to elicit high neutralizing antibody titers," *PNAS*, vol. 108, pp. 9619-9624 (2011).

Wu, H, Dennis, V, et al. 2009. RSV fusion (F) protein DNA vaccine provides protection against viral infection. Vaccine. 145:39-47.

Baker, "U-M Nanotechnology Institute collaborates in $6 million vaccine program," University of Michigan Nanotechnology Institute for Medicine and Biological Sciences (MNIMBS), Dec. 2, 2010, 2 pages.

Csaba, "Nanoparticles for Nasal Vaccination," *Adv. Drug Delivery Rev.*, vol. 61, No. 2, pp. 140-157 (Feb. 2009). [Abstract].

Kumar, et al., "Intranasal gene transfer by chitosan-DNA nanospheres protects BALB/c mice against acute respiratory syncytial virus infection," *Human Gene Therapy*, vol. 13, No. 12, pp. 1415-1425 (Aug. 2002). [Abstract].

Iqbal, et al., "Nasal delivery of chitosan-DNA plasmid expressing epitopes of respiratory syncytial virus (RSV) induces protective CTL responses in BALB/c mice," *Vaccine*, vol. 21, No. 13-14, pp. 1478-1485 (Mar. 2003). [Abstract].

Trudel, et al., "Experimental polyvalent ISCOMs subunit vaccine induces antibodies that neutralize human and bovine respiratory syncytial virus," *Vaccine*, vol. 7, No. 1, pp. 12-16 (Feb. 1989). [Abstract].

Hamouda, et al., "A novel surfactant nanoemulsion with a unique non-irritant topical antimicrobial activity against bacteria, enveloped viruses and fungi," Microbiol. Res., vol. 156, No. 1, pp. 1-7 (2001).

Office Action issued in co-pending European Patent Application No. 12735418, dated Sep. 14, 2018.

Kim, et al., "Intranasal vaccination with peptides and cholera toxin subunit F as adjuvant to enhance mucosal and systemic immunity to respiratory syncytial virus," *Arch Pharm. Res.*, vol. 30, No. 3, pp. 366-371 (2007).

Hancock, et al., "CpG containing oligodeoxynucleotides are potent adjuvants for parenteral vaccination with the fusion (F) protein of respiratory syncytial virus (RSV)," *Vaccine*, vol. 19, No. 32, pp. 4874-4882 (2001).

Hancock, et al., "QS-21 synergizes with recombinant interleukin-12 to create a potent adjuvant formulation for the fusion protein of respiratory syncytial virus," *Viral Immunol.* vol. 13, No. 4, pp. 503-509 (2000).

Hancock, et al., "Adjuvants recognized by toll-like receptors inhibit the induction of polarized type 2 T cell responses by natural attachment (G) protein of respiratory syncytial virus," *Vaccine*, vol. 21 (27-30), pp. 4348-4358 (Oct. 2003).

Passmore, et al., "Intranasal immunization with W805EC adjuvanted recombinant RSV rF-ptn enhances clearance of respiratory syncytial virus in a mouse model," *Human Vaccines & Immunotherapeutics*, vol. 10, No. 3, pp. 615-622 (Mar. 2014).

Extended Search Report issued in European Patent Application No. 18192928, dated Mar. 19, 2019.

* cited by examiner

IgG1

NE-F-RSV

RSV-PBS

F-RSV

*Histologic examination of Immunized and challenged mice*

10 μL sample was loaded in each lane.

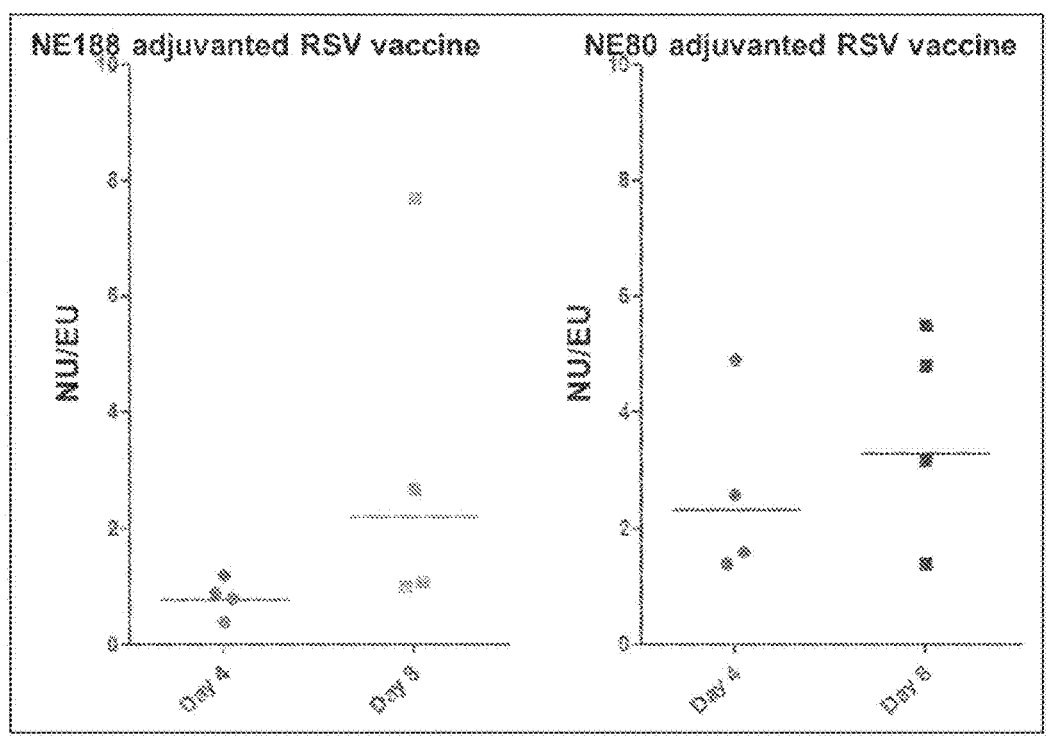

FIG. 25

```
                         SEQUENCE LISTING

<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccaaacaaac ccaataatga ttt                                             23

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcccagcagg ttggattgt                                                  19

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
catctagcaa atacaccatc ca                                              22
```

```
<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttctgcacat cataattagg agtatcaa                                              28

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aatgatatgc ctataacaaa tgatcagaa                                             29

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tggacatgat agagtaactt tgctgtct                                              28
```

NANOEMULSION RESPIRATORY SYNCYTIAL VIRUS (RSV) SUBUNIT VACCINE

CROSS REFERENCE TO RELATED APPLICATION

This application is a continuation of U.S. patent application Ser. No. 13/608,317, filed Sep. 10, 2012, which claims priority from U.S. Provisional Patent Application No. 61/533,062, filed Sep. 9, 2011, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 6, 2017, is named 038491-0274_SL.txt and is 1,740 bytes in size.

FIELD OF THE APPLICATION

The present application relates to the field of immunology, in particular, a nanoemulsion respiratory syncytial virus (RSV) vaccine composition comprising at least one RSV immunogen combined with a nanoemulsion adjuvant. The RSV immunogen can be any suitable RSV antigen, such as an RSV surface protein, Fusion (F) and Glycoprotein (G) proteins to form a subunit vaccine. The nanoemulsion RSV vaccine induces a protective immune response and avoids vaccine-induced disease enhancement.

BACKGROUND OF THE INVENTION

Respiratory Syncytial Virus (RSV) is a leading cause of serious respiratory disease in young children and the elderly worldwide and there is no vaccine available against this pathogen. Human respiratory syncytial virus (HRSV) is the most common etiological agent of acute lower respiratory tract disease in infants and can cause repeated infections throughout life. It is classified within the genus pneumovirus of the family paramyxoviridae. Like other members of the family, HRSV has two major surface glycoproteins (G and F) that play important roles in the initial stages of the infectious cycle. The G protein mediates attachment of the virus to cell surface receptors, while the F protein promotes fusion of the viral and cellular membranes, allowing entry of the virus ribonucleoprotein into the cell cytoplasm.

Respiratory syncytial virus (RSV) infection commonly results in bronchiolitis and is the leading cause for infant hospitalization in the developed countries. In addition, RSV is increasingly being described as a major pathogen in the elderly, transplant patients, and chronic obstructive pulmonary disease (COPD) patients (Hacking and Hull, 2002). The development of a safe and immunogenic vaccine to address the infant and elderly population presents a unique opportunity.

Previous methods of viral inactivation for vaccine formulation, such as formaldehyde, resulted in enhanced pulmonary disease and mortality. Extensive research into the development of viral vaccines to address RSV has met with limited success. Some of the major challenges for RSV vaccine development includes, early age of infection, evasion of innate immunity, failure of natural infection to induce immunity that prevent infection and the demonstration of vaccine-enhance illness coupled with problems associated with vaccine stability, purity, reproducibility and potency (Graham, 2011; Swanson and Settembre, 2011).

Approaches have included inactivation or viruses with formalin and the demonstration of vaccine-induced enhancement of diseases when infected with RSV. The observation that formalin inactivated vaccines have shown diseases-enhancement, included showing the skewed immune response that is important to prevent enhancement are essential for a protective immune response and having F protein its native state to maintain conformational epitopes is essential for the generation of neutralizing antibodies (Krujigen, 2011; Swanson 2011; McLellan et al., 2011). The demonstration that formalin-inactivated RSV vaccine diseases enhancement is not attributable to G protein and that G protein antibodies can reduce viral titers and actually protects against diseases enhancement suggests that G protein can be incorporated into a vaccine candidate (Radu et al, 2010; Haynes et al, 2009; Johnson et al, 2004). The use of live attenuated vaccines have met with limited success, as the vaccines have been shown to be minimally immunogenic (Gomez et al 2009). The utilization of a recombinant viral expressed F and G proteins vaccine showed reduced immunogenicity associated with low level of antigen expression, transient level of expression, cellular specificity and the demonstration that the purified F protein can be structurally immature and not the appropriate version for eliciting neutralizing antibodies (Singh and Dennis, 2007; Kim et al, 2010). With the use of subunit vaccine, having an optimal level of F protein is critical for inducing the appropriate immune response, as the subunit vaccines have been hindered by the inefficient and inappropriate expression of F and G proteins (Nallet et al., 2009; Huang and Lawlor 2010). The observation that subunit vaccine containing F protein, even with adjuvant is not completely protective and optimal (Langley et al., 2009), suggests that F protein presentation within its native state in the virion is essential for usage as a vaccine.

Prior teachings related to nanoemulsions are described in U.S. Pat. No. 6,015,832, which is directed to methods of inactivating Gram-positive bacteria, a bacterial spore, or Gram-negative bacteria. The methods comprise contacting the Gram-positive bacteria, bacterial spore, or Gram-negative bacteria with a bacteria-inactivating (or bacterial-spore inactivating) emulsion. U.S. Pat. No. 6,506,803 is directed to methods of killing or neutralizing microbial agents (e.g., bacterial, virus, spores, fungus, on or in humans using an emulsion. U.S. Pat. No. 6,559,189 is directed to methods for decontaminating a sample (human, animal, food, medical device, etc.) comprising contacting the sample with a nanoemulsion. The nanoemulsion, when contacted with bacteria, virus, fungi, protozoa or spores, kills or disables the pathogens. The antimicrobial nanoemulsion comprises a quaternary ammonium compound, one of ethanol/glycerol/PEG, and a surfactant. U.S. Pat. No. 6,635,676 is directed to two different compositions and methods of decontaminating samples by treating a sample with either of the compositions. Composition 1 comprises an emulsion that is antimicrobial against bacteria, virus, fungi, protozoa, and spores. The emulsions comprise an oil and a quaternary ammonium compound. U.S. Pat. No. 7,314,624 is directed to methods of inducing an immune response to an immunogen comprising treating a subject via a mucosal surface with a combination of an immunogen and a nanoemulsion. The nanoemulsion comprises oil, ethanol, a surfactant, a quaternary ammonium compound, and distilled water. US-2005-0208083 and US-2006-0251684 are directed to nanoemulsions having droplets with preferred sizes. US-2007-0054834 is directed to compositions comprising quaternary ammonium halides and methods of using the same to treat infectious conditions. The quaternary ammonium compound may be provided as part of an emulsion. US-2007-0036831 and US 2011-0200657 are directed to nanoemulsions comprising an anti-inflammatory agent. Other publications that describe nanoemulsions include U.S. Pat. No. 8,226,965 for "Methods of treating fungal, yeast and mold infections;" US 2009-0269394 for "Methods and compositions for treating onychomycosis;" US 2010-0075914 for "Methods for treating herpes virus infections;" US 2010-0092526 for "Nanoemulsion therapeutic compositions and methods of using the same;" US 2010-0226983 for "Compositions for treatment and prevention of acne, methods of making the compositions, and methods of use thereof," US 2012-0171249 for "Compositions for inactivating pathogenic microorganisms, methods of making the compositions, and methods of use thereof;" and US 2012-0064136 for "Anti-aging and wrinkle treatment methods using nanoemulsion compositions." However, none of these references teach the methods, compositions and kits of the present invention.

In particular, U.S. Pat. No. 7,314,624 describes nanoemulsion vaccines. However, this reference does not teach the ability to induce a protective immune response to RSV using the immunogen of the invention.

Prior art directed to vaccines includes, for example, U.S. Pat. No. 7,731,967 for "Composition for inducing immune response" (Novartis), which describes an antigen/adjuvant complex comprising at least two adjuvants. U.S. Pat. No. 7,357,936 for "Adjuvant systems and vaccines" (GSK) describes a combination of adjuvant and antigens. U.S. Pat. No. 7,323,182 for "Oil in water emulsion containing saponins" (GSK) describes a vaccine composition with an oil/water formulation. U.S. Pat. No. 6,867,000 for "Method of enhancing immune response to herpes" (Wyeth) describes a combination of viral antigens and cytokines (IL12). U.S. Pat. Nos. 6,623,739, 6,372,227, and 6,146,632, all for "Vaccines" (GSK), are directed to an immunogenic composition comprising an antigen and/or antigen composition and an adjuvant consisting of a metabolizable oil and alpha tocopherol in the form of an oil in water emulsion. U.S. Pat. No. 6,451,325 for "Adjuvant formulation comprising a submicron oil droplet emulsion" (Chiron) is directed to an adjuvant composition comprising a metabolizable oil, an emulsifying agent, and an antigenic substance, wherein the oil and emulsifying agent are present in the form of an oil-in-water emulsion. The adjuvant composition does not contain any polyoxypropylene-polyoxyethylene block copolymer; and the antigenic substance is not present in the internal phase of the adjuvant composition. Finally, US 20040151734 for "Vaccine and method of use" (GSK) describes a method of treating a female human subject suffering from or susceptible to one or more sexually transmitted diseases (STDs). The method comprises administering to a female subject in need thereof an effective amount of a vaccine formulation comprising one or more antigens derived from or associated with an STD-causing pathogen and an adjuvant.

There remains a need in the art for an effective RSV vaccine and methods of making and using the same. The present invention satisfies these needs.

SUMMARY OF THE INVENTION

The present invention provides a novel approach for delivering and inducing a protective immune response against RSV infection by combining at least one pivotal immunogenic viral surface antigen, e.g., F and G proteins, or antigenic fragments thereof, with a delivery and immune enhancing oil-in-water nanoemulsion. For example, the nanoemulsion RSV subunit vaccine of the invention induce a Th1 immune response, a Th2 immune response, a Th17 immune response, or any combination thereof.

The nanoemulsion RSV subunit vaccine comprises at least one RSV immunogen, which is RSV F protein, RSV G protein, an immunogenic fragment of RSV F protein, an immunogenic fragment of RSV G protein, or any combination thereof. Additionally, the nanoemulsion RSV subunit vaccine comprises droplets having an average diameter of less than about 1000 nm. The nanoemulsion present in the RSV subunit vaccine comprises: (a) an aqueous phase, (b) at least one oil, (c) at least one surfactant, (d) at least one organic solvent, and (e) optionally at least one chelating agent. Preferably the RSV immunogen is present in the nanoemulsion droplets. In another embodiment, the nanoemulsion RSV vaccine may be administered intranasally. In yet another embodiment of the invention, the nanoemulsion RSV vaccine lacks an organic solvent. Furthermore, additional adjuvants may be added to the nanoemulsion RSV vaccine.

In another embodiment of the invention, RSV virion particles are also present in the nanoemulsion RSV subunit vaccine. Preferably the RSV virion particles are present in the nanoemulsion droplets. The RSV virion particles can be inactivated by the nanoemulsion. In one embodiment, the RSV viral genome comprises at least one attenuating mutation.

The nanoemulsion RSV subunit vaccine may be formulated into any pharmaceutically acceptable dosage form, such as a liquid dispersion, gel, aerosol, pulmonary aerosol, nasal aerosol, ointment, cream, or solid dose.

The RSV surface antigen and/or RSV virion particles can be from any strain of RSV. In one embodiment, the RSV surface antigen and/or RSV virion particles are derived from respiratory syncytial virus (RSV) strain L19 (RSV-L19). In another embodiment, the RSV-L19 virus is a hyperproducer of Fusion (F) and Glycoprotein (G) structural proteins associated with viral particles. In yet another embodiment, the RSV-L19 virus is attenuated human respiratory syncytial virus (HRSV) strain L19. In one embodiment, the vaccine composition comprises a human respiratory syncytial virus deposited with the American Type Culture Collection (ATCC) as HRSV-L19.

In one embodiment, the RSV surface antigen further comprises at least one nucleotide modification denoting attenuating phenotypes. In another embodiment, the RSV surface antigen or an antigenic fragment thereof is present in a fusion protein. The RSV surface antigen can be a peptide fragment of RSV F protein, a peptide fragment of RSV G protein, or any combination thereof. Additionally, the RSV surface antigen can be multivalent.

In another embodiment of the invention, there is provided a method for preparing an immunogenic preparation, whereby the RSV strain, such as HRSV-L19, is genetically engineered with attenuating mutations and deletions resulting in an attenuating phenotype. The resulting attenuated RSV virus is cultured in an appropriate cell line and harvested. The harvested virus is then purified free from cellular and serum components. The purified virus is then mixed in an acceptable pharmaceutical carrier for use a vaccine composition. Thus, described are vaccine compositions comprising an RSV viral genome (such as RSV strain L19) comprising at least one attenuating mutation, preferably in combination with: F protein, G protein, antigenic fragments of F and/or G protein, or any combination thereof. In yet another embodiment, the vaccine compositions comprise an RSV viral genome (such as RSV strain L19) comprising nucleotide modifications denoting attenuating phenotypes.

In another embodiment of the invention, the vaccine composition is not systemically toxic to the subject, and produces minimal or no inflammation upon administration. In another embodiment, the subject undergoes seroconversion after a single administration of the vaccine.

In one embodiment, described is a method for enhancing immunity to human respiratory syncytial virus infections comprising administering to a subject a nanoemulsion formulation comprising RSV F and/or G protein and/or antigenic fragments thereof. Another embodiment of the invention is directed to a method for inducing an enhanced immunity against disease caused by human respiratory syncytial virus comprising the step of administering to a subject an effective amount of a vaccine composition according to the invention. In some embodiments, the subject can produce a protective immune response after at least a single administration of the nanoemulsion RSV vaccine. In addition, the immune response can be protective against one or more strains of RSV. The induction of enhanced immunity to HRSV is dependent upon the presence of optimal levels of antigen. Furthermore, the identification of the critical level of antigen is important for providing a robust immune response. The demonstration that RSV F protein levels are directly correlated with the presence and persistence of neutralizing antibodies and protection against viral challenge, demonstrates that having a viral strain that produces optimal levels of the critical immunogenic F protein expressed in its natural orientation is seminal for usage as a vaccine candidate.

In a further embodiment of the invention, RSV F and/or G protein, and/or antigenic fragments thereof, and/or RSV virion particles, are inactivated and adjuvanted with a nanoemulsion formulation to provide a non-infectious and immunogenic virus preparation. The simple mixing of a nanoemulsion with a vaccine candidate has been shown to produce both mucosal and systemic immune response. The mixing of the RSV virion particles with a nanoemulsion results in discrete antigen particles in the oil core of the droplet. The antigen is incorporated within the core and this allows it to be in a free form which promotes the normal antigen conformation.

The RSV vaccines may be formulated as a liquid dispersion, gel, aerosol, pulmonary aerosol, nasal aerosol, ointment, cream, or solid dose. In addition, the RSV vaccines may be administered via any pharmaceutically acceptable method, such as parenterally, orally, intranasally, or rectally. The parenteral administration can be by intradermal, subcutaneous, intraperitoneal or intramuscular injection.

In another embodiment of the invention, the nanoemulsion RSV vaccine composition comprises (a) at least one cationic surfactant and at least one non-cationic surfactant; (b) at least one cationic surfactant and at least one non-cationic surfactant, wherein the non-cationic surfactant is a nonionic surfactant; (c) at least one cationic surfactant and at least one non-cationic surfactant, wherein the non-cationic surfactant is a polysorbate nonionic surfactant, a poloxamer nonionic surfactant, or a combination thereof; (d) at least one cationic surfactant and at least one nonionic surfactant which is polysorbate 20, polysorbate 80, poloxamer 188, poloxamer 407, or a combination thereof; (e) at least one cationic surfactant and at least one nonionic surfactant which is polysorbate 20, polysorbate 80, poloxamer 188, poloxamer 407, or a combination thereof, and wherein the nonionic surfactant is present at about 0.01% to about 5.0%, or at about 0.1% to about 3%; (e) at least one cationic surfactant and at least one non-cationic surfactant, wherein the non-cationic surfactant is a nonionic surfactant, and the non-ionic surfactant is present in a concentration of about 0.05% to about 10%, about 0.05% to about 7.0%, about 0.1% to about 7%, or about 0.5% to about 4%; (f) at least one cationic surfactant and at least one a nonionic surfactant, wherein the cationic surfactant is present in a concentration of about 0.05% to about 2% or about 0.01% to about 2%; or (g) any combination thereof.

In yet another embodiment of the invention, the RSV vaccines comprise low molecular weight chitosan, medium molecular weight chitosan, high molecular weight chitosan, a glucan, or any combination thereof. The low molecular weight chitosan, median molecular weight chitosan, high molecular weight chitosan, a glucan, or any combination thereof can be present in the nanoemulsion.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

DESCRIPTION OF THE DRAWINGS

(FIG. 6A) depicts representative histology (Periodic Acid Schiff's, PAS; Hematoxylin and Eosin, H&E) from control RSV infected and NE+F-Protein vaccinated mice at day 8 post-infection. Eosinophils were not present. In (FIG. 6B), the expression of Muc5ac and Gob5 were assessed at day 8 post-infection via QPCR of lung RNA.

FIG. 10A shows histological examination of primary RSV infection; FIG. 10B shows histological examination of RSV-NE immunized animal; FIG. 10C shows histological examination of F protein immunized animal; and FIG. 10D shows histological examination of RSV+F protein immunized animal.

FIG. 22A shows the results for $W_{80}P_{188}5EC$ nanoemulsion combined with RSV strain L19, and FIG. 22B shows the results for $W_{80}5EC$ nanoemulsion combined with RSV strain L19. All cotton rats demonstrated high neutralizing antibodies (NU) against the vaccine RSV strain L19. Neutralizing antibodies were rising steadily following the challenge (Y axis). Day 8 neutralizing units (NU) were higher than Day 4 NU. Naïve Cotton Rats did not show any neutralization activity in their sera.

FIGS. 23A-23B: Shows the Specific activity of serum antibodies showed that the specific activity (Neutralizing units/ELISA units) of the serum antibodies tends to increase on Day 8 when compared to Day 4 post-challenge. FIG. 23A shows the results for $W_{80}P_{188}5EC$ nanoemulsion combined with RSV strain L19 (NU/EU for the Y axis), at Day 4 and Day 8. FIG. 23B shows the results for $W_{80}5EC$ nanoemulsion combined with RSV strain L19 (NU/EU for the Y axis), at Day 4 and Day 8.

FIG. 24A shows the results for $W_{80}P_{188}5EC$ nanoemulsion combined with RSV strain L19, and FIG. 24B shows the results for $W_{80}5EC$ nanoemulsion combined with RSV strain L19. Serum neutralization activity shows equivalent NU against RSV strain L19 or RSV strain A2, demonstrating cross protection between the two RSV strains.

FIG. 25: Shows viral clearance (RSV strain A2) at Day 4 in lungs of Cotton Rats. Vaccinated cotton rats (vaccinated with $W_{80}P_{188}5EC$ nanoemulsion combined with RSV strain L19, or W$_{80}$5EC nanoemulsion combined with RSV strain L19) showed complete clearance of RSV strain A2 challenged virus from the lungs of cotton rats. Naïve animals were showing >10$^3$ pfu RSV strain A2/gram of lung.

FIG. 28A shows the end point titers (Y axis) over a 14 week period, at day 4 post-challenge, and at day 8 post-challenge. FIG. 28B shows the ELISA units (Y axis) over a 14 week period, at day 4 post-challenge, and at day 8 post-challenge.

DESCRIPTION OF THE INVENTION

I. Overview

Figures 1A, 1B:
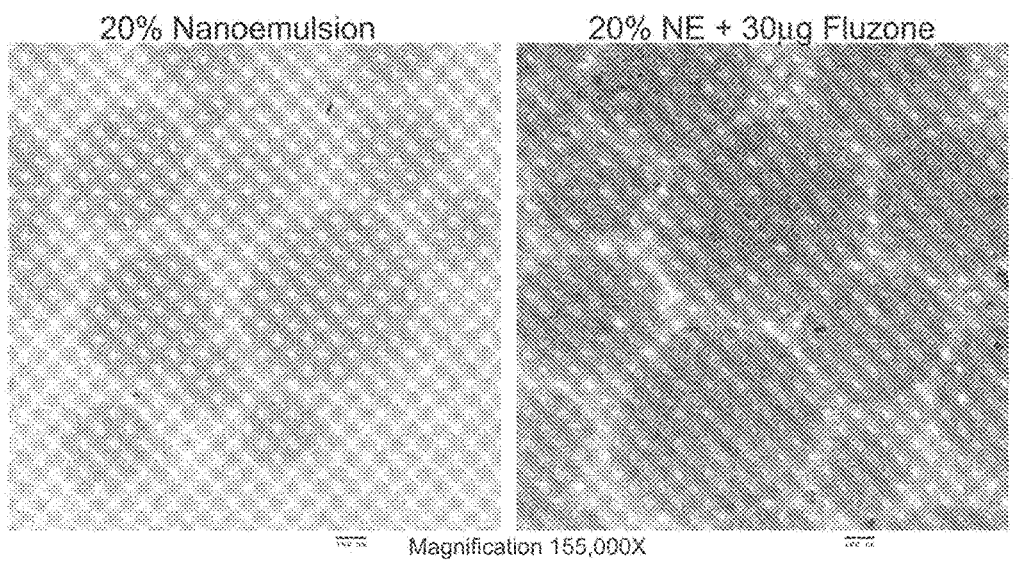
FIGS. 1A-1B: Shows TEMcross section images of the 20% $W_{80}5EC$ NE with and without 30 µg total HA (FIG. 1A). The panel on the right illustrates that the HA antigens are located in the oil droplets (FIG. 1B). The darkly stained antigens are located outside of the NE particles.

The present invention provides for the novel formulation of RSV surface antigens, F and G proteins mixed with nanoemulsion to address the inadequate immune response observed in previous data of RSV vaccines. An optimal vaccine against RSV would not only prevent against acute viral infection but also prevent against reinfections.

The nanoemulsion RSV subunit vaccine comprises at least one RSV immunogen, which is RSV F protein, RSV G protein, an immunogenic fragment of RSV F protein, an immunogenic fragment of RSV G protein, or any combination thereof. Additionally, the nanoemulsion RSV subunit vaccine comprises nanoemulsion droplets having an average diameter of less than about 1000 nm. Preferably the RSV immunogen is present in the nanoemulsion droplets. In another embodiment of the invention, RSV virion particles are also present in the nanoemulsion RSV subunit vaccine. Preferably the RSV virion particles are present in the nanoemulsion droplets.

The present invention provides a novel approach for delivering and inducing a protective immune response against RSV infection by combining a pivotal immunogenic RSV viral surface antigen, F and/or G proteins, with a delivery and immune enhancing oil-in-water nanoemulsion. Utilization of isolated RSV viral surface antigens shown to be the major viral immunogens independent from other viral components, such as viral protein NS1, which can skew the immune response resulting in enhanced disease, is an important foundation for a subunit vaccine. Further, mixing one or more of the RSV surface antigens with a nanoemulsion, which preferentially encloses the antigens and acts as a delivery system to the appropriate immune cells and additionally as a potent immune enhancing component, underscores the novelty of the present invention. Compared to other subunit vaccines and recombinant vaccines with results lacking for a fully functional human vaccine, the nanoemulsion RSV subunit viral surface antigens provide significant novelty compared to previous candidates in its ability to generate a robust, sustainable and protective immune response.

The induction of enhanced immunity to RSV is dependent upon the presence and presentation of an optimal level of antigens. Combining isolated RSV surface antigens with a nanoemulsion provides a novel approach to deliver the vaccine to appropriate antigen presenting cells of the immune response.

The nanoemulsion compositions of the invention function as a vaccine adjuvant. Adjuvants serve to: (1) bring the antigen—the substance that stimulates the specific protective immune response—into contact with the immune system and influence the type of immunity produced, as well as the quality of the immune response (magnitude or duration); (2) decrease the toxicity of certain antigens; (3) reduce the amount of antigen needed for a protective response; (4) reduce the number of doses required for protection; (5) enhance immunity in poorly responding subsets of the population and/or (7) provide solubility to some vaccines components.

In one embodiment, multivalent subunit vaccine can be constructed utilizing surface antigens F and G proteins derived from RSV and mixed with nanoemulsion.

In another embodiment, derivatives and fusions proteins can be designed from the RSV surface antigens F and G proteins and are then mixed with nanoemulsion to generate a subunit vaccine.

In one embodiment, subunit vaccines can be constructed with one or more of RSV surface antigens, namely F and G proteins mixed with a nanoemulsion. It is entirely possible to have both F and G proteins added together and mixed with a nanoemulsion in a resulting subunit vaccine composition. In another embodiment, either F or G protein mixed with a nanoemulsion is a suitable subunit vaccine according to the invention. Antigenic fragments of F and/or G protein can also be utilized in the nanoemulsion RSV vaccines of the invention.

Nanoemulsions are oil-in-water emulsions composed of nanometer sized droplets with surfactant(s) at the oil-water interface. Because of their size, the nanoemulsion droplets are pinocytosed by dendritic cells triggering cell maturation and efficient antigen presentation to the immune system. When mixed with different antigens, nanoemulsion adjuvants elicit and up-modulate strong humoral and cellular $T_H1$-type responses as well as mucosal immunity (Makidon et al., "Pre-Clinical Evaluation of a Novel Nanoemulsion-Based Hepatitis B Mucosal Vaccine," PLoS ONE. 3(8): 2954; 1-15 (2008); Hamouda et al., "A Novel Nanoemulsion Adjuvant Enhancing The Immune Response from Intranasal Influenza Vaccine in Mice in National Foundation for Infectious Disease," 11th Annual Conference on Vaccine Research. Baltimore, Md. (2008); Myc et al., "Development of immune response that protects mice from viral pneumonitis after a single intranasal immunization with influenza A virus and nanoemulsion," Vaccine, 21(25-26):3801-14 (2003); Bielinska et al., "Mucosal Immunization with a Novel Nanoemulsion-Based Recombinant Anthrax Protective Antigen Vaccine Protects against Bacillus anthracis Spore Challenge," Infect Immun., 75(8): 4020-9 (2007); Bielinska et al., "Nasal Immunization with a Recombinant HIV gp120 and Nanoemulsion Adjuvant Produces Th1 Polarized Responses and Neutralizing Antibodies to Primary HIV Type 1 Isolates," AIDS Research and Human Retroviruses, 24(2): 271-81 (2008); Bielinska et al., "A Novel, Killed-Virus Nasal Vaccinia Virus Vaccine," Clin. Vaccine immunol., 15(2): 348-58 (2008); Warren et al., "Pharmacological and Toxicological Studies on Cetylpyridinium Chloride, A New Germicide," J. Pharmacol. Exp. Ther., 74:401-8 (1942)). Examples of such antigens include protective antigen (PA) of anthrax (Bielinska et al., Infect. Immun., 75(8): 4020-9 (2007)), whole vaccinia virus (Bielinska et al., Clin. Vaccine Immunol., 15(2): 348-58 (2008)) or gp120 protein of Human Immune Deficiency Virus (Bielinska et al., AIDS Research and Human Retroviruses. 24(2): 271-81 (2008)). These studies demonstrate the broad application of the nanoemulsion adjuvant with a variety of antigens including RSV antigens.

In one embodiment of the invention, the nanoemulsion RSV vaccine comprises droplets having an average diameter of less than about 1000 nm and: (a) an aqueous phase; (b) about 1% oil to about 80% oil; (c) about 0.1% to about 50% organic solvent; (d) about 0.001% to about 10% of a surfactant or detergent; or (e) any combination thereof. In another embodiment of the invention, the nanoemulsion vaccine comprises: (a) an aqueous phase; (b) about 1% oil to about 80% oil; (c) about 0.1% to about 50% organic solvent; (d) about 0.001% to about 10% of a surfactant or detergent; and (e) F and G surface antigens of RSV or immunogenic fragments thereof. In another embodiment of the invention, the nanoemulsion lacks an organic solvent.

The quantities of each component present in the nanoemulsion and/or nanoemulsion vaccine refer to a therapeutic nanoemulsion and/or nanoemulsion RSV vaccine.

The methods comprise administering to a subject a nanoemulsion RSV vaccine, wherein the nanoemulsion vaccine comprises droplets having an average diameter of less than about 1000 nm. In an exemplary embodiment of the invention, the nanoemulsion RSV vaccine further comprises (a) an aqueous phase, (b) at least one oil, (c) at least one surfactant, (d) at least one organic solvent, (e) RSV surface antigens, F and G proteins, and (f) optionally comprising at least one chelating agent, or any combination thereof. In another embodiment of the invention, the nanoemulsion lacks an organic solvent.

In one embodiment, the subject is selected from adults, elderly subjects, juvenile subjects, infants, high risk subjects, pregnant women, and immunocompromised subjects. In another embodiment, the nanoemulsion RSV vaccine may be administered intranasally.

The nanoemulsion RSV subunit vaccine composition can be delivered via any pharmaceutically acceptable route, such as by intranasal route of other mucosal routes. Other exemplary pharmaceutically acceptable methods include intranasal, buccal, sublingual, oral, rectal, ocular, parenteral (intravenously, intradermally, intramuscularly, subcutaneously, intracistemally, intraperitoneally), pulmonary, intravaginal, locally administered, topically administered, topically administered after scarification, mucosally administered, via an aerosol, or via a buccal or nasal spray formulation. Further, the nanoemulsion RSV vaccine can be formulated into any pharmaceutically acceptable dosage form, such as a liquid dispersion, gel, aerosol, pulmonary aerosol, nasal aerosol, ointment, cream, semi-solid dosage form, or a suspension. Further, the nanoemulsion RSV vaccine may be a controlled release formulation, sustained release formulation, immediate release formulation, or any combination thereof. Further, the nanoemulsion RSV vaccine may be a transdermal delivery system such as a patch or administered by a pressurized or pneumatic device (i.e., a "gene gun").

A. RSV Strain L19

In one embodiment of the invention, the RSV strain utilized in the nanoemulsion RSV vaccine is RSV Strain L19. Additionally, the F and/or G protein, or antigenic fragment thereof, utilized in the nanoemulsion RSV strain can be from RSV Strain L19.

It was surprisingly discovered that cells infected with RSV L19 virus produce between 3-11 fold higher quantities of RSV viral proteins as compared to cells infected with RSV A2 virus (see Example 6, infra.). In one embodiment of the invention, the RSV antigen present in the vaccines of the invention is RSV L19 virus, and more preferably human RSV L19 virus, including the purified, attenuated human respiratory syncytial virus (HRSV) strain L19 (HRSV-L19). In yet other embodiments of the invention, the RSV viral genome can comprise at least one attenuating mutation, including but not limited to nucleotide modifications denoting attenuating phenotypes. Additionally, the nanoemulsion RSV vaccine of the invention can comprise F or G protein, or antigenic fragments thereof, from RSV L19 virus.

RSV L19 strain was found to cause infection and enhanced respiratory disease (ERD) in mice. Moreover, data published showed that it conferred protection without induction of ERD in mice when formulated with nanoemulsion.

The RSV Strain L19 isolate was isolated from an RSV-infected infant with respiratory illness in Ann Arbor, Mich. on 3 Jan. 1967 in WI-38 cells and passaged in SPAFAS primary chick kidney cells followed by passage in SPAFAS primary chick lung cells prior to transfer to MRC-5 cells (Herlocher 1999) and subsequently Hep2 cells (Lukacs 2006). Comparison of RSV L19 genome (15,191-nt; GenBank accession number FJ614813) with the RSV strain A2 (15,222-nt; GenBank accession number M74568) shows that 98% of the genomes are identical. Most coding differences between L19 and A2 are in the F and G genes. Amino acid alignment of the two strains showed that F protein has 14 (97% identical) and G protein has 20 (93% identical) amino acid differences.

RSV L19 strain has been demonstrated in animal models to mimic human infection by stimulating mucus production and significant induction of IL-13 using an inoculum of $1\times10^5$ plaque forming units (PFU)/mouse by intra-tracheal administration (Lukacs 2006).

Importantly and uniquely, the RSV L19 viral strain is unique in that it produces significantly higher yields of F protein (approximately 10-30 fold more per PFU) than the other strains. F protein content may be a key factor in immunogenicity and the L19 strain currently elicits the most robust immune response. The L19 strain has a shorter propagation time and therefore will be more efficient from a manufacturing perspective.

Most significantly, nanoemulsion-inactivated and adjuvanted RSV L19 vaccines are highly immunogenic in the universally accepted cotton rat model. Cotton rats elicited a rise in antibody titers after one immunization and a significant boost after the second immunization (approximately a 10-fold increase). The antibodies generated are highly effective in neutralizing live virus and there is a linear relationship between neutralization and antibody titers. Furthermore, antibodies generated in cotton rats showed cross protection when immunized with the RSV L19 strain and challenged with the RSV A2 strain. Both IM and IN immunization established memory that can be invoked or recalled after an exposure to antigen either as a second boost or exposure to live virus.

In another embodiment of the invention, the RSV vaccines of the invention are cross-reactive against at least one other RSV strain not present in the vaccine (or cross-reactive against one or more RSV strains). As it is known to one of ordinary skill in the art, cross reactivity can be measured 1) using ELISA method to see if the sera from vaccinated animals or individuals will produce antibodies against strains that were not used in the administered vaccine; 2) Immune cells will produce cytokines when stimulated in vitro using stains that were not used in the administered vaccine. Cross protection can be measured in vitro when antibodies in sera of animals vaccinated with one strain will neutralize infectivity of another virus not used in the administered vaccine.

II. Definitions

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The term "antigenic fragment" of an RSV surface antigen preferably refers to a peptide having at least about 5 consecutive amino acids of a naturally occurring or mutant RSV F protein or RSV G protein. The antigenic fragment can be any suitable length, such as between about 5 amino acids in length up to and including the full length of the F or G protein. The F protein is about 518 amino acids in length, and the G protein is about 242 amino acids in length. For example, the antigenic fragment can also be about 10, about 15, about 20, about 30, about 40, about 50, about 60, about 70, about 80, about 90, about 100, about 110, etc up to about 242 amino acids in length for a G protein antigenic fragment, and up to about 518 amino acids in length for an F protein antigenic fragment.

The term "nanoemulsion," as used herein, includes small oil-in-water dispersions or droplets, as well as other lipid structures which can form as a result of hydrophobic forces which drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. The present invention contemplates that one skilled in the art will appreciate this distinction when necessary for understanding the specific embodiments herein disclosed.

As used herein, the term "antigen" refers to proteins, polypeptides, glycoproteins or derivatives or fragment that can contain one or more epitopes (linear, conformation, sequential, T-cell) which can elicit an immune response. Antigens can be separated in isolated viral proteins or peptide derivatives.

As used herein, the term "F protein" refers to a polypeptide or protein having all or partial amino acid sequence of an RSV Fusion protein. As used herein, F protein includes either F1, F2 or both components of the RSV Fusion protein/polypeptide.

As used herein, the term "G protein" refers to a polypeptide or protein having all or partial amino acid sequence of RSV G attachment protein/polypeptide.

As used herein, the term "isolated" refers to proteins, glycoproteins, peptide derivatives or fragment or polynucleotide that is independent from its natural location. Viral components that are independently obtained through recombinant genetics means typically leads to products that are relatively purified.

As used herein, the term "adjuvant" refers to an agent that increases the immune response to an antigen (e.g., RSV surface antigens). A used herein, the term "immune response" refers to a subject's (e.g., a human or another animal) response by the immune system to immunogens (i.e., antigens) the subject's immune system recognizes as foreign. Immune responses include both cell-mediated immune responses (responses mediated by antigen-specific T cells and non-specific cells of the immune system—Th1, Th2, Th17) and humoral immune responses (responses mediated by antibodies). The term "immune response" encompasses both the initial "innate immune responses" to an immunogen (e.g., RSV surface antigens) as well as memory responses that are a result of "acquired immunity."

As used herein, the term "RSV surface antigens" refers to proteins, glycoproteins and peptide fragments derived from the envelope of RSV viruses. Preferred RSV surface antigens are F and G proteins. The RSV surface antigens are generally extracted from viral isolates from infected cell cultures, or produced by synthetically or using recombinant DNA methods. The RSV surface antigens can be modified by chemical, genetic or enzymatic means resulting in fusion proteins, peptides, or fragments.

As used herein, the term "immunogen" refers to an antigen that is capable of eliciting an immune response in a subject. In preferred embodiments, immunogens elicit immunity against the immunogen (e.g., a pathogen or a pathogen product) when administered in combination with a nanoemulsion of the present invention.

As used herein, the term "enhanced immunity" refers to an increase in the level of acquired immunity to a given pathogen following administration of a vaccine of the present invention relative to the level of acquired immunity when a vaccine of the present invention has not been administered.

As used herein, the term "virion" refers to isolated, matured respiratory syncytial virus particles obtained from infected mammalian cell culture. As used herein, virion can refer to either RSV-1 or RSV-viral particles.

As used herein, the term "multivalent vaccines" refers to a vaccine comprising more than one antigenic determinant of a single viral agent or multiples strains. As used herein, multivalent vaccine comprise multiple RSV viral surface antigens, F, F1, F2 and G proteins. Multivalent vaccines could be constructed with antigens derived from both RSV-1 and RSV-2.

As used herein, the term "inactivated" RSV refers to virion particles that are incapable of infecting host cells and are noninfectious in pertinent animal models.

As used herein, the term "subunit" refers to isolated and generally purified RSV glycoproteins that are individually or mixed further with nanoemulsion comprising a vaccine composition. The subunit vaccine composition is free from mature virions, cells or lysate of cell or virions. The method of obtaining a viral surface antigen that is included in a subunit vaccine can be conducted using standard recombinant genetics techniques and synthetic methods and with standard purification protocols.

III. Characteristics of the Nanoemulsion RSV Vaccines

A. Stability

The nanoemulsion RSV vaccines of the invention can be stable at about 40° C. and about 75% relative humidity for a time period of at least up to about 2 days, at least up to about 2 weeks, at least up to about 1 month, at least up to about 3 months, at least up to about 6 months, at least up to about 12 months, at least up to about 18 months, at least up to about 2 years, at least up to about 2.5 years, or at least up to about 3 years.

In another embodiment of the invention, the nanoemulsion RSV vaccines of the invention can be stable at about 25° C. and about 60% relative humidity for a time period of at least up least up to about 2 days, at least up to about 2 weeks, to about 1 month, at least up to about 3 months, at least up to about 6 months, at least up to about 12 months, at least up to about 18 months, at least up to about 2 years, at least up to about 2.5 years, or at least up to about 3 years, at least up to about 3.5 years, at least up to about 4 years, at least up to about 4.5 years, or at least up to about 5 years.

Further, the nanoemulsion RSV vaccines of the invention can be stable at about 4° C. for a time period of at least up to about 1 month, at least up to about 3 months, at least up to about 6 months, at least up to about 12 months, at least up to about 18 months, at least up to about 2 years, at least up to about 2.5 years, at least up to about 3 years, at least up to about 3.5 years, at least up to about 4 years, at least up to about 4.5 years, at least up to about 5 years, at least up to about 5.5 years, at least up to about 6 years, at least up to about 6.5 years, or at least up to about 7 years.

The nanoemulsion RSV vaccines of the invention can be stable at about −20° C. for a time period of at least up to about 1 month, at least up to about 3 months, at least up to about 6 months, at least up to about 12 months, at least up to about 18 months, at least up to about 2 years, at least up to about 2.5 years, at least up to about 3 years, at least up to about 3.5 years, at least up to about 4 years, at least up to about 4.5 years, at least up to about 5 years, at least up to about 5.5 years, at least up to about 6 years, at least up to about 6.5 years, or at least up to about 7 years.

These stability parameters are also applicable to nanoemulsion adjuvants and/or nanoemulsion RSV vaccines.

B. Immune Response

The immune response of the subject can be measured by determining the titer and/or presence of antibodies against the RSV immunogen after administration of the nanoemulsion RSV vaccine to evaluate the humoral response to the immunogen. Seroconversion refers to the development of specific antibodies to an immunogen and may be used to evaluate the presence of a protective immune response. Such antibody-based detection is often measured using Western blotting or enzyme-linked immunosorbent (ELISA) assays or hemagglutination inhibition assays (HAI). Persons of skill in the art would readily select and use appropriate detection methods.

Another method for determining the subject's immune response is to determine the cellular immune response, such as through immunogen-specific cell responses, such as cytotoxic T lymphocytes, or immunogen-specific lymphocyte proliferation assay. Additionally, challenge by the pathogen may be used to determine the immune response, either in the subject, or, more likely, in an animal model. A person of skill in the art would be well versed in the methods of determining the immune response of a subject and the invention is not limited to any particular method.

Experiments conducted during the course of the development of the current invention, demonstrated that nanoemulsion added to hepatitis B surface antigen (HBsAg) and administered intranasally was safe and effective hepatitis B vaccine. The mucosal vaccine induced a Th1 associated cellular immune response, with concomitant neutralizing antibodies production. A single nasal immunization of the HBsAg nanoemulsion mixture produces a rapid induction of serum antibodies that was comparable to currently administered intramuscular vaccines. Further, there was demonstration of affinity maturation in the antibody response, which is predictive of the potential efficacy of vaccine (Makidon et al., 2008).

Most significantly, as detailed in the examples below, all RSV vaccines formulated in a nanoemulsion and administered intranasally (IN) or intramuscularly (IM) elicited a protective immune response that prevented infection of immunized animals. Moreover, nanoemulsion-inactivated and adjuvanted RSV vaccines are highly immunogenic in the universally accepted cotton rat model. Cotton rats elicited a rise in antibody titers after one immunization and a significant boost after the second immunization (approximately a 10-fold increase). The antibodies generated are highly effective in neutralizing live virus and there is a linear relationship between neutralization and antibody titers. Furthermore, antibodies generated in cotton rats showed cross protection when immunized with the RSV L19 strain and challenged with the RSV A2 strain. Both IM and IN immunization established memory that can be invoked or recalled after an exposure to antigen either as a second boost or exposure to live virus.

Another emerging component of vaccine protective efficacy is the induction of T-helper-17 (Th17) cytokine responses. The demonstration that IL-17 contributes to the normal immune response to pathogens, has been further utilized to show relevance in vaccination strategies (DeLyrica et al. 2009; Conti et al., 2009). In the development of the current invention, mucosal immunization with nanoemulsion can product adjuvant effects in activating Th1 and Th17 immunity. Mucosal immunization with nanoemulsion resulted in activation of innate immune which directly helps in the induction of Th1 and Th17 cells. The results further clarify the immune enhancing features of nanoemulsion importance in the field of vaccination for the induction of cellular immunity against inactivated RSV virions (Bielinska et al., 2010; Lindell et al, 2011).

C. Virus Inactivation

Vaccines need to comprise inactivated virus, particularly when the vaccine comprises whole virus, e.g., to ensure that the vaccine does not cause the disease it is treating and/or preventing. In other words, inactivation of virus ensures that the vaccine does not comprise infectious particles. Approaches have included inactivation of viruses with formalin. However, formalin-inactivated vaccines have shown disease-enhancement, including showing a skewed immune response that is important to prevent disease-enhancement, and priming by mature dendritic cells, which are essential for a protective immune response. The use of live attenuated vaccines has met with limited success, as the vaccines have been shown to be minimally immunogenic.

In the methods and compositions of the invention, the nanoemulsion functions to inactivate and adjuvant the whole virus and/or viral antigens to provide a non-infectious and immunogenic virus. Alternatively, the virus (whole or antigens) can be inactivated prior to combining with the nanoemulsion. Examples of chemical methods of viral inactivation include, but are not limited to, formalin or β-propiolactone (β-PL), physical methods of viral inactivation include using heat or irradiation, or by molecular genetics means to produce a non-infectious particles. The simple mixing of a nanoemulsion with a vaccine candidate has been shown to produce both mucosal and system immune response. The mixing of the RSV virion particles with a nanoemulsion results in discrete antigen particles in the oil core of the droplet. The antigen is incorporated within the core and this allows it to be in a free form which promotes the normal antigen conformation.

IV. Nanoemulsion RSV Vaccines

A. RSV Immunogen

The RSV immunogen present in the nanoemulsion RSV vaccines of the invention is an RSV surface antigen, such as F protein, G protein, and/or antigenic fragments thereof. The F protein, G protein and antigenic fragments thereof can be obtained from any known RSV strain. Additionally, the RSV vaccine can comprise whole RSV virus, including native, recombinant, and mutant strains of RSV, which is combined with the one or more RSV antigens. In one embodiment of the invention, the RSV virus can be resistant to one or more antiviral drugs, such as resistant to acyclovir. Any known RSV strain can be used in the vaccines of the invention. The nanoemulsion RSV vaccines can comprise RSV whole virus from more than one strain of RSV, as well as RSV antigens from more than one strain of RSV.

Examples of useful strains of RSV include, but are not limited to, any RSV strain, including subgroup A and B genotypes, as well as RSV strains deposited with the ATCC, such as: (1) Human RSV strain A2, deposited under ATCC No. VR-1540; (2) Human RSV strain Long, deposited under ATCC No. VR-26; (3) Bovine RSV strain A 51908, deposited under ATCC No. VR-794; (4) Human RSV strain 9320, deposited under ATCC No. VR-955; (5) Bovine RSV strain 375, deposited under ATCC No. VR-1339; (6) Human RSV strain B WV/14617/85, deposited under ATCC No. VR-1400; (7) Bovine RSV strain Iowa (FS1-1), deposited under ATCC No. VR-1485; (8) Caprine RSV strain GRSV, deposited under ATCC No. VR-1486; (9) Human RSV strain 18537, deposited under ATCC No. VR-1580; (10) Human RSV strain A2, deposited under ATCC No. VR-1540P; (11) Human RSV mutant strain A2 cpts-248, deposited under ATCC No. VR-2450; (12) Human RSV mutant strain A2 cpts-530/1009, deposited under ATCC No. VR-2451; (13) Human RSV mutant strain A2 cpts-530, deposited under ATCC No. VR-2452; (14) Human RSV mutant strain A2 cpts-248/955, deposited under ATCC No. VR-2453; (15) Human RSV mutant strain A2 cpts-248/404, deposited under ATCC No. VR-2454; (16) Human RSV mutant strain A2 cpts-530/1030, deposited under ATCC No. VR-2455; (17) RSV mutant strain subgroup B cp23 Clone 1A2, deposited under ATCC No. VR-2579; and (18) Human RSV mutant strain Subgroup B, Strain B1, cp52 Clone 2B5, deposited under ATCC No. VR-2542.

Any suitable amount of RSV immunogen can be used in the nanoemulsion RSV vaccines of the invention. For example, the nanoemulsion RSV vaccine can comprise less than about 100 μg of RSV immunogen (total RSV immunogen and not per RSV immunogen). In another embodiment of the invention, the nanoemulsion RSV vaccine can comprise less than about 90 μg, less than about 80 μg, less than about 70 μg, less than about 60 μg, less than about 50 μg, less than about 40 μg, less than about 30 μg, less than about 20 μg, less than about 15 μg, less than about 10 μg, less than about 9 μg, less than about 8 μg, less than about 7 μg, less than about 6 μg, less than about 5 μg, less than about 4 μg, less than about 3 μg, less than about 2 μg, or less than about 1 μg of RSV immunogen (total RSV immunogen and not per RSV immunogen).

In another embodiment of the invention, the RSV vaccines of the invention comprise about $1.0 \times 10^5$ pfu (plaque forming units (pfu) up to about $1.0 \times 10^8$ pfu, and any amount in-between, of an RSV virus or antigen. The RSV virus or antigen is inactivated by the presence of the nanoemulsion adjuvant. For example, the RSV vaccines can comprise about $1.0 \times 10^5$, $1.1 \times 10^5$, $1.2 \times 10^5$, $1.3 \times 10^5$, $1.4 \times 10^5$, $1.5 \times 10^5$, $1.6 \times 10^5$, $1.7 \times 10^5$, $1.8 \times 10^5$, $1.9 \times 10^5$, $2.0 \times 10^5$, $2.1 \times 10^5$, $2.2 \times 10^5$, $2.3 \times 10^5$, $2.4 \times 10^5$, $2.5 \times 10^5$, $2.6 \times 10^5$, $2.7 \times 10^5$, $2.8 \times 10^5$, $2.9 \times 10^5$, $3.0 \times 10^5$, $3.1 \times 10^5$, $3.2 \times 10^5$, $3.3 \times 10^5$, $3.4 \times 10^5$, $3.5 \times 10^5$, $3.6 \times 10^5$, $3.7 \times 10^5$, $3.8 \times 10^5$, $3.9 \times 10^5$, $4.0 \times 10^5$, $4.1 \times 10^5$, $4.2 \times 10^5$, $4.3 \times 10^5$, $4.4 \times 10^5$, $4.5 \times 10^5$, $4.6 \times 10^5$, $4.7 \times 10^5$, $4.8 \times 10^5$, $4.9 \times 10^5$, $5.0 \times 10^5$, $5.5 \times 10^5$, $6.0 \times 10^5$, $6.5 \times 10^5$, $7.0 \times 10^5$, $7.5 \times 10^5$, $8.0 \times 10^5$, $8.5 \times 10^5$, $9.0 \times 10^5$, $9.5 \times 10^5$, $1.0 \times 10^8$, $1.5 \times 10^6$, $2.0 \times 10^6$, $2.5 \times 10^6$, $3.0 \times 10^6$, $3.5 \times 10^6$, $4.0 \times 10^6$, $4.5 \times 10^6$, $5.0 \times 10^6$, $5.5 \times 10^6$, $6.0 \times 10^6$, $6.5 \times 10^6$, $7.0 \times 10^6$, $7.5 \times 10^6$, $8.0 \times 10^6$, $8.5 \times 10^6$, $9.0 \times 10^6$, $9.5 \times 10^6$, $1.0 \times 10^7$, $1.5 \times 10^7$, $2.0 \times 10^7$, $2.5 \times 10^7$, $3.0 \times 10^7$, $3.5 \times 10^7$, $4.0 \times 10^7$, $4.5 \times 10^7$, $5.0 \times 10^7$, $5.5 \times 10^7$, $6.0 \times 10^7$, $6.5 \times 10^7$, $7.0 \times 10^7$, $7.5 \times 10^7$, $8.0 \times 10^7$, $8.5 \times 10^7$, $9.0 \times 10^7$, $9.5 \times 10^7$, $1.0 \times 10^8$ pfu of an RSV virus.

In one embodiment of the invention, the RSV vaccines comprise F and/or G protein of an RSV strain, such as but not limited to F and/or G protein of RSV strain L19. In another embodiment, the RSV vaccines comprise about 0.1 μg up to about 100 μg, and any amount in-between, of RSV F and/or G protein, such as F and/or G protein of RSV strain L19. For example, the RSV vaccines can comprise about 0.1 μg, about 0.2 μg, about 0.3 μg, about 0.4 μg, about 0.5 μg, about 0.6 μg, about 0.7 μg, about 0.8 μg, about 0.9 μg, about 1.0 μg, about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, about 3.0 μg, about 3.1 μg, about 3.2 μg, about 3.3 μg, about 3.4 μg, about 3.5 μg, about 3.6 μg, about 3.7 μg, about 3.8 μg, about 3.9 μg, about 4.0 μg, about 4.1 μg, about 4.2 μg, about 4.3 μg, about 4.4 μg, about 4.5 μg, about 4.6 μg, about 4.7 μg, about 4.8 μg, about 4.9 μg, about 5.0 μg, about 5.1 μg, about 5.2 μg, about 5.3 μg, about 5.4 μg, about 5.5 μg, about 5.6 μg, about 5.7 μg, about 5.8 μg, about 5.9 μg, about 6.0 μg, about 6.1 μg, about 6.2 μg, about 6.3 μg, about 6.4 μg, about 6.5 μg, about 6.6 μg, about 6.7 μg, about 6.8 μg, about 6.9 μg, about 7.0 μg, about 7.5 μg, about 8.0 μg, about 8.5 μg, about 9.0 μg, about 9.5 μg, about 10.0 μg, about 10.5 μg, about 11.0 μg, about 11.5 μg, about 12.0 μg, about 12.5 μg, about 13.0 μg, about 13.5 μg, about 14.0 μg, about 14.5 μg, about 15.0 μg, about 15.5 μg, about 16.0 μg, about 16.5 μg, about 17.0 μg, about 17.5 µg, about 18.0 µg, about 18.5 µg, about 19.0 µg, about 19.5 µg, about 20.0 µg, about 21.0 µg, about 22.0 µg, about 23.0 µg, about 24.0 µg, about 25.0 µg, about 26.0 µg, about 27.0 µg, about 28.0 µg, about 29.0 µg, about 30.0 µg, about 35.0 µg, about 40.0 µg, about 45.0 µg, about 50.0 µg, about 55.0 µg, about 60.0 µg, about 65.0 µg, about 70.0 µg, about 75.0 µg, about 80.0 µg, about 85.0 µg, about 90.0 µg, about 95.0 µg, or about 100.0 µg of RSV F protein, such as F protein of RSV strain L19.

The RSV immunogen present in the vaccine of the invention can be (1) RSV F protein, (2) RSV G protein; (3) an immunogenic fragment of RSV F protein, (4) an immunogenic fragment of RSV G protein; (5) a derivative of RSV F protein; (6) a derivative of RSV G protein; (7) a fusion protein comprising RSV F protein or an immunogenic fragment of RSV F protein; (8) a fusion protein comprising RSV G protein or an immunogenic fragment of RSV G protein (9) or any combination thereof. Preferably, the RSV vaccine of the invention comprises at least one F protein immunogen and at least one G protein immunogen.

In an embodiment of the invention, an immunogenic fragment G protein of comprises at least 4 contiguous amino acids of the RSV G protein. In other embodiments, the RSV G protein fragment comprises about 4, about 5, about 10, about 15, about 20, about 25, about 50, about 75, about 100, about 125, about 150, about 175, about 200, about 225, about 250, about 275, about 280, about 285, about 289, about 290, about 295, or about 299 contiguous amino acids of RSV G protein. RSV G glycoprotein has about 289 to about 299 amino acids (depending on the virus strain). Conservative amino acid substitutions can be made in the G immunogenic protein fragments to generate G protein derivatives.

In another embodiment of the invention, an immunogenic fragment F protein of comprises at least 4 contiguous amino acids of the RSV F protein. In other embodiments, the RSV F protein fragment comprises about 4, about 5, about 10, about 15, about 20, about 25, about 50, about 75, about 100, about 125, about 150, about 175, about 200, about 225, about 250, about 275, about 300, about 325, about 350, about 375, about 400, about 425, about 450, about 475, or about 500 contiguous amino acids of RSV F protein. Conservative amino acid substitutions can be made in the F immunogenic protein fragments to generate F protein derivatives.

In some embodiments, the F protein derivatives are immunogenic and have a % identify to the F protein selected from the group consisting of 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50%. In some embodiments, the G protein derivatives are immunogenic and have a % identify to the G protein selected from the group consisting of 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50%.

In one embodiment, a vaccine composition will be constructed with isolated viral surface antigens, F and G proteins combined with isolated whole RSV virion particles, which are mixed together with a preferred oil-in-water nanoemulsion.

B. Nanoemulsion

1. Droplet Size

The nanoemulsion RSV vaccine of the present invention comprises droplets having an average diameter size of less than about 1,000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 220 nm, less than about 210 nm, less than about 205 nm, less than about 200 nm, less than about 195 nm, less than about 190 nm, less than about 175 nm, less than about 150 nm, less than about 100 nm, greater than about 50 nm, greater than about 70 nm, greater than about 125 nm, or any combination thereof. In one embodiment, the droplets have an average diameter size greater than about 125 nm and less than or equal to about 600 nm. In a different embodiment, the droplets have an average diameter size greater than about 50 nm or greater than about 70 nm, and less than or equal to about 125 nm.

2. Aqueous Phase

The aqueous phase can comprise any type of aqueous phase including, but not limited to, water (e.g., $H_2O$, distilled water, purified water, water for injection, de-ionized water, tap water) and solutions (e.g., phosphate buffered saline (PBS) solution). In certain embodiments, the aqueous phase comprises water at a pH of about 4 to 10, preferably about 6 to 8. The water can be deionized (hereinafter "$DiH_2O$"). In some embodiments the aqueous phase comprises phosphate buffered saline (PBS). The aqueous phase may further be sterile and pyrogen free.

3. Organic Solvents

Organic solvents in the nanoemulsion RSV vaccines of the invention include, but are not limited to, $C_1$-$C_{12}$ alcohol, diol, triol, dialkyl phosphate, tri-alkyl phosphate, such as tri-n-butyl phosphate, semi-synthetic derivatives thereof, and combinations thereof. In one aspect of the invention, the organic solvent is an alcohol chosen from a nonpolar solvent, a polar solvent, a protic solvent, or an aprotic solvent.

Suitable organic solvents for the nanoemulsion RSV vaccine include, but are not limited to, ethanol, methanol, isopropyl alcohol, propanol, octanol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, sorbitol, industrial methylated spirit, triacetin, hexane, benzene, toluene, diethyl ether, chloroform, 1,4-dioxane, tetrahydrofuran, dichloromethane, acetone, acetonitrile, dimethylformamide, dimethyl sulfoxide, formic acid, polyethylene glycol, an organic phosphate based solvent, semi-synthetic derivatives thereof, and any combination thereof.

4. Oil Phase

The oil in the nanoemulsion RSV vaccine of the invention can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, $C_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, *eucalyptus* leaf oil, lemon grass leaf oil, *melaleuca* leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, dove oil, geranium flower oil, hyssop flower oil, jasmine flower oil, lavender flower oil, manuka flower oil, Marhoram flower oil, orange flower oil, rose flower oil, ylang-ylang flower oil, Bark oil, *cassia* Bark oil, cinnamon bark oil, *sassafras* Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cydomethicone, hexamethylcydotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, *chenopodium* oil, citronellal, citral, citronellol, chamazulene, yarrow, guaiazulene, chamomile, semi-synthetic derivatives, or combinations thereof.

In one aspect of the invention, the volatile oil in the silicone component is different than the oil in the oil phase.

5. Surfactants

The surfactant in the nanoemulsion RSV vaccine of the invention can be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

Exemplary useful surfactants are described in Applied Surfactants: Principles and Applications. Tharwat F. Tadros, Copyright 8 2005 WILEY-VCH Verlag GmbH & Co. KGaA, Weinheim ISBN: 3-527-30629-3), which is specifically incorporated by reference.

Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a non-polar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxysterate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thiglycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or distearate, polyoxyethylene fatty ethers, Polyoxyethylene lauryl ether, Polyoxyethylene stearyl ether, polyoxyethylene myristyl ether, a steroid, Cholesterol, Betasitosterol, Bisabolol, fatty acid esters of alcohols, isopropyl myristate, Aliphati-isopropyl n-butyrate, Isopropyl n-hexanoate, Isopropyl n-decanoate, Isopropyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5$—$(OCH_2CH_2)_y$—OH, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23.

In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis[imidazoyl carbonyl]), nonoxynol-9, Bis(polyethylene glycol bis[imidazoyl carbonyl]), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monodecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quilaja bark, Span® 20, Span® 40, Span® 60, Span® 65, Span® 80, Span® 85, Tergitol, Type 15-8-12, Tergitol, Type 15-8-30, Tergitol, Type 15-8-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton X-100, Triton® X-114, Triton X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quarternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl (tetradecyl)ammonium bromide, 1,3,5-Triazine-1,3,5(2H, 4H,6H)-triethanol, 1-Decanaminium, N-decyl-N, N-dimethyl-, chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy) ethoxy)ethyl dimethyl benzyl ammonium chloride, Alkyl 1 or 3 benzyl-1-(2-hydroxyethyl)-2-imidazolinium chloride, Alkyl bis(2-hydroxyethyl) benzyl ammonium chloride, Alkyl demethyl benzyl ammonium chloride, Alkyl dimethyl 3,4-dichlorobenzyl ammonium chloride (100% $C_{12}$), Alkyl dimethyl 3,4-dichlorobenzyl ammonium chloride (50% $C_{14}$, 40% $C_{12}$, 10% $C_{16}$), Alkyl dimethyl 3,4-dichlorobenzyl ammonium chloride (55% $C_{14}$, 23% $C_{12}$, 20% $C_{16}$), Alkyl dimethyl benzyl ammonium chloride, Alkyl dimethyl benzyl ammonium chloride (100% $C_{14}$), Alkyl dimethyl benzyl ammonium chloride (100% $C_{16}$), Alkyl dimethyl benzyl ammonium chloride (41% $C_{14}$, 28% $C_{12}$), Alkyl dimethyl benzyl ammonium chloride (47% $C_{12}$, 18% $C_{14}$), Alkyl dimethyl benzyl ammonium chloride (55% $C_{16}$, 20% $C_{14}$), Alkyl dimethyl benzyl ammonium chloride (58% $C_{14}$, 28% $C_{16}$), Alkyl dimethyl benzyl ammonium chloride (60% $C_{14}$, 25% $C_{12}$), Alkyl dimethyl benzyl ammonium chloride (61% $C_{11}$, 23% $C_{14}$), Alkyl dimethyl benzyl ammonium chloride (61% $C_{12}$, 23% $C_{14}$), Alkyl dimethyl benzyl ammonium chloride (65% $C_{12}$, 25% $C_{14}$), Alkyl dimethyl benzyl ammonium chloride (67% $C_{12}$, 24% $C_{14}$), Alkyl dimethyl benzyl ammonium chloride (67% $C_{12}$, 25% $C_{14}$), Alkyl dimethyl benzyl ammonium chloride (90% $C_{14}$, 5% $C_{12}$), Alkyl dimethyl benzyl ammonium chloride (93% $C_{14}$, 4% $C_{12}$), Alkyl dimethyl benzyl ammonium chloride (95% $C_{16}$, 5% $C_{18}$), Alkyl dimethyl benzyl ammonium chloride, Alkyl didecyl dimethyl ammonium chloride, Alkyl dimethyl benzyl ammonium chloride, Alkyl dimethyl benzyl ammonium chloride ($C_{12-16}$), Alkyl dimethyl benzyl ammonium chloride ($C_{12-18}$), Alkyl dimethyl benzyl ammonium chloride, dialkyl dimethyl benzyl ammonium chloride, Alkyl dimethyl dimethylbenzyl ammonium chloride, Alkyl dimethyl ethyl ammonium bromide (90% $C_{14}$, 5% $C_{16}$, 5% $C_{12}$), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% $C_{14}$), Alkyl dimethyl isopropylbenzyl ammonium chloride (50% $C_{12}$, 30% $C_{14}$, 17% $C_{16}$, 3% $C_{18}$), Alkyl trimethyl ammonium chloride (58% $C_{18}$, 40% $C_{16}$, 1% $C_{14}$, 1% $C_{12}$), Alkyl trimethyl ammonium chloride (90% $C_{18}$, 10% $C_{16}$), Alkyldimethyl-(ethylbenzyl) ammonium chloride ($C_{12-18}$), Di-($C_{8-10}$)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis (2-hydroxyethyl) octyl hydrogen ammonium chloride, Dodecyl dimethyl benzyl ammonium chloride, Dodecylcarbamoyl methyl dimethyl benzyl ammonium chloride, Heptadecyl hydroxyethylimidazolinium chloride, Hexahydro-1,3,5-tris(2-hydroxyethyl)-s-triazine, Hexahydro-1,3,5-tris(2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysily propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetydimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyttrimethylammonium chloride, cetylbenzyldimethylammonium chloride, cetylpyridinium bromide (CPB), cetyttrimethylammonium bromide (CTAB), cetyidimethylethylammonium bromide, cetyttributylphosphonium bromide, dodecyltrimethylammonium bromide, and tetrad ecyltrimethylammonium bromide. In particularly preferred embodiments, the cationic halogen containing compound is CPC, although the compositions of the present invention are not limited to formulation with an particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4, 1-Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, Trizma® dodecyl sulfate, TWEEN® 80, Ursodeoxycholic acid, semi-synthetic derivatives thereof, and combinations thereof.

Suitable zwitterionic surfactants include, but are not limited to, an N-alkyl betaine, lauryl amido propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio)propanesufonate inner salt, 3-Dodecyldimethyl-ammonio)propanesulfonate inner salt, SigmaUltra, 3-(Dodecyldimethylammonio)-propanesulfonate inner salt, 3-(N,N-Dimethylmyristylammonio)propanesulfonate, 3-(N,N-Dimethyloctadecylammonio)propanesulfonate, 3-(N,N-Dimethyloctyl-ammonio)propanesulfonate inner salt, 3-(N,N-Dimethylpalmitylammonio)-propanesulfonate, semi-synthetic derivatives thereof, and combinations thereof.

In some embodiments, the nanoemulsion RSV vaccine comprises a cationic surfactant, which can be cetylpyridinium chloride. In other embodiments of the invention, the nanoemulsion RSV vaccine comprises a cationic surfactant, and the concentration of the cationic surfactant is less than about 5.0% and greater than about 0.001%. In yet another embodiment of the invention, the nanoemulsion RSV vaccine comprises a cationic surfactant, and the concentration of the cationic surfactant is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, or less than about 0.10%. Further, the concentration of the cationic agent in the nanoemulsion vaccine is greater than about 0.002%, greater than about 0.003%, greater than about 0.004%, greater than about 0.005%, greater than about 0.006%, greater than about 0.007%, greater than about 0.008%, greater than about 0.009%, greater than about 0.010%, or greater than about 0.001%. In one embodiment, the concentration of the cationic agent in the nanoemulsion vaccine is less than about 5.0% and greater than about 0.001%.

In another embodiment of the invention, the nanoemulsion vaccine comprises at least one cationic surfactant and at least one non-cationic surfactant. The non-cationic surfactant is a nonionic surfactant, such as a polysorbate (Tween), such as polysorbate 80 or polysorbate 20. In one embodiment, the non-ionic surfactant is present in a concentration of about 0.01% to about 5.0%, or the non-ionic surfactant is present in a concentration of about 0.1% to about 3%. In yet another embodiment of the invention, the nanoemulsion vaccine comprises a cationic surfactant present in a concentration of about 0.01% to about 2%, in combination with a nonionic surfactant.

In certain embodiments, the nanoemulsion further comprises a cationic halogen containing compound. The present invention is not limited to a particular cationic halogen containing compound. A variety of cationic halogen containing compounds are contemplated including, but not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, and tetradecyltrimethylammonium halides. The present invention nanoemulsion is also not limited to a particular halide. A variety of halides are contemplated including, but not limited to, halide selected from the group consisting of chloride, fluoride, bromide, and iodide.

In still further embodiments, the nanoemulsion further comprises a quaternary ammonium containing compound. The present invention is not limited to a particular quaternary ammonium containing compound. A variety of quaternary ammonium containing compounds are contemplated including, but not limited to, Alkyl dimethyl benzyl ammonium chloride, dialkyl dimethyl ammonium chloride, n-Alkyl dimethyl benzyl ammonium chloride, n-Alkyl dimethyl ethylbenzyl ammonium chloride, Dialkyl dimethyl ammonium chloride, and n-Alkyl dimethyl benzyl ammonium chloride.

In one embodiment, the nanoemulsion and/or nanoemulsion vaccine comprises a cationic surfactant which is cetylpyridinium chloride (CPC). CPC may have a concentration in the nanoemulsion RSV vaccine of less than about 5.0% and greater than about 0.001%, or further, may have a concentration of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, less than about 0.10%, greater than about 0.001%, greater than about 0.002%, greater than about 0.003%, greater than about 0.004%, greater than about 0.005%, greater than about 0.006%, greater than about 0.007%, greater than about 0.008%, greater than about 0.009%, and greater than about 0.010%.

In a further embodiment, the nanoemulsion RSV vaccine comprises a non-ionic surfactant, such as a polysorbate surfactant, which may be polysorbate 80 or polysorbate 20, and may have a concentration of about 0.01% to about 5.0%, or about 0.1% to about 3% of polysorbate 80. The nanoemulsion RSV vaccine may further comprise at least one preservative. In another embodiment of the invention, the nanoemulsion RSV vaccine comprises a chelating agent 6. Additional Ingredients Additional compounds suitable for use in the nanoemulsion RSV vaccines of the invention include but are not limited to one or more solvents, such as an organic phosphate-based solvent, bulking agents, coloring agents, pharmaceutically acceptable excepients, a preservative, pH adjuster, buffer, chelating agent, etc. The additional compounds can be admixed into a previously emulsified nanoemulsion vaccine, or the additional compounds can be added to the original mixture to be emulsified. In certain of these embodiments, one or more additional compounds are admixed into an existing nanoemulsion composition immediately prior to its use.

Suitable preservatives in the nanoemulsion RSV vaccines of the invention include, but are not limited to, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocophemol, ascorbic acid, ascorbyl palmitate, butylated hydroxyanisole, butylated hydroxytoluene, sodium ascorbate, sodium metabisulphite, citric acid, edetic acid, semi-synthetic derivatives thereof, and combinations thereof. Other suitable preservatives include, but are not limited to, benzyl alcohol, chlorhexidine (bis (p-chlorophenyldiguanido) hexane), chlorphenesin (3-(-4-chloropheoxy)-propane-1,2-diol), Kathon CG (methyl and methylchloroisothiazolinone), parabens (methyl, ethyl, propyl, butyl hydrobenzoates), phenoxyethanol (2-phenoxyethanol), sorbic acid (potassium sorbate, sorbic acid), Phenonip (phenoxyethanol, methyl, ethyl, butyl, propyl parabens), Phenoroc (phenoxyethanol 0.73%, methyl paraben 0.2%, propyl paraben 0.07%), Uquipar Oil (isopropyl, isobutyl, butylparabens), Uquipar PE (70% phenoxyethanol, 30% liquipar oil), Nipaguard MPA (benzyl alcohol (70%), methyl & propyl parabens), Nipaguard MPS (propylene glycol, methyl & propyl parabens), Nipasept (methyl, ethyl and propyl parabens), Nipastat (methyl, butyl, ethyl and propyel parabens), Elestab 388 (phenoxyethanol in propylene glycol plus chlorphenesin and methylparaben), and Killitol (7.5% chlorphenesin and 7.5% methyl parabens).

The nanoemulsion RSV vaccine may further comprise at least one pH adjuster. Suitable pH adjusters in the nanoemulsion vaccine of the invention include, but are not limited to, diethyanolamine, lactic acid, monoethanolamine, triethylanolamine, sodium hydroxide, sodium phosphate, semi-synthetic derivatives thereof, and combinations thereof.

In addition, the nanoemulsion RSV vaccine can comprise a chelating agent. In one embodiment of the invention, the chelating agent is present in an amount of about 0.0005% to about 1%. Examples of chelating agents include, but are not limited to, ethylenediamine, ethylenediaminetetraacetic acid (EDTA), phytic acid, polyphosphoric acid, citric acid, gluconic acid, acetic acid, lactic acid, and dimercaprol, and a preferred chelating agent is ethylenediaminetetraacetic acid.

The nanoemulsion RSV vaccine can comprise a buffering agent, such as a pharmaceutically acceptable buffering agent. Examples of buffering agents include, but are not limited to, 2-Amino-2-methyl-1,3-propanediol, ≥99.5% (NT), 2-Amino-2-methyl-1-propanol, ≥99.0% (GC), L-(+)-Tartaric acid, ≥99.5% (T), ACES, ≥99.5% (T), ADA, ≥99.0% (T), Acetic acid, ≥99.5% (GC/T), Acetic acid, for luminescence, ≥99.5% (GC/T), Ammonium acetate solution, for molecular biology, ~5 M in $H_2O$, Ammonium acetate, for luminescence, ≥99.0% (calc. on dry substance, T), Ammonium bicarbonate, ≥99.5% (T), Ammonium citrate dibasic, ≥99.0% (T), Ammonium formate solution, 10 M in $H_2O$, Ammonium formate, ≥99.0% (calc. based on dry substance, NT), Ammonium oxalate monohydrate, ≥99.5% (RT), Ammonium phosphate dibasic solution, 2.5 M in $H_2O$, Ammonium phosphate dibasic, ≥99.0% (T), Ammonium phosphate monobasic solution, 2.5 M in $H_2O$, Ammonium phosphate monobasic, ≥99.5% (T), Ammonium sodium phosphate dibasic tetrahydrate, ≥99.5% (NT), Ammonium sulfate solution, for molecular biology, 3.2 M in $H_2O$, Ammonium tartrate dibasic solution, 2 M in $H_2O$ (colorless solution at 20° C.), Ammonium tartrate dibasic, ≥99.5% (T), BES buffered saline. for molecular biology, 2× concentrate, BES, ≥99.5% (T), BES, for molecular biology, ≥99.5% (T), BICINE buffer Solution, for molecular biology, 1 M in $H_2O$, BICINE, ≥99.5% (T), BIS-TRIS, ≥99.0% (NT), Bicarbonate buffer solution, >0.1 M $Na_2CO_3$, >0.2 M $NaHCO_3$, Boric acid, ≥99.5% (T), Boric acid, for molecular biology, ≥99.5% (T), CAPS, ≥99.0% (TLC), CHES, ≥99.5% (T), Calcium acetate hydrate, ≥99.0% (calc. on dried material, KT), Calcium carbonate, precipitated, ≥99.0% (KT), Calcium citrate tibasic tetrahydrate, 298.0% (calc. on dry substance, KT), Citrate Concentrated Solution, for molecular biology, 1 M in $H_2O$, Citric acid, anhydrous, ≥99.5% (T), Citric acid, for luminescence, anhydrous, ≥99.5% (T), Diethanolamine, ≥99.5% (GC), EPPS, ≥99.0% (T), Ethylenediaminetetraacetic acid disodium salt dihydrate, for molecular biology, ≥99.0% (T), Formic acid solution, 1.0 M in $H_2O$, Gly-Gly-Gly, ≥99.0% (NT), Gly-Gly, 2-99.5% (NT), Glycine, ≥99.0% (NT), Glycine, for luminescence, ≥99.0% (NT), Glycine, for molecular biology, ≥99.0% (NT), HEPES buffered saline, for molecular biology, 2× concentrate, HEPES, ≥99.5% (T), HEPES, for molecular biology, ≥99.5% (T), Imidazole buffer Solution, 1 M in $H_2O$, Imidazole, ≥99.5% (GC), Imidazole, for luminescence, ≥99.5% (GC), Imidazole, for molecular biology, ≥99.5% (GC), Lipoprotein Refolding Buffer, Lithium acetate dihydrate, ≥99.0% (NT), Lithium citrate tribasic tetrahydrate, ≥99.5% (NT), MES hydrate, ≥99.5% (T), MES monohydrate, for luminescence, ≥99.5% (T), MES solution, for molecular biology, 0.5 M in $H_2O$, MOPS, ≥99.5% (T), MOPS, for luminescence, ≥99.5% (T), MOPS. for molecular biology, ≥99.5% (T), Magnesium acetate solution, for molecular biology, ~1 M in $H_2O$, Magnesium acetate tetrahydrate, ≥99.0% (KT), Magnesium citrate tribasic nonahydrate, 298.0% (calc. based on dry substance, KT), Magnesium formate solution, 0.5 M in $H_2O$, Magnesium phosphate dibasic trihydrate, ≥98.0% (KT), Neutralization solution for the in-situ hybridization for in-situ hybridization, for molecular biology, Oxalic acid dihydrate, ≥99.5% (RT), PIPES, ≥99.5% (T), PIPES, for molecular biology, ≥99.5% (T), Phosphate buffered saline, solution (autoclaved), Phosphate buffered saline, washing buffer for peroxidase conjugates in Western Blotting, 10× concentrate, Piperazine, anhydrous, ≥99.0% (T), Potassium D-tartrate monobasic, ≥99.0% (T), Potassium acetate solution, for molecular biology, Potassium acetate solution, for molecular biology, 5 M in $H_2O$, Potassium acetate solution, for molecular biology, ~1 M in $H_2O$, Potassium acetate, ≥99.0% (NT), Potassium acetate, for luminescence, ≥99.0% (NT), Potassium acetate, for molecular biology, ≥99.0% (NT), Potassium bicarbonate, ≥99.5% (T), Potassium carbonate, anhydrous, ≥99.0% (T), Potassium chloride, ≥99.5% (AT), Potassium citrate monobasic, ≥99.0% (dried material, NT), Potassium citrate tribasic solution, 1 M in $H_2O$, Potassium formate solution, 14 M in $H_2O$, Potassium formate, ≥99.5% (NT), Potassium oxalate monohydrate, ≥99.0% (RT), Potassium phosphate dibasic. anhydrous, ≥99.0% (T), Potassium phosphate dibasic, for luminescence, anhydrous, ≥99.0% (T), Potassium phosphate dibasic, for molecular biology, anhydrous, ≥99.0% (T), Potassium phosphate monobasic, anhydrous, ≥99.5% (T), Potassium phosphate monobasic, for molecular biology, anhydrous, ≥99.5% (T), Potassium phosphate tribasic monohydrate, ≥95% (T), Potassium phthalate monobasic, ≥99.5% (T), Potassium sodium tartrate solution, 1.5 M in $H_2O$, Potassium sodium tartrate tetrahydrate, ≥99.5% (NT), Potassium tetraborate tetrahydrate, ≥99.0% (T), Potassium tetraoxalate dihydrate, ≥99.5% (RT), Propionic acid solution, 1.0 M in $H_2O$, STE buffer solution, for molecular biology, pH 7.8, STET buffer solution, for molecular biology, pH 8.0, Sodium 5,5-diethylbarbiturate, ≥99.5% (NT), Sodium acetate solution, for molecular biology, ~3 M in $H_2O$, Sodium acetate trihydrate, ≥99.5% (NT), Sodium acetate, anhydrous, ≥99.0% (NT), Sodium acetate, for luminescence, anhydrous, ≥99.0% (NT), Sodium acetate, for molecular biology, anhydrous, ≥99.0% (NT), Sodium bicarbonate, ≥99.5% (T), Sodium bitartrate monohydrate, ≥99.0% (T), Sodium carbonate decahydrate, ≥99.5% (T), Sodium carbonate, anhydrous, ≥99.5% (calc. on dry substance, T), Sodium citrate monobasic, anhydrous, ≥99.5% (T), Sodium citrate tribasic dihydrate, ≥99.0% (NT), Sodium citrate tribasic dihydrate, for luminescence, ≥99.0% (NT), Sodium citrate tribasic dihydrate, for molecular biology, ≥99.5% (NT), Sodium formate solution, 8 M in $H_2O$, Sodium oxalate, ≥99.5% (RT), Sodium phosphate dibasic dihydrate, ≥99.0% (T), Sodium phosphate dibasic dihydrate. for luminescence, ≥99.0% (T), Sodium phosphate dibasic dihydrate, for molecular biology, ≥99.0% (T), Sodium phosphate dibasic dodecahydrate, ≥99.0% (T), Sodium phosphate dibasic solution, 0.5 M in $H_2O$, Sodium phosphate dibasic, anhydrous, ≥99.5% (T), Sodium phosphate dibasic, for molecular biology, ≥99.5% (T), Sodium phosphate monobasic dihydrate, ≥99.0% (T), Sodium phosphate monobasic dihydrate, for molecular biology, ≥99.0% (T), Sodium phosphate monobasic monohydrate, for molecular biology, ≥99.5% (T), Sodium phosphate monobasic solution, 5 M in $H_2O$, Sodium pyrophosphate dibasic, ≥99.0% (T), Sodium pyrophosphate tetrabasic decahydrate, ≥99.5% (T), Sodium tartrate dibasic dihydrate, ≥99.0% (NT), Sodium tartrate dibasic solution, 1.5 M in $H_2O$ (colorless solution at 20° C.), Sodium tetraborate decahydrate, ≥99.5% (T), TAPS, ≥99.5% (T), TES, ≥99.5% (calc. based on dry substance, T), TM buffer solution, for molecular biology, pH 7.4, TNT buffer solution, for molecular biology, pH 8.0, TRIS Glycine buffer solution, 10× concentrate, TRIS acetate—EDTA buffer solution, for molecular biology, TRIS buffered saline, 10× concentrate, TRIS glycine SDS buffer solution, for electrophoresis, 10× concentrate, TRIS phosphate-EDTA buffer solution, for molecular biology, concentrate, 10× concentrate, Tricine, ≥99.5% (NT), Triethanolamine, ≥99.5% (GC), Triethylamine, ≥99.5% (GC), Triethylammonium acetate buffer, volatile buffer, ~1.0 M in $H_2O$, Triethylammonium phosphate solution, volatile buffer, ~1.0 M in $H_2O$, Trimethylammonium acetate solution, volatile buffer, ~1.0 M in $H_2O$, Trimethylammonium phosphate solution, volatile buffer, ~1 M in $H_2O$, Tris-EDTA buffer solution, for molecular biology, concentrate, 100× concentrate, Tris-EDTA buffer solution, for molecular biology, pH 7.4, Tris-EDTA buffer solution, for molecular biology, pH 8.0, Trizma® acetate, ≥99.0% (NT), Trizma® base, ≥99.8% (T), Trizma® base, ≥99.8% (T), Trizma® base, for luminescence, ≥99.8% (T), Trizma® base, for molecular biology, ≥99.8% (T), Trizma® carbonate, ≥98.5% (T), Trizma® hydrochloride buffer solution, for molecular biology, pH 7.2, Trizma® hydrochloride buffer solution, for molecular biology, pH 7.4, Trizma® hydrochloride buffer solution, for molecular biology, pH 7.6, Trizma® hydrochloride buffer solution, for molecular biology, pH 8.0, Trizma® hydrochloride, ≥99.0% (AT), Trizma® hydrochloride, for luminescence, ≥99.0% (AT), Trizma® hydrochloride, for molecular biology, ≥99.0% (AT), and Trizma® maleate, ≥99.5% (NT).

The nanoemulsion RSV vaccine can comprise one or more emulsifying agents to aid in the formation of emulsions. Emulsifying agents include compounds that aggregate at the oil/water interface to form a kind of continuous membrane that prevents direct contact between two adjacent droplets. Certain embodiments of the present invention feature nanoemulsion vaccines that may readily be diluted with water or another aqueous phase to a desired concentration without impairing their desired properties.

7. Immune Modulators

As noted above, the RSV vaccine can further comprise one or more immune modulators. Examples of immune modulators include, but are not limited to, chitosan and glucan. An immune modulator can be present in the vaccine composition at any pharmaceutically acceptable amount including, but not limited to, from about 0.001% up to about 10%, and any amount inbetween, such as about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10%.

V. Pharmaceutical Compositions

The nanoemulsion RSV subunit vaccines of the invention may be formulated into pharmaceutical compositions that comprise the nanoemulsion RSV vaccine in a therapeutically effective amount and suitable, pharmaceutically-acceptable excipients for pharmaceutically acceptable delivery. Such excipients are well known in the art.

By the phrase "therapeutically effective amount" it is meant any amount of the nanoemulsion RSV vaccine that is effective in preventing, treating or ameliorating a disease caused by the RSV pathogen associated with the immunogen administered in the composition comprising the nanoemulsion RSV vaccine. By "protective immune response" it is meant that the immune response is associated with prevention, treating, or amelioration of a disease. Complete prevention is not required, though is encompassed by the present invention. The immune response can be evaluated using the methods discussed herein or by any method known by a person of skill in the art.

Intranasal administration includes administration via the nose, either with or without concomitant inhalation during administration. Such administration is typically through contact by the composition comprising the nanoemulsion RSV vaccine with the nasal mucosa, nasal turbinates or sinus cavity. Administration by inhalation comprises intranasal administration, or may include oral inhalation. Such administration may also include contact with the oral mucosa, bronchial mucosa, and other epithelia.

Exemplary dosage forms for pharmaceutical administration are described herein. Examples include but are not limited to liquids, ointments, creams, emulsions, lotions, gels, bioadhesive gels, sprays, aerosols, pastes, foams, sunscreens, capsules, microcapsules, suspensions, pessary, powder, semi-solid dosage form, etc.

The pharmaceutical nanoemulsion RSV vaccines may be formulated for immediate release, sustained release, controlled release, delayed release, or any combinations thereof, into the epidermis or dermis. In some embodiments, the formulations may comprise a penetration-enhancing agent. Suitable penetration-enhancing agents include, but are not limited to, alcohols such as ethanol, triglycerides and aloe compositions. The amount of the penetration-enhancing agent may comprise from about 0.5% to about 40% by weight of the formulation.

The nanoemulsion RSV vaccines of the invention can be applied and/or delivered utilizing electrophoretic delivery/electrophoresis. Further, the composition may be a transdermal delivery system such as a patch or administered by a pressurized or pneumatic device (i.e., "gene gun"). Such methods, which comprise applying an electrical current, are well known in the art.

The pharmaceutical nanoemulsion RSV vaccines for administration may be applied in a single administration or in multiple administrations.

If applied topically, the nanoemulsion RSV vaccines may be occluded or semi-occluded. Occlusion or semi-occlusion may be performed by overlaying a bandage, polyoleofin film, article of clothing, impermeable barrier, or semi-impermeable barrier to the topical preparation.

An exemplary nanoemulsion adjuvant composition according to the invention is designated "$W_{80}5EC$" adjuvant. The composition of $W_{80}5EC$ adjuvant is shown in the table below (Table 1). The mean droplet size for the $W_{80}5EC$ adjuvant is ~400 nm. All of the components of the nanoemulsion are included on the FDA inactive ingredient list for Approved Drug Products.

TABLE 1

| $W_{80}5EC$ Formulation | |
|---|---|
| Function | $W_{80}5EC$-Adjuvant<br>Mean Droplet Size ≈400 nm |
| Aqueous Diluent | Purified Water, USP |
| Hydrophobic Oil (Core) | Soybean Oil, USP (super refined) |
| Organic Solvent | Dehydrated Alcohol, USP (anhydrous ethanol) |
| Surfactant | Polysorbate 80, NF |
| Emulsifying Agent Preservative | Cetylpyridinium Chloride, USP |

The nanoemulsion adjuvants are formed by emulsification of an oil, purified water, nonionic detergent, organic solvent and surfactant, such as a cationic surfactant. An exemplary specific nanoemulsion adjuvant is designated as "60% $W_{80}5EC$". The 60% $W_{80}5EC$-adjuvant is composed of the ingredients shown in Table 2 below: purified water, USP; soybean oil USP; Dehydrated Alcohol, USP [anhydrous ethanol]; Polysorbate 80, NF and cetylpyridinium chloride, USP (CPCAII components of this exemplary nanoemulsion are included on the FDA list of approved inactive ingredients for Approved Drug Products.

TABLE 2

| Composition of 60% $W_{80}5EC$-Adjuvant (w/w %) | |
|---|---|
| Ingredients | 60% $W_{80}5EC$ |
| Purified Water, USP | 54.10% |
| Soybean Oil, USP | 37.67% |
| Dehydrated Alcohol, USP (anhydrous ethanol) | 4.04% |
| Polysorbate 80, NF | 3.55% |
| Cetylpyridinium Chloride, USP | 0.64% |

Target patient populations for treatment include, but are not limited to, infants, elderly, transplant patients, and chronic obstructive pulmonary disease (COPD) patients.

VI. Methods of Manufacture

The nanoemulsions of the invention can be formed using classic emulsion forming techniques. See e.g., U.S. 2004/0043041. In an exemplary method, the oil is mixed with the aqueous phase under relatively high shear forces (e.g., using high hydraulic and mechanical forces) to obtain a nanoemulsion comprising oil droplets having an average diameter of less than about 1000 nm. Some embodiments of the invention employ a nanoemulsion having an oil phase comprising an alcohol such as ethanol. The oil and aqueous phases can be blended using any apparatus capable of producing shear forces sufficient to form an emulsion, such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In an exemplary embodiment, the nanoemulsions used in the methods of the invention comprise droplets of an oily discontinuous phase dispersed in an aqueous continuous phase, such as water or PBS. The nanoemulsions of the invention are stable, and do not deteriorate even after long storage periods. Certain nanoemulsions of the invention are non-toxic and safe when swallowed, inhaled, or contacted to the skin of a subject.

The compositions of the invention can be produced in large quantities and are stable for many months at a broad range of temperatures. The nanoemulsion can have textures ranging from that of a semi-solid cream to that of a thin lotion, to that of a liquid and can be applied topically by any pharmaceutically acceptable method as stated above, e.g., by hand, or nasal drops/spray.

As stated above, at least a portion of the emulsion may be in the form of lipid structures including, but not limited to, unilamellar, multilamellar, and pauciamellar lipid vesicles, micelles, and lamellar phases.

The present invention contemplates that many variations of the described nanoemulsions will be useful in the methods of the present invention. To determine if a candidate nanoemulsion is suitable for use with the present invention, three criteria are analyzed. Using the methods and standards described herein, candidate emulsions can be easily tested to determine if they are suitable. First, the desired ingredients are prepared using the methods described herein, to determine if a nanoemulsion can be formed. If a nanoemulsion cannot be formed, the candidate is rejected. Second, the candidate nanoemulsion should form a stable emulsion. A nanoemulsion is stable if it remains in emulsion form for a sufficient period to allow its intended use. For example, for nanoemulsions that are to be stored, shipped, etc., it may be desired that the nanoemulsion remain in emulsion form for months to years. Typical nanoemulsions that are relatively unstable, will lose their form within a day. Third, the candidate nanoemulsion should have efficacy for its intended use. For example, the emulsions of the invention should kill or disable RSV virus to a detectable level, or induce a protective immune response to a detectable level. The nanoemulsion of the invention can be provided in many different types of containers and delivery systems. For example, in some embodiments of the invention, the nanoemulsions are provided in a cream or other solid or semi-solid form. The nanoemulsions of the invention may be incorporated into hydrogel formulations.

The nanoemulsions can be delivered (e.g., to a subject or customers) in any suitable container. Suitable containers can be used that provide one or more single use or multi-use dosages of the nanoemulsion for the desired application. In some embodiments of the invention, the nanoemulsions are provided in a suspension or liquid form. Such nanoemulsions can be delivered in any suitable container including spray bottles and any suitable pressurized spray device. Such spray bottles may be suitable for delivering the nanoemulsions intranasally or via inhalation.

These nanoemulsion-containing containers can further be packaged with instructions for use to form kits.

An exemplary method for manufacturing a vaccine according to the invention for the treatment or prevention of RSV infection in humans comprises: (1) synthesizing in an eukaryotic host, a full length or fragment RSV surface antigen, such as F protein; and/or (2) synthesizing in an eukaryotic host, a full length or fragment RSV surface antigen, such as G protein, wherein the synthesizing is performed utilizing recombinant DNA genetics vectors and constructs. The one or more surface antigens can then be isolated from the eukaryotic host, followed by formulating the one or more RSV surface antigens with an oil in water nanoemulsion. In a further method, whole RSV virions can be cultured in an eukaryotic host, following which the RSV virions can be isolated from the eukaryotic host. The isolated RSV virions can then be formulated with the isolated surface antigens in an oil-in-water nanoemulsion. The eukaryotic host can be, for example, a mammalian cell, a yeast cell, or an insect cell.

VII. Examples

The invention is further described by reference to the following examples, which are provided for illustration only. The invention is not limited to the examples, but rather includes all variations that are evident from the teachings provided herein. All publicly available documents referenced herein, including but not limited to U.S. patents, are specifically incorporated by reference.

Example 1

The purpose of this example was to describe preparation of a nanoemulsion to be used in a nanoemulsion RSV vaccine.

To manufacture the nanoemulsion, the water soluble ingredients are first dissolved in water. The soybean oil is then added and the mixture is mixed using high shear homogenization and/or microfluidization until a viscous white emulsion is formed. The emulsion may be further diluted with water to yield the desired concentration of emulsion or cationic surfactant.

The nanoemulsion (NE) composition was formulated according to Table 3.

TABLE 3

Nanoemulsion composition

| Component | Concentration v/v |
|---|---|
| Water | 84.7% |
| Soybean Oil | 12.6% |
| Ethanol | 1.35% |
| Polysorbate 80 | 1.18% |
| Cetylpyridinium chloride (CPC) | 0.2% |

The nanoemulsion can then be combined with one or more RSV immunogens to form a nanoemulsion RSV vaccine according to the invention.

Example 2

The purpose of this example is to describe exemplary nanoemulsions useful as adjuvants for an RSV vaccine.

A total of 10 nanoemulsion formulations were prepared: $W_{80}5EC$ alone, six $W_{80}5EC$+Poloxamer 407 and Poloxamer 188 (P407 and P188) formulations as well as two $W_{80}5EC$+Chitosan and one $W_{80}5EC$+Glucan formulation have been produced and assessed for stability over 2 weeks under accelerated conditions at 40° C. (Table 4). All 10 nanoemulsions were stable for at least 2 weeks at 40° C.

TABLE 4

$W_{80}5EC$ Formulations

| Nanoemulsion (lot) | Ratios: CPC:Tween:Poloxamer | Method of Addition of Poloxamer | Particle Size (nm) | Zeta Potential (mV) | pH |
|---|---|---|---|---|---|
| $W_{80}5EC$ | 1:6 | — | 450 | 60 | 4.9 |
| $W_{80}5EC$ + 3% P407 | 1:6 | External | 500 | 56 | 5.9 |
| $W_{80}5EC/P407$ | 1:5:1 | Internal | 391 | 46 | 5.5 |
| $W_{80}5EC/P407$ | 1:1:5 | Internal | 253 | 36 | 5.2 |
| $W_{80}5EC/P188$ | 1:5:1 | External | 526 | 54 | 5.1 |
| $W_{80}5EC/P188$ | 1:3:3 | Internal | 416 | 54 | 5.7 |
| $W_{80}5EC/P188$ | 1:1:5 | Internal | 370 | 47 | 5.2 |
| $W_{80}5EC$ + 0.3% Chitosan | 1:6 | External | 505 | 60 | 5.7 |
| $W_{80}5EC$ + 0.3% Chitosan | 1:6 | External | 523 | 60 | 5.4 |
| $W_{80}5EC$ + 0.03% β(1,3) Glucan | 1:6 | External | 491 | 41 | 6.3 |

The following formulations are exemplary nanoemulsions useful in the RSV vaccines of the invention: (1) Formulation 1, $W_{80}5EC$ (NE80), comprising: (a) CPC/Tween 80 (ratio of 1:6), and (b) Particle size ~500 nm (Table 5); and Formulation 2, $W_{80}P_{188}5EC$ (NE188), comprising: (a) CPC/Tween 80/P188 (ratio of 1:1:5), (b) Particle size ~300 nm (Table 6).

TABLE 5

Formulation 1
Composition of 60% $W_{80}5EC$ adjuvant

| Ingredient | w/w % |
|---|---|
| Distilled water | 54.1 |
| CPC | 0.64 |
| Tween 80 | 3.55 |
| Ethanol | 4.04 |
| Soybean oil | 37.7 |

TABLE 6

Formulation 2
Composition of 60% $W_{80}P_{188}5EC$ adjuvant

| Ingredient | w/w % |
|---|---|
| Distilled water | 54.1 |
| CPC | 0.64 |
| Tween 80 | 0.6 |
| Poloxamer 188 | 3 |
| Ethanol | 4.03 |
| Soybean oil | 37.7 |

Example 3

Demonstration of Associated of Nanoemulsion with Viral Antigen

Materials and Methods: Transmission Electron Micrographs and Sectioning Technique: Twenty mL of the NE adjuvant alone or with Fluzone® was fixed with 1% (w/v) osmium tetroxide solution. The fixed preparations were mixed with histogel in 1:10 ratio to form a solid mass. The solid mixture of was sliced into thin 1 mm slices and rinsed with double distilled deionizer water. The cross-sectioned samples were dehydrated with ascending concentrations (30%, 50%, 70%, 90%, 100%) of component A of the Durcupan® kit (Fluka, EM #14020) in double distilled deionizer water. These samples were transferred into embedding solution (mixture of components A, B, C and D) of the Durcupan® kit. The embedded samples were sectioned to a 75 nm thickness and placed on 300 mesh carbon-coated copper grid. The sections on the grids were stained with saturated uranyl acetate in distilled and deionizer water (pH 7) for 10 minutes followed by lead citrate for 5 minutes. The samples were viewed with a Philips CM-100 TEM equipped with a computer controlled compustage, a high resolution (2K×2K) digital camera and digitally imaged and captured using X-Stream imaging software (SEM Tech Solutions, Inc., North Billerica, Mass.).

Results: Electron Micrographs: Cross sectioned TEM of 20% $W_{80}5EC$ NE showed NE droplets with a uniform inner core material. NE vaccine containing 30 µg of HA shows discrete antigen materials/particles inside the oil core of the droplets that represent the Fluzone® antigens. Since the antigen is incorporated in the core, and is surrounded by the core material, it is protected from staining by the electron dense stain. This leads to a white counter staining effect in the core. The localization of the antigen within the core shields the antigen-sensitive protein subunits in the emulsion, and may protect the antigen from degradation, and thus enhancing stability. There are very few Fluzone ® particles outside of the NE particles that were stained dark in color (FIG. 1).

Example 4

The purpose of this example was to evaluate the immunogenic potential, e.g., protective immunity to RSV, of a nanoemulsion-based recombinant F-protein vaccine, comprising $W_{80}5EC$ (adjuvant) and recombinant F protein, in BALB/c mice. Rationale for the example: using recombinant protein as opposed to killed viral preparations potentially offers numerous advantages in regards to consistency, safety, and manufacturing.

Animals were divided randomly into three groups. Groups were immunized on day 0 and boosted on day 28 intranasally (into nares, half volume per nare). Animals were bled prior to prime immunization and then every 2 weeks throughout the duration of the study. To examine whether vaccination with NE-F protein would affect viral clearance and immunopathology, mice were then challenged with live, infectious RSV intranasally ($10^5$ PFU) 2 weeks following the boost immunization.

Test materials: (1) 60% $W_{80}5EC$, diluted to a final concentration of 20%. The components of $W_{80}5EC$ are shown in Table 7 below.

TABLE 7

| $W_{80}5EC$ Formulation | |
|---|---|
| Function | $W_{80}5EC$-Adjuvant; Mean Droplet Size ≈400 nm |
| Aqueous Diluent | Purified Water, USP |
| Hydrophobic Oil (Core) | Soybean Oil, USP (super refined) |
| Organic Solvent | Dehydrated Alcohol USP (anhydrous ethanol) |
| Surfactant | Polysorbate 80, NF |
| Emulsifying Agent Preservative | Cetylpyridinium Chloride, USP |

(2) Recombinant F-protein: (baculovirus host—Sino Biological Inc. Cat 11049-V08B); (3) Phosphate Buffered Saline (sterile) 1×: Supplied by CeliGro; (4) Test animal: BALB/c mice 8-10 weeks old, females (The Jackson Laboratory).

Review of study design: Three groups of BALB/c mice were immunized against F-protein as follows: (1) Prime immunization: Group I—4.45 μg F-protein+20% $W_{80}5EC$ at the total volume 15 μl (n=8); Group II—4.45 μg F-protein at the total volume 15 μl (n=5); and Group III—PBS at the total volume 15 μl (n=10); and (2) Boost immunization: Group I—10 μg F-protein+20% $W_{80}5EC$ at the total volume 15 μl (n=8); Group II—10 μg F-protein at the total volume 15 μl (n=5); and Group III—PBS at the total volume 15 μl (n=10).

Animals were divided randomly into three groups. Groups were immunized on day 0 intranasally (into nares, half volume per nare). Animals were bled every 2 weeks for the duration of the experiment. The mice were intranasally inoculated with $10^5$ PFU L19 RSV 14 days following the final boost.

Methods: Test formulation: The vaccine mixture was formulated as follows. First immunization: (1) 90 μl of recombinant F protein (conc. 0.445 mg/ml) was mixed with 45 μl of 60% $W_{80}5EC$. Final concentrations: F protein—0.3 mg/ml; NE—20%. Volume dose—15 μl/animal. (2) 50 ul of recombinant F protein (conc. 0.445 mg/ml) was mixed with 25 μl of PBS 1×. Final concentrations: F protein—0.3 mg/ml; NE —0%. Volume dose—15 μl/animal. For the immunization boost: (1) 90 μl of recombinant F protein (conc. 1 mg/ml) was mixed with 45 μl of 60% $W_{80}5EC$. Final concentrations: F protein—0.67 mg/ml; NE—15%. Volume dose—15 μl/animal; and (2) 50 ul of recombinant F protein (conc. 1 mg/ml) was mixed with 25 μl of PBS 1×. Final concentrations: F protein—0.67 mg/ml; NE —0%. Volume dose—15 μl/animal.

Test methods. Vaccination procedure: Mice were anesthetized with isoflurane and positioned with their heads reclined about 45° then 7.5 μl vaccine was administered into the left nare. The animals were re-anesthetized and restrained as above. The remaining 7.5 μl of the vaccine was administered into the right nare. Physical examination: Body posture, activity, and pilorection were monitored on weekly basis for each individual animal in the study. Bleeding: Two, 4 and 6 weeks after the first immunization mice were bled by saphenous phlebotomy.

Serum ELISA: Antigen-specific IgG, IgG1, IgG2a, IgG2b, and IgE responses were measured by ELISA with 5 μg/ml of F-protein for plate coating. Anti-mouse IgG-alkaline phosphatase conjugated antibodies were from Jackson ImmunoResearch Laboratories Inc. (West Grove, Pa.). Alkaline phosphatase (AP) conjugated rabbit anti-mouse IgG (H&L), IgG1, IgG2a, IgG2b, IgG2c and IgE were purchased from Rockland Immunochemicals, Inc. (Gilbertsville, Pa.).

Intranasal challenge with live L19 RSV: Mice were challenged with live, infectious RSV intranasally ($10^5$ PFU) 2 weeks post boost immunization.

Airway hyperreactivity (AHR): AHR was measured using a Buxco mouse plethysmograph which is specifically designed for the low tidal volumes (Buxco). The mouse to be tested was anesthetized with sodium pentobarbital and intubated via cannulation of the trachea with an 18-gauge metal tube. The mouse was subsequently ventilated with a Harvard pump ventilator (tidal volume=0.4 ml, frequency=120 breaths/min, positive end-expiratory pressure 2.5-3.0 cm $H_2O$). The plethysmograph was sealed and readings monitored by computer. As the box is a closed system, a change in lung volume will be represented by a change in box pressure (Pbox) that was measured by a differential transducer. Once baseline levels had stabilized and initial readings were taken, a methacholine challenge was given via tail vein injection. After determining a dose-response curve (0.01-0.5 mg), an optimal dose was chosen, 0.250 mg of methacholine. This dose was used throughout the rest of the experiments in this study. After the methacholine challenge, the response was monitored and the peak airway resistance was recorded as a measure of airway hyperreactivity.

Euthanasia and biological material harvest procedure: The mice were euthanized by isoflurane asphyxiation. Lung-associated lymph nodes were harvested for immune response evaluation. Intranasal inoculation of mice with Line 19 RSV, leads to an infection that is associated with a moderate form of disease phenotype, including mucus hypersecretion and inflammation. The severity of this phenotype in control and immunized animals was assessed using histologic analysis and QPCR for viral and cytokine gene expression as well as mucus-associated genes Muc5ac and Gob5.

Quantitative PCR: The smallest lung lobe was removed and homogenized in 1 ml of Trizol reagent (Invitrogen). RNA was isolated as per manufacturer's protocol, and 5 µg was reverse-transcribed to assess gene expression. Detection of cytokine mRNA in lung samples was determined using pre-developed primer/probe sets (Applied Biosystems) and analyzed using an ABI Prism 7500 Sequence Detection System (Applied Biosystems). Transcript levels of Muc5ac, Gob5 were determined using custom primers, as previously described [1]. Gapdh was analyzed as an internal control and gene expression was normalized to Gapdh. Fold changes in gene expression levels were calculated by comparison to the gene expression in uninfected mice, which were assigned an arbitrary value of 1. RSV transcripts were amplified using SYBR green chemistry, by adapting previously published primer sets to match the sequence of Line 19:

```
SVG sense:
                                    (SEQ ID NO: 1)
5'-CCAAACAAACCCAATAATGATTT-3'

RSVG antisense:
                                    (SEQ ID NO: 2)
5'-GCCCAGCAGGTTGGATTGT-3'

RSVN sense:
                                    (SEQ ID NO: 3)
5'-CATCTAGCAAATACACCATCCA-3'

RSVN antisense:
                                    (SEQ ID NO: 4)
5'-TTCTGCACATCATAATTAGGAGTATCAA-3'

RSVF sense:
                                    (SEQ ID NO: 5)
5'-AATGATATGCCTATAACAAATGATCAGAA-3'

RSVF antisense:
                                    (SEQ ID NO: 6)
5'-TGGACATGATAGAGTAACTTTGCTGTCT-3'
```

The levels of RSV transcripts in the lungs were expressed relative to the number of copies of GAPDH.

Plaque assays: Lungs of mice were excised, weighed, and homogenized in 1×EMEM (Lonza). Homogenates were clarified by centrifugation (5000×g for 10 mins), serial dilutions were made of the supernatant and added to sub-confluent Vero cells. After allowing the virus to adhere for one hour, the supernatant was removed, and replaced with 0.9% methylcellulose/EMEM. Plaques were visualized on day 5 of culture by immunohistochemical techniques using goat anti-RSV as the primary antibody (Millipore), HRP-rabbit anti-goat antibody as the secondary, and 4-chloronapthol (Pierce) as the substrate.

Lymph node restimulation: Lung associated lymph node (LALN) cell suspensions were plated in duplicate at $1 \times 10^6$ cells per well followed by restimulation with either media or RSV (MOI~0.5). Cells were incubated at 37° C. for 24 hours and supernatants collected for analysis on the BioRad Bioplex 200 system according to the manufacturer's protocol. Kits (BioRad) containing antibody beads to Th cytokines (IL-17, IFNγ, IL-4, IL-5, IL-13) were used to assay for cytokine production in each of the samples.

Histology: Right lobes of the lungs were isolated and immediately fixed in 10% neutral buffered formalin. Lung samples were subsequently processed, embedded in paraffin, sectioned, and placed on L-lysine-coated slides, and stained using standard histological techniques using Hemotoxylin and Eosin (H&E) and Periodic-acid Schiff (PAS). PAS staining was done to identify mucus and mucus-producing cells.

Figure 2:
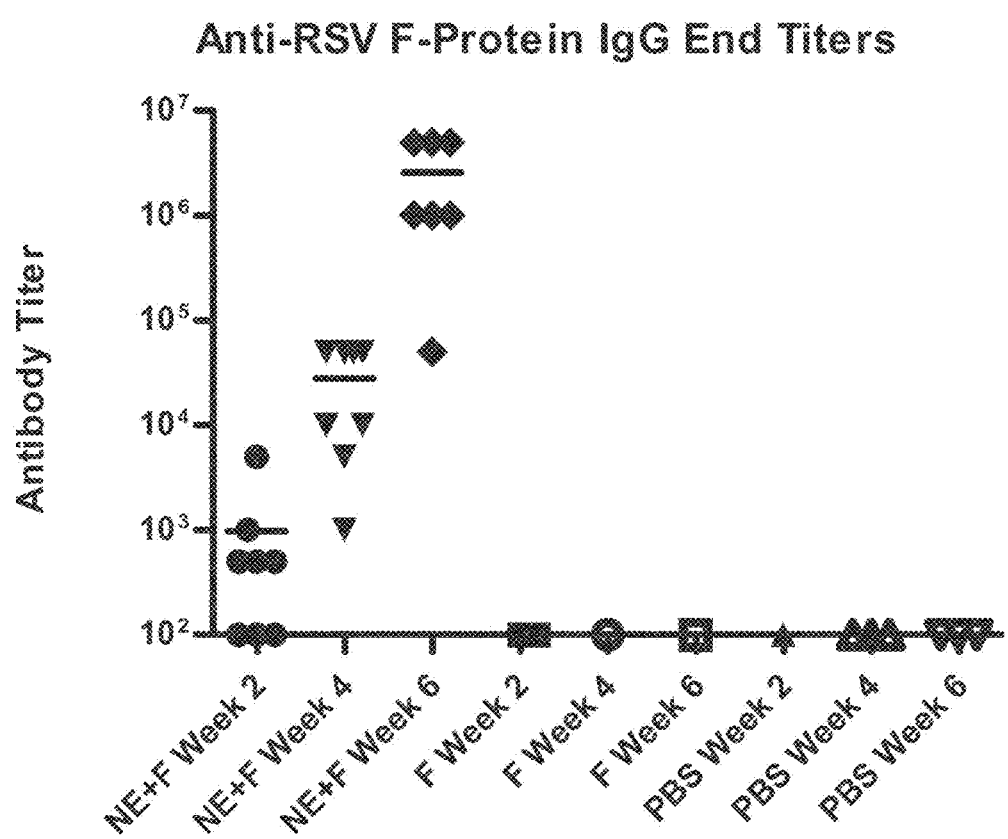
FIG. 2: Shows endpoint titer of RSV specific IgG in sera of BALB/c mice immunized with RSV. Only group immunized with 20% $W_{80}5EC$ mixed with F-protein responded to vaccination. The bar represents group average.

Results. Evaluation of humoral response. Evaluation of Specific Serum IgG. Sera obtained from mice 2, 4 and 6 weeks after the prime immunization were used to assess the endpoint titer of specific IgG using ELISA. Endpoint titer was defined as the highest sera dilution yielding absorbance three times above the background. Endpoint titer results are shown in FIG. 2. Only nanoemulsoin F-protein immunized mice responded vaccination by high titers of specific anti-F-protein IgG antibodies with group average titers approaching $5 \times 10^6$ at week 6.

Figure 3A:
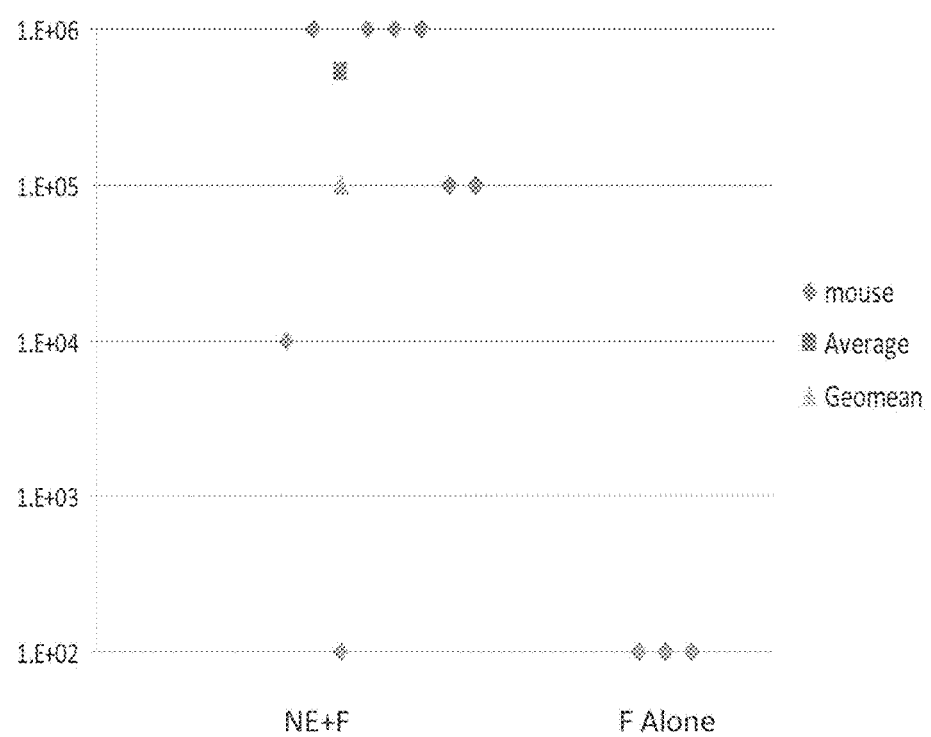
FIGS. 3A-3D: Shows endpoint titer of RSV specific IgG1 (FIG. 3A), IgG2a (FIG. 3B), IgG2b (FIG. 3C), and IgE (FIG. 3D) in sera of BALB/c mice immunized with NE+F ptn. Sera were obtained two weeks after the second immunization.
Figure 3B:
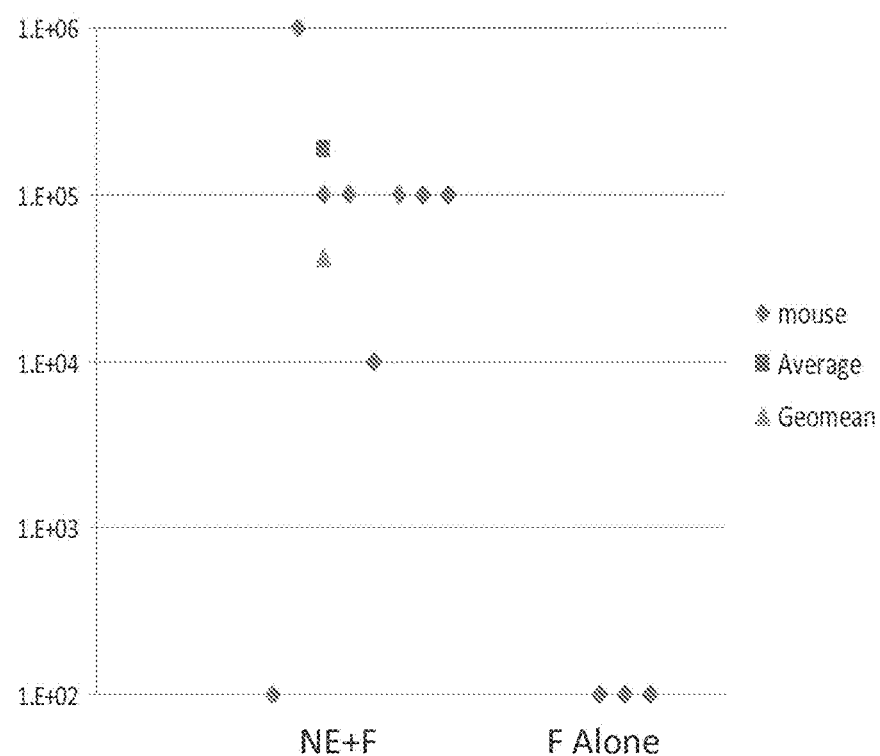
Figure 3C:
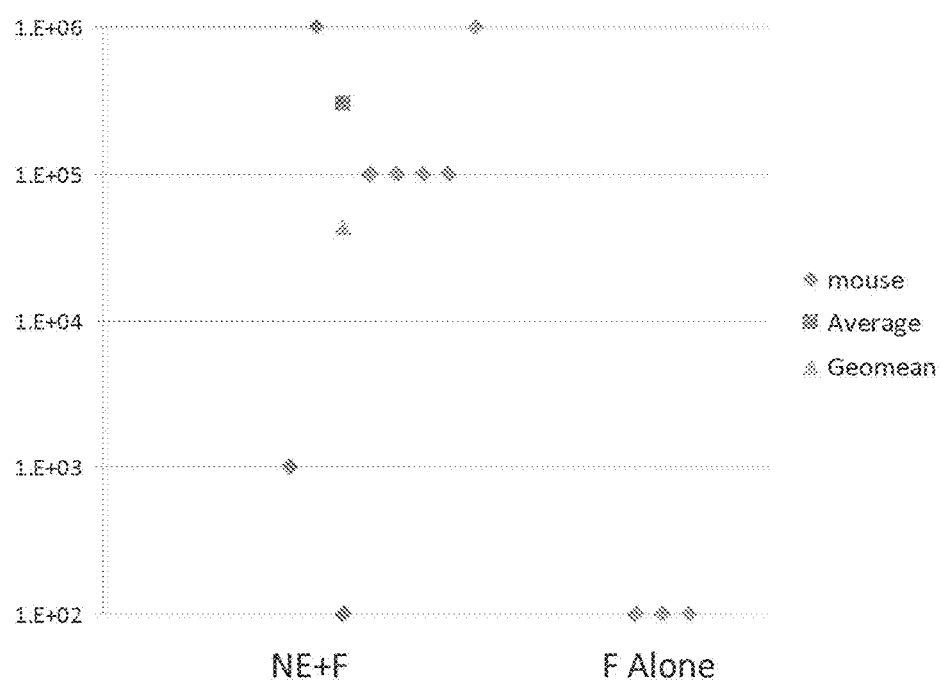
Figure 3D:
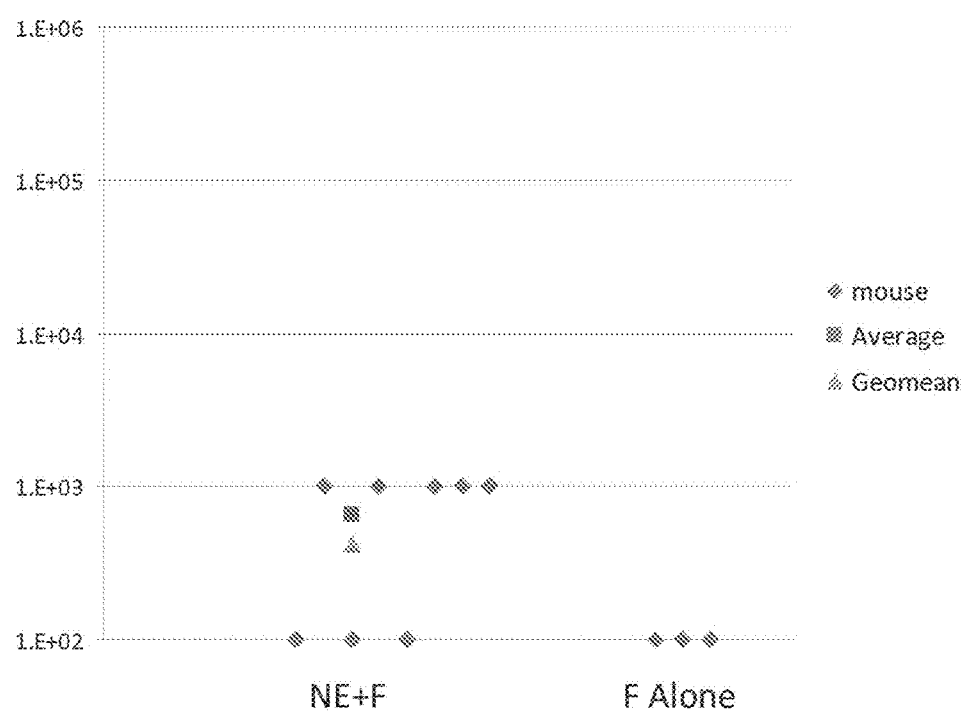

Evaluation of specific IgG1, IgG2a, IgG2b, and IgE humoral response in sera to immunization. Sera obtained from mice two weeks after the second immunization (week 6) were used to assess the endpoint titer of specific IgG1, IgG2a, IgG2b, and IgE using ELISA (FIG. 3). Endpoint titer was defined as the highest serum dilution yielding absorbance three times above the background. NE+F-protein immunized mice produced high levels of levels of specific IgG1, IgG2a, IgG2b antibodies (FIGS. 3A, 3B and 3C). Serum IgE titers were low but present and averaged around 663 for NE+F-protein immunized mice (FIG. 3D).

Figure 4:
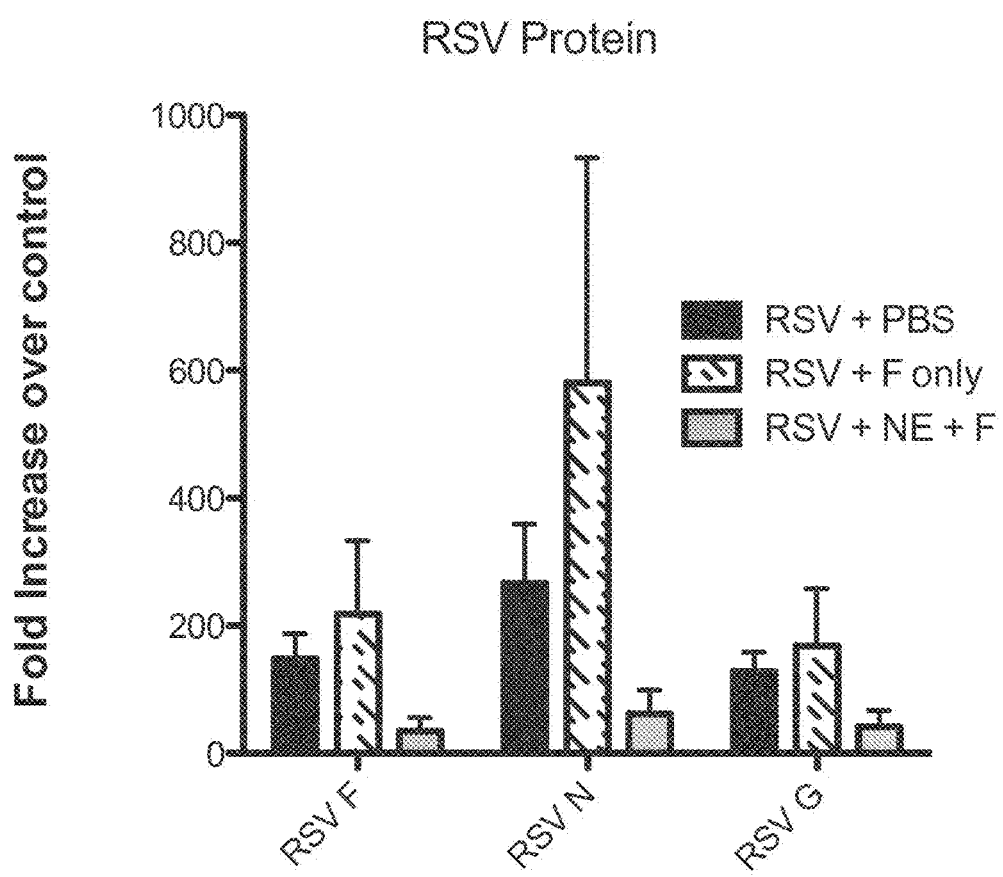
FIG. 4: Shows the results of vaccination of mice with nanoemulsion (NE)-F-protein attenuates disease following intranasal challenge with live RSV. Immunized mice were vaccinated intranasally (i.n.) twice at day 0 and day 28 with NE+F-protein, F-protein alone or treated with PBS only. Control and vaccinated mice were challenged 2 weeks following the boost (i.n.) with 105 PFU live RSV. The expression of virus transcripts were determined at day 8 post-infection via QPCR of lung RNA.

RSV Challenge: RSV Gene expression in lungs 8 days following challenge. A challenge study was conducted to determine whether vaccination with NE–F-protein would protect the mice from respiratory challenge with RSV. At 6 weeks following prime immunization, mice were challenged with live, infectious RSV intranasally ($10^5$ PFU). On day 8 post-challenge, viral load was assessed in the lungs via QPCR and via plaque assay. As assessed via QPCR, a significant decrease in the transcript levels for RSV F and RSV N and RSV G were detected in the lungs of NE–F-protein vaccinated mice in comparison to non-immunized and F-protein only immunized mice (FIG. 4). These data indicate that NE–F-protein vaccine dramatically improves viral clearance in the following lower respiratory challenge.

Figure 5:
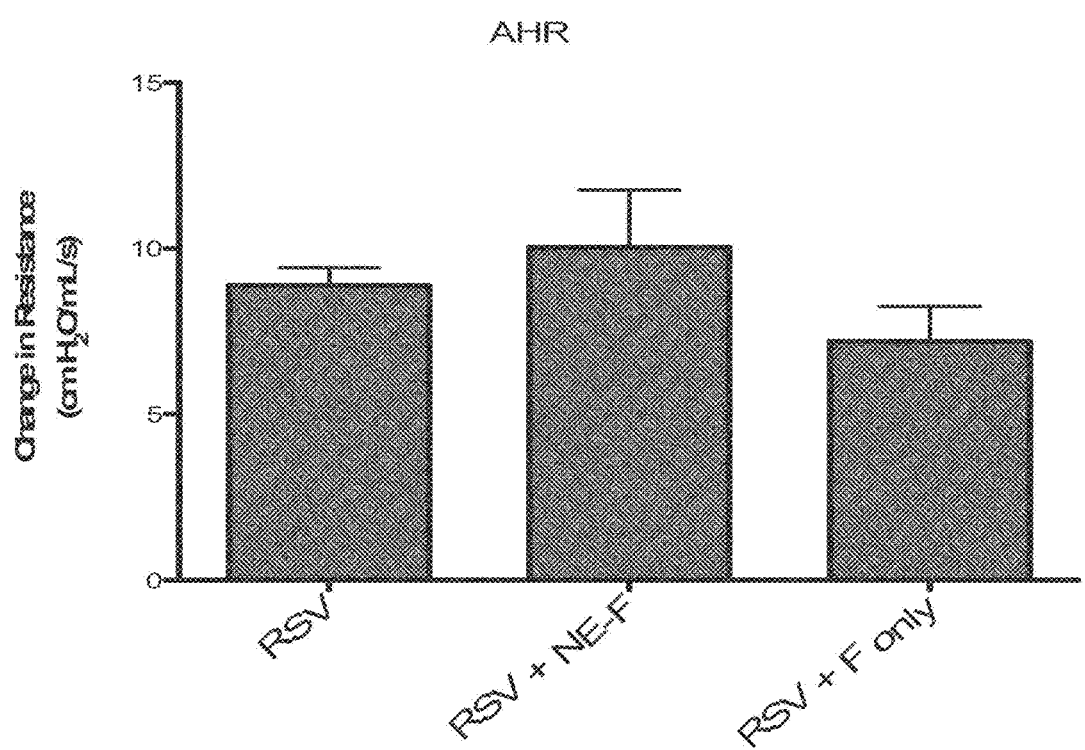
FIG. 5: Shows that nanoemulsion (NE)-RSV immunization does not promote immunopotentiation when compared to non-vaccinated mice. Mice were vaccinated with NE-RSV as described below. Control and vaccinated mice were challenged at day 56. Airway hyperreactivity was assessed at day 8 post-challenge via plethysmography. Columns represent the increase in airway resistance following a single, optimized intravenous dose of methacholine.

Nanoemulsion+-RSV does not Promote Airway Hyperreactivity. As previously reported, vaccination with formalin fixed RSV promotes the development of airway hyperreactivity (AHR) and eosinophilia upon live viral challenge. With this in mind, whether nanoemulsion+F-protein vaccination promotes airway hyper-reactivity, or other evidence of immunopotentiation, was evaluated. Compared to control RSV infected mice, nanoemulsion-RSV immunized mice exhibited only baseline increases in airway resistance following intravenous methacholine challenge (FIG. 5).

Figure 6A:
FIGS. 6A-6B: Shows that inflammation and mucus production in nanoemulsion (NE)+F-protein vaccinated mice does not differ from controls.
Figure 6B:
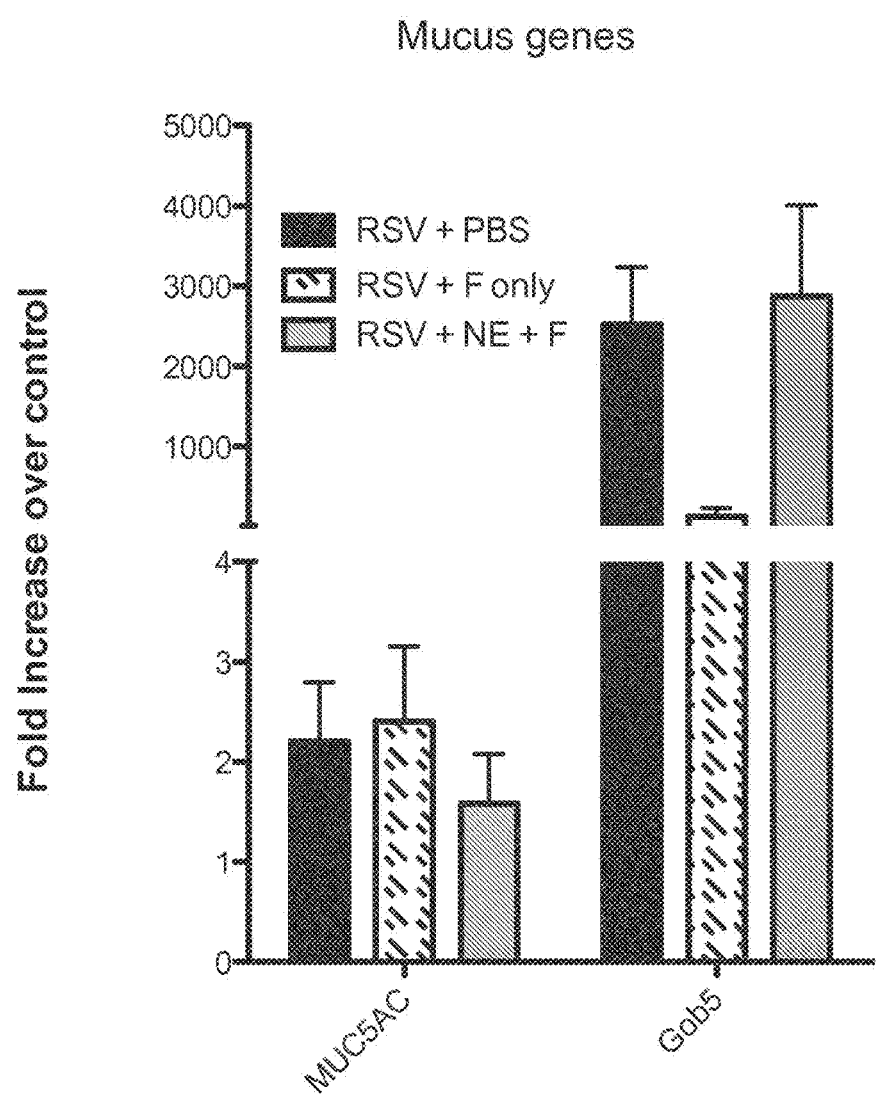

Nanoemulsion+F-protein Immunization is Associated with Mucus Secretion Following Live Challenge. Intranasal inoculation of mice with Line 19 RSV, leads to an infection that is associated with a moderate form of disease phenotype, including mucus hypersecretion and inflammation. The severity of this phenotype in control and immunized animals was assessed using histologic analysis and QPCR for viral and cytokine gene expression. At day 8, post-challenge, NE+F-protein vaccinated mice exhibited similar mucus hypersecretion compared to challenged non-immunized mice, as assessed via histologic analysis (FIG. 6A). Similar expression of the mucus-associated genes Muc5ac and Gob5 was measured in NE–F-protein immunized mice compared to non-immunized controls (FIG. 6B).

Nanoemulsion+F-protein immunization promotes induction of mixed Th1 and Th2 cytokines following challenge.

Figure 7A:
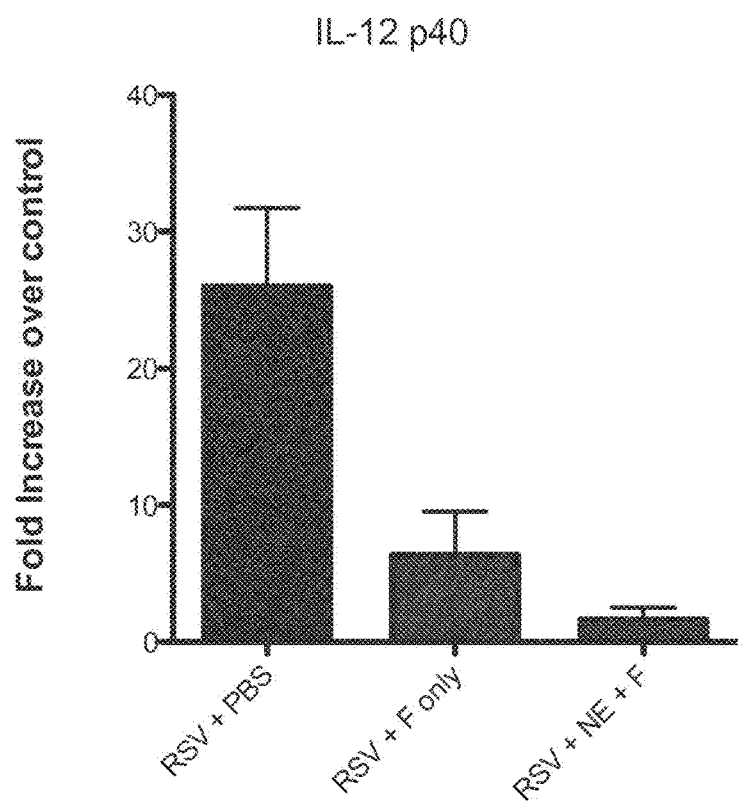
FIGS. 7A-7C: Shows that nanoemulsion (NE)+F-protein vaccination promotes mixed Th1 and Th2 responses. Mice were vaccinated with NE+F-protein F-protein alone as described below, and challenged with live RSV. In (FIG. 7A), the expression of IL-12(p40) and (FIG. 7B) IL-17 cytokines were assessed from lung RNA via QPCR. In (FIG. 7C) Lung associated lymph node (LALN) cell suspensions were restimulation with RSV (MOI,0.5). Supernatants collected for analysis on the Bioplex to assay for cytokine production in each of the samples.
Figure 7B:
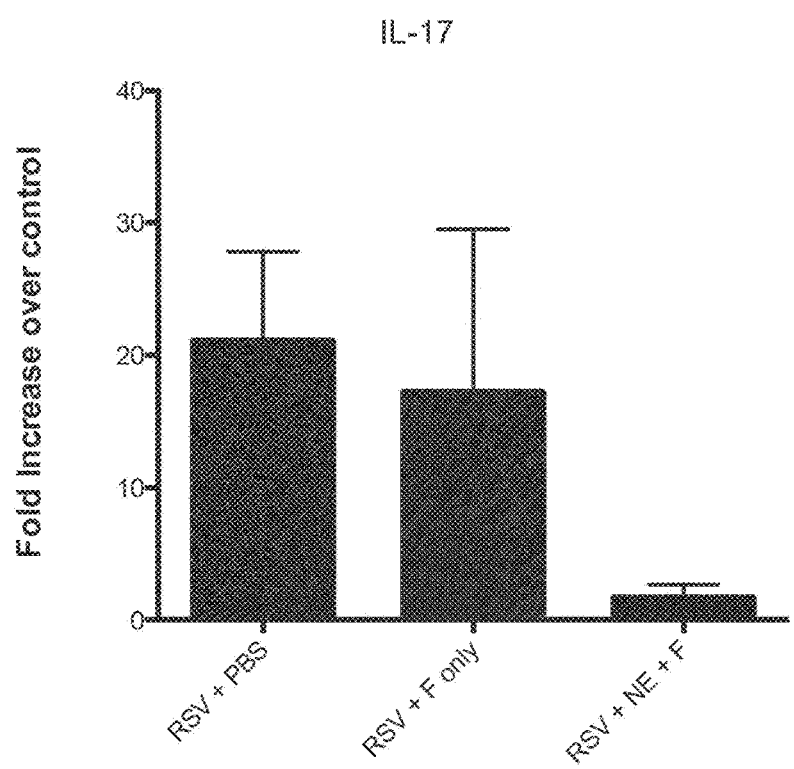
Figure 7C:
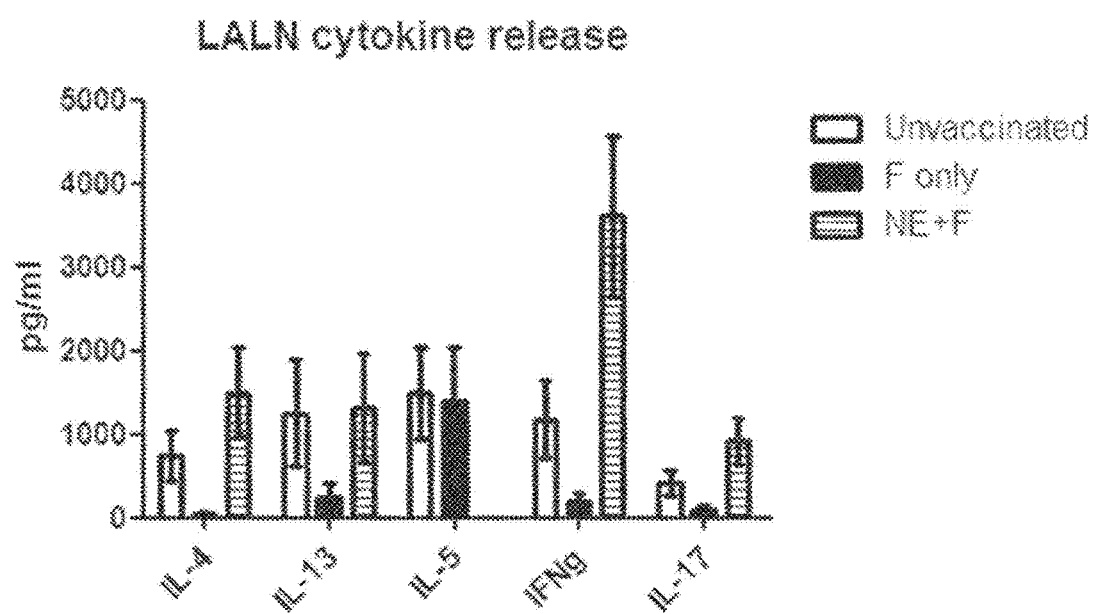

The further characterize the immunization phenotype that promoted viral clearance in nanoemulsion+F-protein immunized; we used QPCR for cytokine gene expression. Compared to control mice, nanoemulsion+F-protein vaccinated mice did not exhibit IL-12 and IL-17, as assessed by the levels of RSV transcripts in the lungs at day 8 post challenge (FIGS. 7A and B respectively). As a means of validation, cytokine profiles were assessed in bronchoalveolar lavage and lung homogenates via multiplex antibody-based assay (Bioplex). NE-RSV vaccination showed an enhanced IFN-γ response. IL-17 showed increase production compared to unvaccinated mice (FIG. 7C).

Conclusions: Only the group immunized with 20% W$_{80}$5EC mixed with F-protein responded to vaccination with high titers of specific anti-RSV IgG, IgG1, IgG2a and IgG2b antibodies. This was associated with minimal production of IgE. Nanoemulsion+F-protein vaccination was also associated with enhanced viral clearance and protection following live RSV challenge. Interestingly, the phenotype of the immune response was not associated with production of IL-12 or IL-17.

A mixed Th1, Th2 pattern of cytokine release was observed for NE+F-protein immunized mice both in lymph nodes after re-stimulation in vitro with RSV L19. However, this was not associated with immunopotentiation although significant mucus production was observed.

Example 5

RSV is a leading cause of severe lower respiratory tract disease in infants, elderly, and immunocompromised individuals. Currently there is no vaccine available. Antibodies against surface protein F are considered important in host defense against RSV infection, however, protection is incomplete and of limited duration.

Materials and Methods: L19 RSV virus was inactivated by formulation with W$_{80}$5EC nanoemulsion. BALB/c mice were vaccinated intranasally at weeks 0 and 4 with 12 μL of inactivated L19 virus containing 1.2 μg of RSV F protein at 1.3×10$^5$ PFU/dose+20% W$_{80}$5EC or recombinant RSV F at 2.5 μg/dose+20% W$_{80}$5EC. Both vaccine formulations were compared to unimmunized animals upon challenge. Serum from immunized animals was collected prior immunization and at week 4 post second immunization. Animals were challenged oropharyngeally with 10$^5$ PFU of L19 RSV strain at 10 weeks post-immunization and tested for viral RNA clearance using PCR and histopathological change by microscopy.

Figure 8:
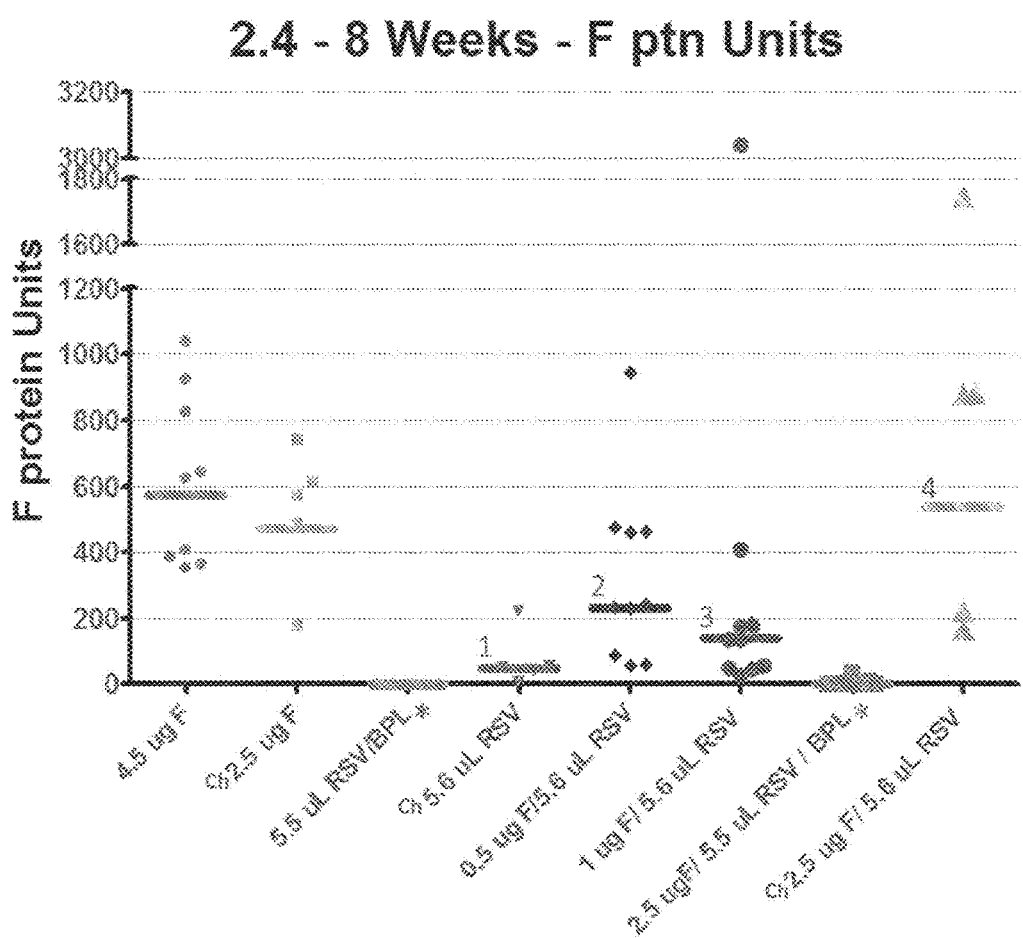
FIG. 8: Shows F protein units measured following administration/immunization with various formulations: (1) 4.5 µg F protein, (2) 2.5 µg F protein, (3) 5.5 µL RSV/β-propiolactone (β-PL); (4) 5.6 µL RSV; (5) 0.5 µg F/5.6 µL RSV; (6) 1 µg F/5.6 µL RSV/β-propiolactone (β-PL); and (7) 2.5 µg F/5.6 µL RSV.
Figure 9:
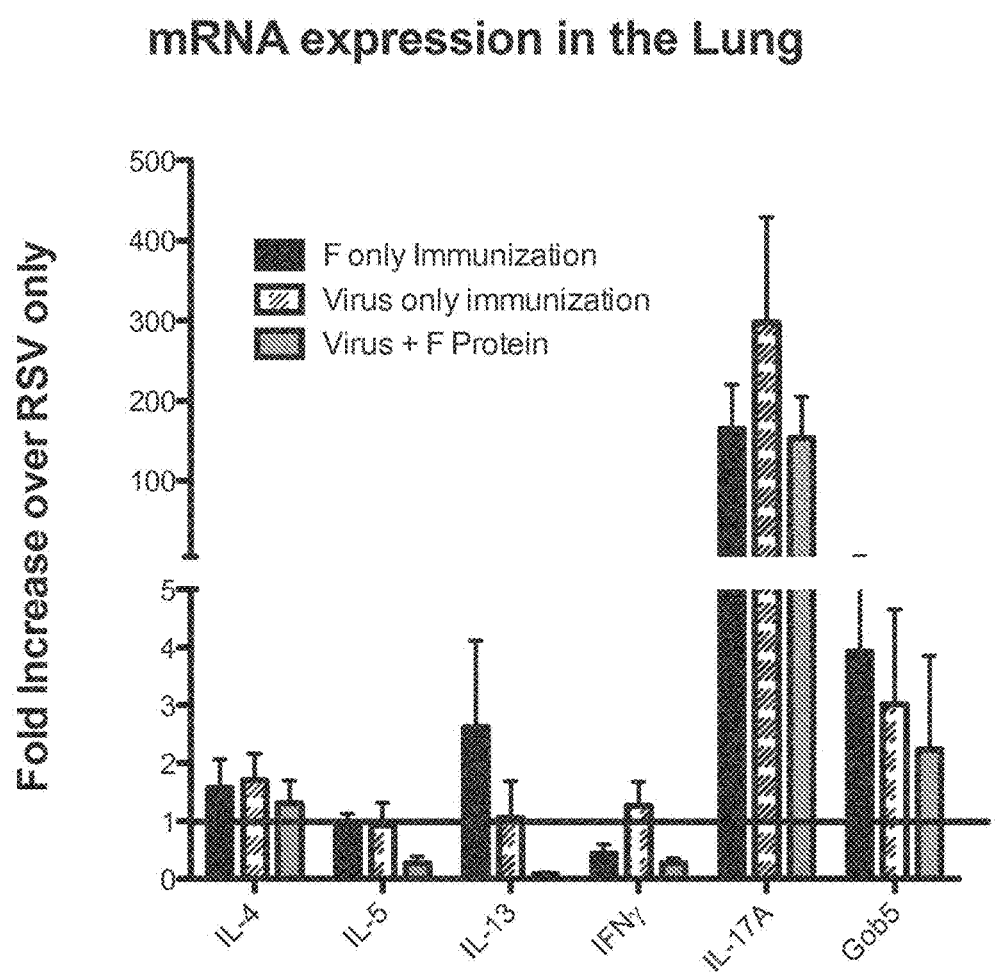
FIG. 9: Shows mRNA expression in the lung for IL-4, IL-5, IL-13, IFNγ, IL-17A, and Gob5 following immunization with (1) F protein only; (2) RSV virus only; and (3) RSV virus+F protein.
Figures 10A, 10B, 10C, 10D:
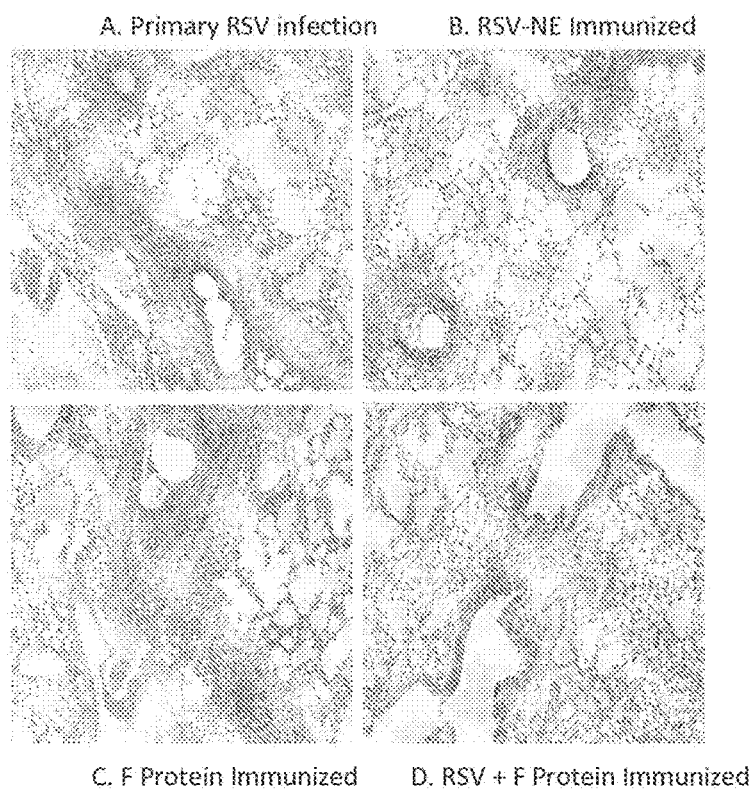
FIGS. 10A-10D: Shows a histological examination of immunized and challenged mice.

Results: Both inactivated whole virus and recombinant F protein produced an immune response and reduced viral mRNA after challenge (p<0.01 by Mann Whitney). Anti-F ELISA units reached a geometric mean (GM) of 51 (95% CI 14-189) following whole virus vaccination and were lower compared to a GM of 470 (95% CI 235-942) following F protein vaccination (p=0.02 by Mann-Whitney). See FIG. 8. F protein was undetectable after challenge in 100% of mice vaccinated with whole virus, however, whereas 100% mice vaccinated with recombinant F protein had detectable F protein mRNA in lungs post challenge (p=0.008 by Fisher's exact test). See FIG. 9 and Table 8. Additionally, the histopathology of animals vaccinated with whole virus had less mucus than animals vaccinated with F protein. See FIGS. 10A-10D.

TABLE 8

Number of mice with detectable RSV proteins by PCR

| Immunization Group | F Protein | G Protein | N Protein |
| --- | --- | --- | --- |
| No immunization | 5/5 | 5/5 | 5/5 |
| F Protein Only | 5/5 (0.03) | 5/5 (0.010) | 5/5 (2.3) |

TABLE 8-continued

Number of mice with detectable RSV proteins by PCR

| Immunization Group | F Protein | G Protein | N Protein |
| --- | --- | --- | --- |
| RSV | 0/5 | 3/5 | 0/5 |
| RSV + F protein | 2/5 | 4/5 | 0/5 |

Conclusions: Whole virus and recombinant F protein induce an immune response and reduce viral mRNA after challenge. Despite lower antibody titer, whole virus vaccine inactivated and adjuvanted with W$_{80}$5EC nanoemulsion results in improved viral clearance and reduced histopathology upon challenge.

Example 6

The purpose of this example is to compare HRSV Protein Expression for RSV A2 strain as compared to RSV L19 strain, and Cell Lysate vs. Supernatant.

Materials and Methods: All samples were prepared by infecting HEP-2 cells with the same amount of pfu from either A2 or L19 viruses. Twenty four hours post infection; the infected cells were treated with either one of the following:

(1) Cell lysate to check for the cell associated proteins; after discarding the supernatant media, the cells were treated with SDS. This cell lysate was assayed for quantity of F protein associated with the cells.

(2) Total cell and supernatant proteins; the cells and supernatant were frozen and thawed 3 times to lyse the cells and all the cell lysate was used to assay the F protein in the cells and the media.

L19 and A2 virus was extracted and purified from HEP-2 infected cells 4 days following infection. Purified virus was compared for protein contents.

Results: Normalized samples were assayed in Western blots using a polyclonal anti RSV antibodies. F and G protein contents were compared between L19 and A2 strains. The density of the bands was compared using image capturing and a Kodak software. A mock non-infected cell culture was prepared as a control.

Figure 11:
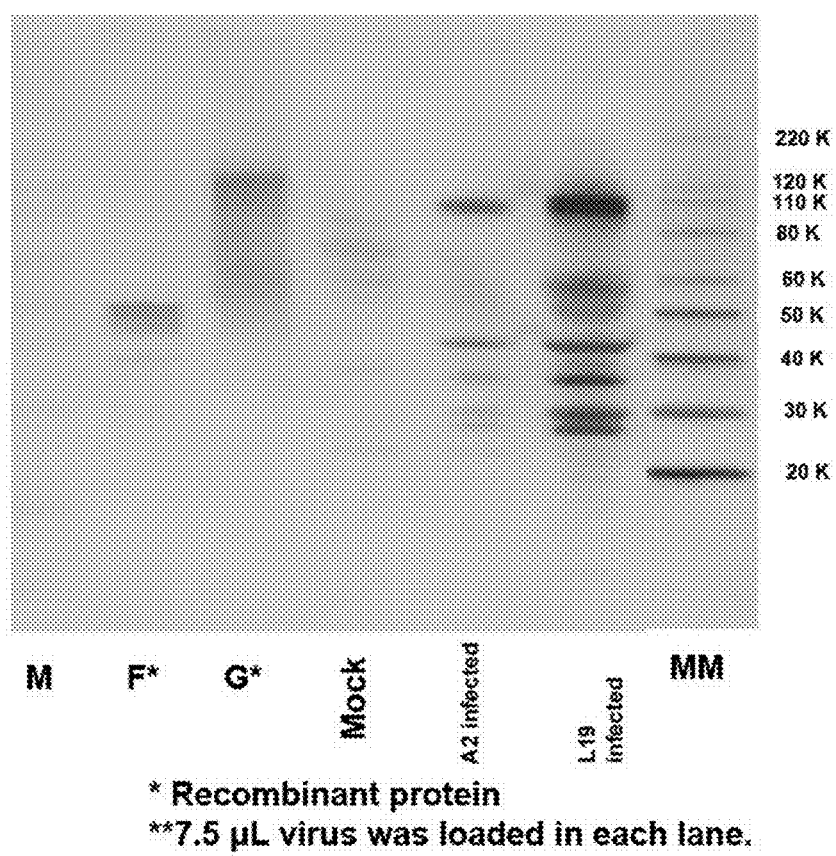
FIG. 11: Shows an SDS PAGE of HRSV Infected Cell Lysate (SDS treated) with L19 and A2.
Figure 12:
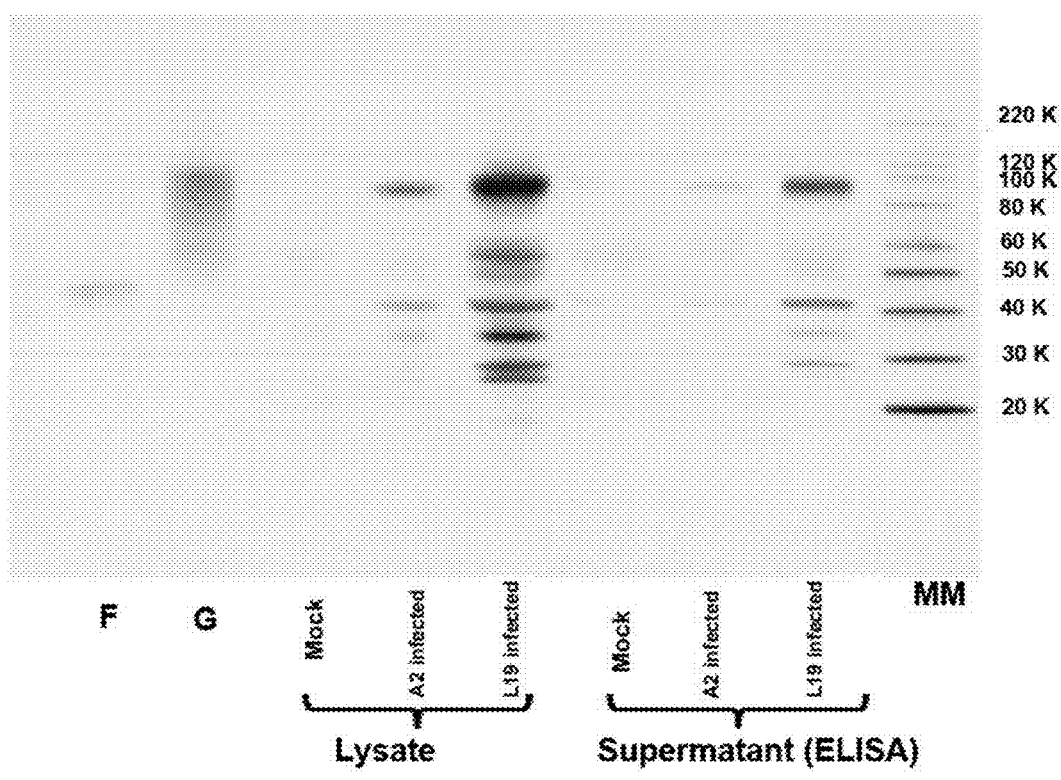
FIG. 12: Shows an SDS-PAGE of RSV strain L19 and RSV strain A2 HRSV Cell Lysate (cells & supernatant).
Figure 13:
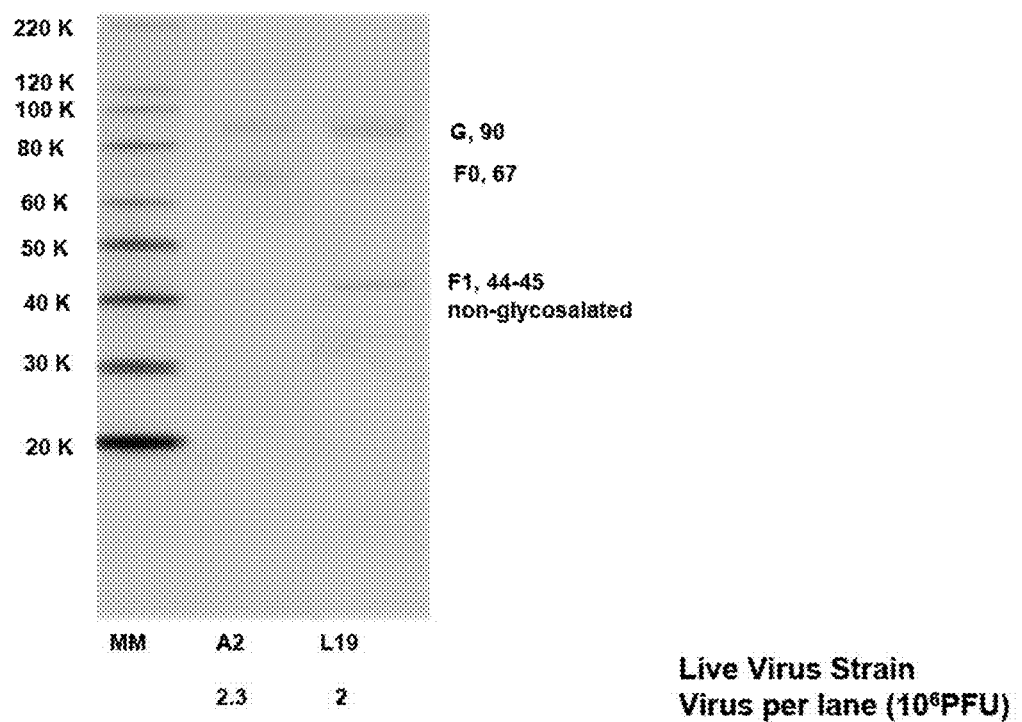
FIG. 13: Shows an SDS PAGE of HRSV strain L19 and strain A2 Purified Virus.

The results data are detailed in FIGS. 11-13 and Tables 9-11. FIG. 11 shows an SDS PAGE of HRSV Infected Cell Lysate (SDS treated) with L19 and A2, FIG. 12 shows an SDS-PAGE of L19 and A2 HRSV Cell Lysate (cells & supernatant), and FIG. 13 shows an SDS PAGE of HRSV L19 and A2 Purified Virus. Table 9 shows comparable HRSV F and G protein from L19 and A2 levels from SDS-PAGE. Table 10 shows comparable HRSV L19 and A2 F and G protein from infected cells (Lysate, Supernatant). Finally, Table 11 shows comparable HRSV L19 and A2 F and G protein from SDS PAGE.

TABLE 9

Comparable HRSV F and G Protein from L19 and A2 Levels from SDS-PAGE

| | Mock | Infected with A2 | Infected with L19 | Band Density Ratio (L19/A2) |
| --- | --- | --- | --- | --- |
| G (90 kDa) | No Band | 78241.1 | 356946.3 | 4.56 |
| F2 (44-45 kDa) | No Band | 38612 | 121328 | 3.14 |

TABLE 10

Comparable HRSV L19 and A2 F and G Protein from Infected Cells (Lysate, Supernatant)

|  | Lysate | | | Supernatant | | |
| --- | --- | --- | --- | --- | --- | --- |
|  | Mock | infected with A2 | infected with L19 | Mock | Infected with A2 | Infected with L19 |
| G (90 kDa) | No Band | 27831 | 166308 | 0 | 4686 | 54142 |
| Ratio of L19:A2 |  |  | 6 |  |  | 11.6 |
| F2 (44-45 kDa) | No Band | 10645 | 43570 | No Band | 1860 | 18499 |
| Ratio of L19:A2 |  |  | 4.1 |  |  | 9.9 |

TABLE 11

Comparable HRSV L19 and A2 F and G Protein From SDS PAGE

|  | A2 ($2.3 \times 10^6$ pfu) | L19 ($2 \times 10^6$ pfu) | Ratio (L19/A2) |
| --- | --- | --- | --- |
| G | 5,039.1 | 11,401.1 | 2.26 |
| F0 + F2 | 4,481.81 | 9,700.39 | 2.16 |

Summary: RSV L19 virus infected cells produce between 3-11 fold higher quantities of RSV viral proteins as compared to A2 infected cells.

Example 7

The purpose of this example was to compare F protein expression in Hep-2 cells infected with different strains of RSV virus (L19 vs. A2) for various infection times (24 hours vs. 4 days).

Materials and Methods: Hep-2 cells were infected with either L19 or A2 RSV virus. 2 sets of 4 flasks total.

24 hours after virus infection, the first set of Hep-2 cells were lysed with or without culture supernatant. Samples were prepared as the following:

TABLE 12

| Plate 1 Infect with L19 | Plate 2 Infect with L19 | Plate 3 Infect with A2 | Plate 4 Infect with A2 |
| --- | --- | --- | --- |
| 24 hrs later | | | |
| Discard Medium Add Tris Buffer (same volume) Lyze cells Lot # 1123, C + T | Leave medium in Lyze cells Lot # 1124, C + M | Discard medium Add Tris buffer Tris (Same volume) Lyze cells Lot # 1125, C + T | Leave medium in Lyze cells Lot # 1126, C + M |

C+TCCC+T=Cell+Tris Buffer (culture medium was discarded and replaced with equal volume of Tris buffer);

C+M=Cell+Culture Medium (culture medium reserved).

Four days after infection, the second set of Hep-2 cells were lysed with or without culture supernatant. Samples were prepared as the following:

TABLE 13

| Plate A Infected with L19 | Plate B | Plate C | Plate D Infected with A2 |
| --- | --- | --- | --- |
| 4 days later | | | |
| Remove Medium and Save | Leave Medium in | Remove Medium and Save | Leave Medium in |
| Add Buffer (same volume) Lyse cells | Saved Medium Lyse cells | Add buffer (Same volume) Lyse cells | Saved Medium Lyse cells |

C+T=Cell+Tris Buffer (culture medium was replaced with equal volume of Tris buffer)

M=Culture Medium (culture medium was collected separately)

C+M=Cell+Culture Medium (culture medium reserved)

Some 7.5 µL of each sample was applied for Western blot analysis. The density of F and G protein bands were measured using Carestream Molecular Imaging Software 5.X.

Figure 14:
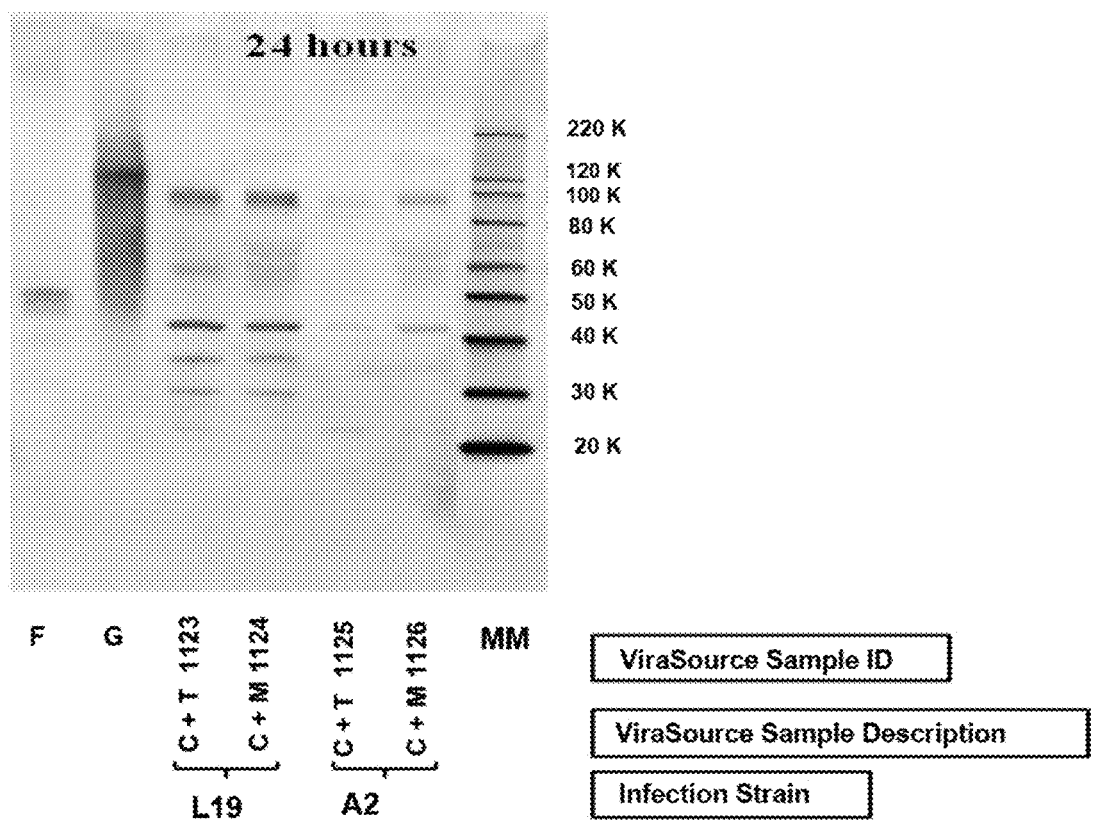
FIG. 14: Shows a Western blot of HRSV strain L19 and strain A2 F and G Protein expression 24 hours after Virus Infection.

Results: The results are detailed in FIG. 14, which shows a Western blot of HRSV L19 and A2 F and G protein expression 24 hours after virus infection. In addition, Table 14 below shows a density analysis of HRSV F and G protein band from Western Blot.

TABLE 14

HRSV F and G Protein Band Density Analysis From Western Blot

| | | Sample Collection Time | | | | | | | | | |
| --- | --- | --- | --- | --- | --- | --- | --- | --- | --- | --- | --- |
| | | 24 hours After Infection | | | | 4 Days After Infection | | | | | |
| | | ViraSource Sample ID | | | | | | | | | |
| | | 1123 | 1124 | 1125 | 1126 | 1127 | 1128 | 1129 | 1130 | 1131 | 1132 |
| | | | | | | Virus Strain | | | | | |
| | | L19 | | A2 | | L19 | | | A2 | | |
| Sample Description | | C + T | C + M | C + T | C + M | C + T | M | C + M | C + T | M | C + M |
| Band Density | G (90 kDa) | 37130.4 | 39563.9 | 5076.6 | 15489.7 | 70377.4 | 70980.1 | 89469.8 | 5986.2 | 18172.8 | 19615.9 |
| | F2 (44-45 kDa) | 24309.2 | 22565.6 | 2160.4 | 7173.5 | 34426.1 | 25094.9 | 41726.3 | 6994.2 | 9542.6 | 7122.8 |
| Concentration (µg/mL) | G (90 kDa) | 7.7 | 8.2 | 1.1 | 3.2 | 8.9 | 9.0 | 11.4 | 0.8 | 2.3 | 2.5 |

TABLE 14-continued

HRSV F and G Protein Band Density Analysis From Western Blot

| | Sample Collection Time | | | | | | | | | |
|---|---|---|---|---|---|---|---|---|---|---|
| | 24 hours After Infection | | | | 4 Days After Infection | | | | | |
| | ViraSource Sample ID | | | | | | | | | |
| | 1123 | 1124 | 1125 | 1126 | 1127 | 1128 | 1129 | 1130 | 1131 | 1132 |
| | Virus Strain | | | | | | | | | |
| | L19 | | A2 | | L19 | | | A2 | | |
| Sample Description | C + T | C + M | C + T | C + M | C + T | M | C + M | C + T | M | C + M |
| F2 (44-45 kDa) | 36.8 | 34.1 | 3.3 | 10.9 | 32.5 | 23.7 | 39.4 | 6.6 | 9.0 | 6.7 |

Summary: Both cell-associated viral particles and culture media-associated viral particles express much higher F (about 6 fold average) in L19 infected cells as compared to those infected with RSV A2 strain.

In addition, both cell-associated viral particles and culture media-associated viral particles express much higher G in L19 infected cells compared to those infected with RSV A2 strain.

Example 8

The purpose of this example was to compare several different approaches for inactivation of RSV, including β-propiolactone and W$_{80}$5EC Nanoemulsion, via nasal vaccination in a mouse.

Methods: W$_{80}$5EC, an oil-in-water nanoemulsion with both antiviral and adjuvant activity, was compared with β-propiolactone (β-PL) inactivated virus (strain L19 @2×105 pfu/dose). The two vaccines were administered intranasally (IN) to BALB/C mice at weeks 0 and 4. Mice were bled prior to dosing and at 3 weeks post-boost and then tested for specific antibodies against F-protein.

Animals were challenged nasally with 1×10$^5$ pfu RSV L19 at week 8 and checked for airway hyper-reactivity (AHR), lung cytokines, and viral protein mRNA clearance using PCR.

Results: Both W$_{80}$5EC and β-PL completely inactivated RSV and induced an immune response. β-PL vaccine induced higher antibody response compared to nanoemulsion-inactivated vaccine (p=0.006). Animals vaccinated with nanoemulsion-inactivated vaccine, however, had higher clearance of the RSV following the challenge, evidenced by lower proteins F and G mRNA in the lungs (p=0.06 and 0.0004, respectively). Moreover, animals receiving nanoemulsion-inactivated vaccine demonstrated a significant lower AHR (p=0.02). Both vaccines induced significant levels of lung IL-17 as compared to nonvaccinated control (<0.01), however, significantly higher levels were induced by nanoemulsion-inactivated vaccine (p=0.009).

Conclusions: β-PL inactivated RSV virus vaccine is associated with AHR following viral challenge in a mouse model of RSV infection. In contrast, nanoemulsion viral inactivation produced no AHR and induced a significantly increased IL-17 production and improved viral clearance. This suggests a novel pathway of immune protection that may provide benefit for vaccination against RSV.

Example 9

The purpose of this example is to describe RSV viral strains useful in the vaccines of the invention.

L19 RSV strain was evaluated as an antigen in the nanoemulsion inactivated/nanoemulsion adjuvanted RSV vaccine. This strain was found to cause infection and enhanced respiratory disease (ERD) in mice. Moreover, data published showed that it conferred protection without induction of ERD in mice when formulated with nanoemulsion. This L19 strain was compared to a Wildtype A2 strain obtained from the American Type Culture Collection (ATCC).

The RSV Strain L19 isolate was isolated from an RSV-infected infant with respiratory illness in Ann Arbor, Mich. on 3 Jan. 1967 in WI-38 cells and passaged in SPAFAS primary chick kidney cells followed by passage in SPAFAS primary chick lung cells prior to transfer to MRC-5 cells (Herlocher 1999) and subsequently Hep2 cells (Lukacs 2006). Comparison of RSV L19 genome (15,191-nt; GenBank accession number FJ614813) with the RSV strain A2 (15,222-nt; GenBank accession number M74568) shows that 98% of the genomes are identical. Most coding differences between L19 and A2 are in the F and G genes. Amino acid alignment of the two strains showed that F protein has 14 (97% identical) and G protein has 20 (93% identical) amino acid differences.

RSV L19 strain has been demonstrated in animal models to mimic human infection by stimulating mucus production and significant induction of IL-13 using an inoculum of 1×10$^5$ plaque forming units (PFU)/mouse by intra-tracheal administration (Lukacs 2006).

Rationale for Selection of RSV L19 Strain: Importantly and uniquely, the RSV L19 viral strain is unique in that it produces significantly higher yields of F protein (approximately 10-30 fold more per PFU) than the other strains. F protein content may be a key factor in immunogenicity and the L19 strain currently elicits the most robust immune response. The L19 strain has a shorter propagation time and therefore will be more efficient from a manufacturing perspective. NanoBio proposes to produce RSV L19 strain virus for the vaccine in a qualified Vero cell line following single plaque isolation of the L19 strain and purification of the virus to establish a Master Viral Seed Bank and Working Viral Seed Bank. The results comparing the three viral strains are provided in Table 15.

TABLE 15

Comparison of RSV Strains

| RSV Strain | Days of Propagation | RSV F protein (µg/mL) | RSV G protein (µg/mL) | G/F Ratio | Viral Titer (PFU/mL) |
|---|---|---|---|---|---|
| L 19 | 4-5 | 110 | 603 | 5.5 | $0.5 \times 10^7$ |
| A2 Wild Type[1] | 4-5 | 44 | 108 | 2.5 | $1.9 \times 10^7$ |
| rA2cp248/404[2] | 8-9 | 38 | 284 | 7.5 | $0.5 \times 10^8$ |

[1] ATCC (strain number VR-1540), Virus was isolated from an RSV infected infant with respiratory illness in Melbourne, Australia in 1961 and has been propagated in HEp-2 cell culture at least 27 times (Lewis 1961). This virus has been treated to remove adenovirus from the original deposit and has been utilized as a challenge strain in human clinical trials (Lee 2004).
[2] Recombinant temperature-sensitive A2 mutant virus obtained from the NIH (Whitehead 1998).

Example 10

The purpose of this example is to describe Inactivation of RSV L19 viral strain with different nanoemulsion adjuvants.

The nanoemulsions (1) $W_{80}5EC$, (2) $W_{80}5EC$ with P407; (3) $W_{80}5EC$ with P188, (4) $W_{80}5EC$ with high and low molecular weight Chitosan, and (5) $W_{80}5EC$ with Glucan, have been tested with the RSV L19 viral strain to determine viral inactivation.

Figure 15:
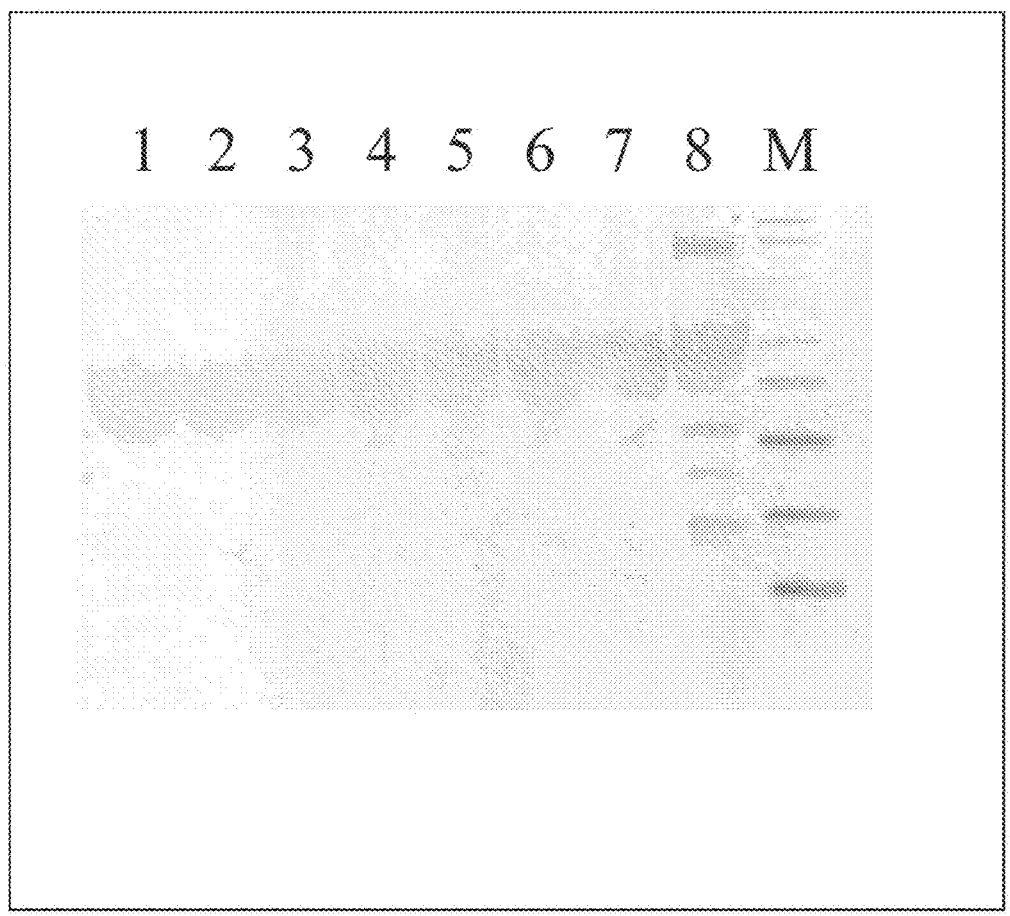
FIG. 15: Shows the viral inactivation by Western blot assessment, with lanes containing: (1) $W_{80}5EC$ (Lane 1), (2) $W_{80}5EC+0.03\%$ B 1,3 Glucan (lane 2), (3) $W_{80}5EC+0.3\%$ Chitosan (medium molecular weight)+acetic acid (lane 3), (4) $W_{80}5EC+0.3\%$ P407 (lane 4), (5) $W_{80}5EC+0.3\%$ Chitosan (low molecular weight)+0.1% acetic acid (lane 5), (6) media alone (lane 6); (7) βPL-inactivated virus (lane 7), and (8) L19 positive control (lane 9).
Figures 16A, 16B:
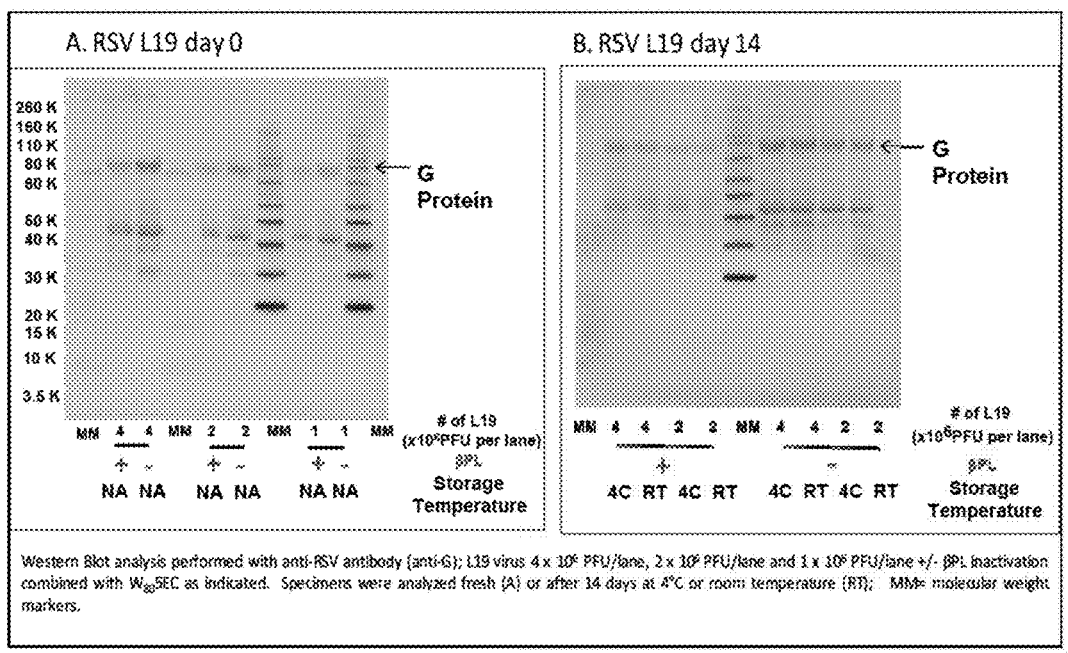
FIGS. 16A-16B: Shows Western blot analysis performed with anti-RSV antibody (anti-G); L19 virus $4\times10^6$ PFU/lane, $2\times10^6$ PFU/lane, and $1\times10^6$ PFU/lane+/−βPL inactivation combined with $W_{80}5EC$ as indicated. Specimens were analyzed fresh (FIG. 16A) or after 14 days at 4° C. or room temperature (RT) (FIG. 16B). MM=Molecular weight.
Figure 17:
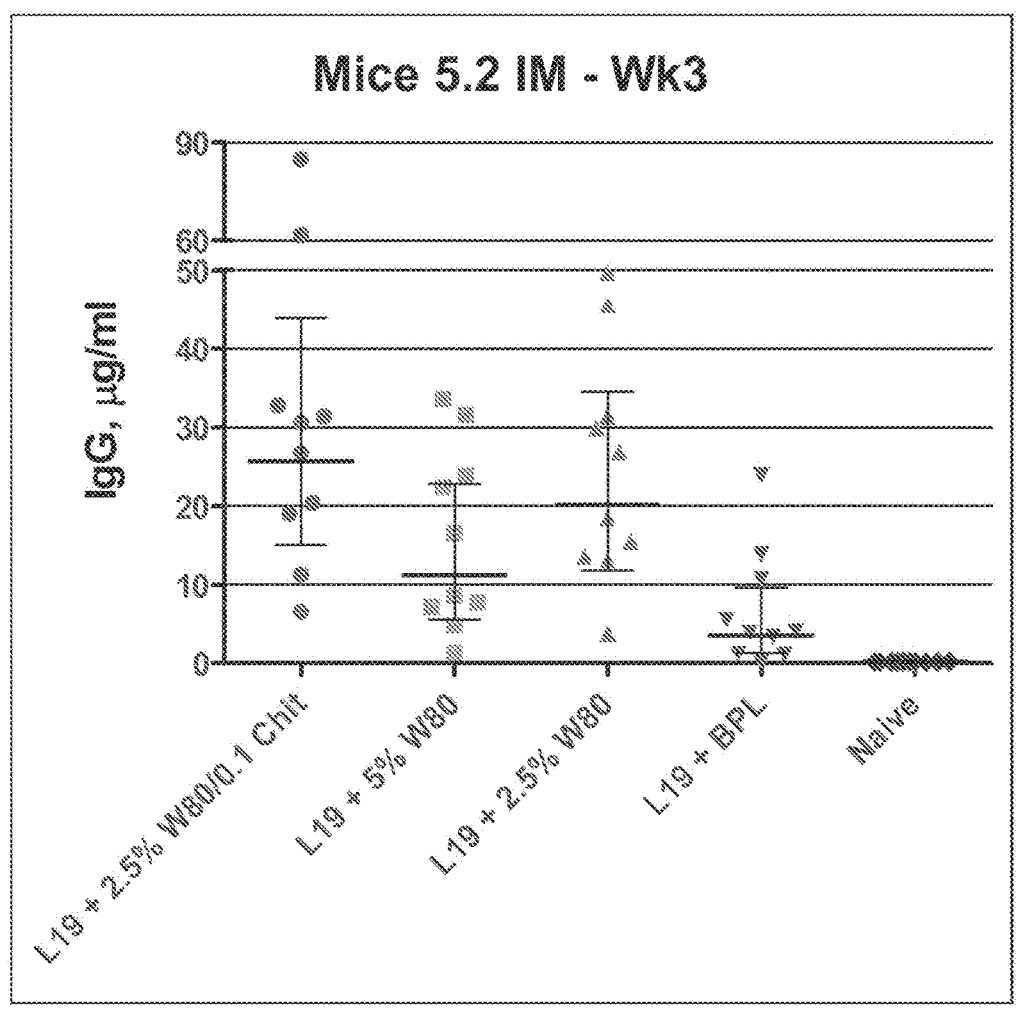
FIG. 17: Shows the immune response (IgG, µg/ml) at week 3 following vaccination in mice vaccinated IM with different nanoemulsion formulations with and without chitosan: (1) RSV strain L19+2.5% $W_{80}5EC+0.1\%$ Low Mol. Wt. Chitosan; (2) RSV strain L19+5% $W_{80}5EC$; (3) RSV strain L19+2.5% $W_{80}5EC$; (4) RSV strain L19+βPL inactivated virus; and (5) naive mice (no vaccine).
Figure 18:
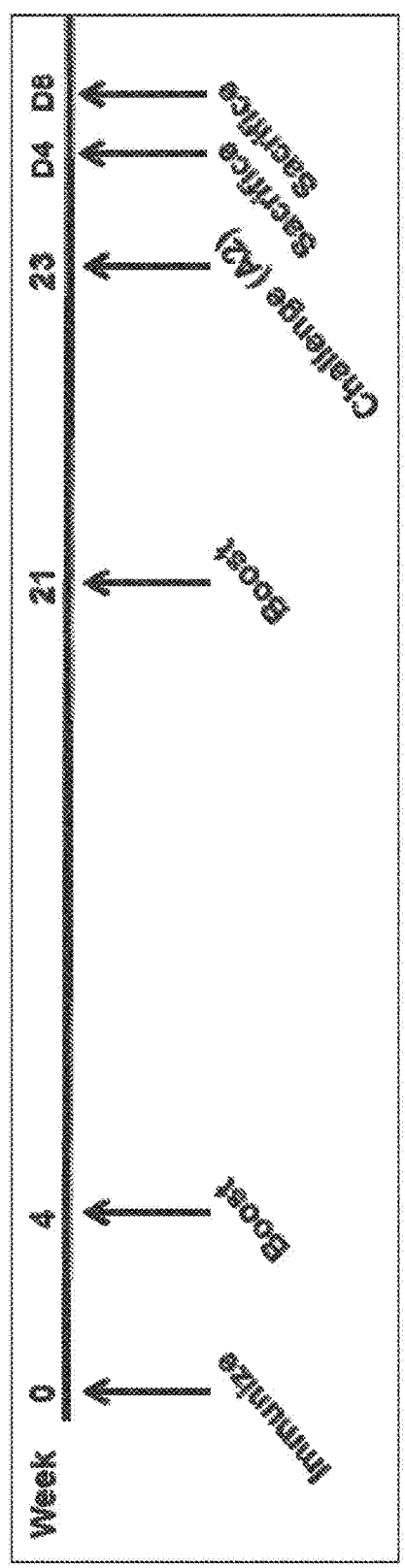
FIG. 18: Shows a vaccination schedule for an evaluation of two nanoemulsion-adjuvanted vaccines in cotton rats (Example 13). The two formulations evaluated include the $W_{80}5EC$ and the $W_{80}P_{188}5EC$ (1:1:5) (see Tables 5 and 6 below). Cotton rats received two doses of 30 µl IN of the nanoemulsion-adjuvanted vaccine containing 6.6 µg F-ptn. They were challenged with $5\times10^5$ pfu RSV strain A2 at week 23. Half of the animals were sacrificed at day 4 and half were sacrificed on day 8.
Figure 19:
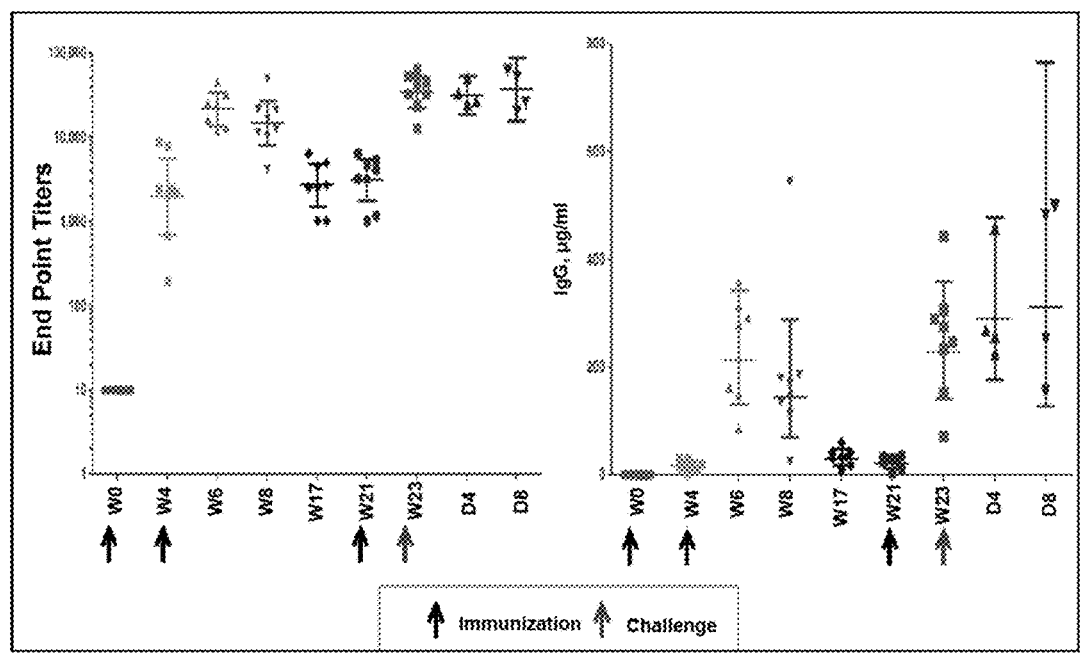
FIG. 19: shows the results of an immunogenicity study of $W_{80}P1885EC$ nanoemulsion inactivated RSV vaccine in cotton rats. In the left panel, the Y axis shows the end point titers of specific antibody to F protein and the X axis shows the time period in weeks. In the right panel the Y-axis shows the serum antibody levels in µg/ml and the X-axis shows the time period in weeks. D4 and D8 show the antibody level in the sera after the challenge.
Figure 20:
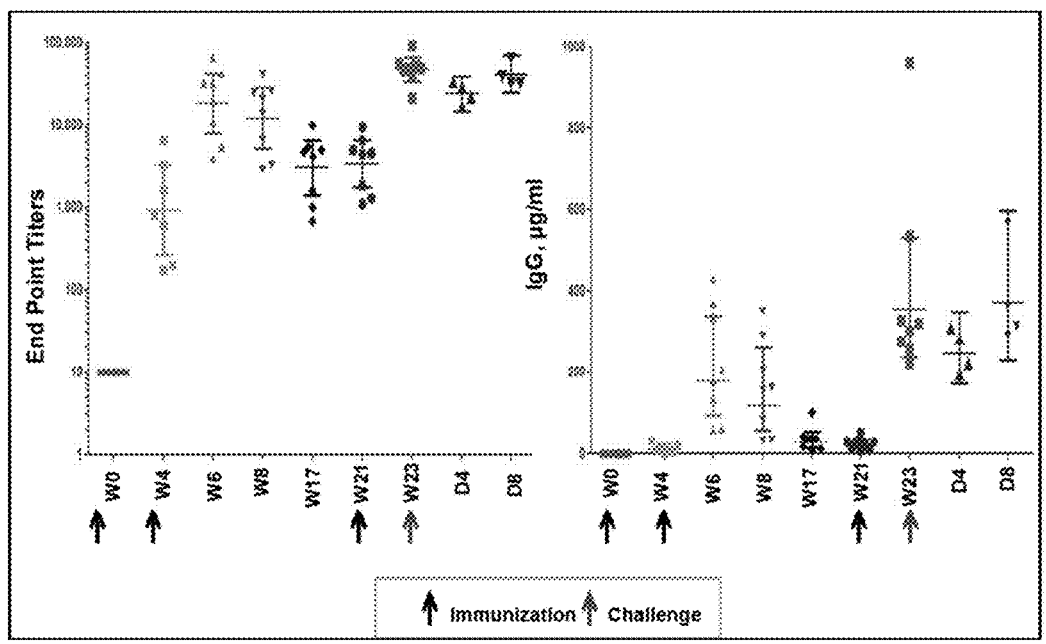
FIG. 20: Shows the results of an immunogenicity study of $W_{80}5EC$ nanoemulsion inactivated RSV vaccine in cotton rats. The Y axis shows the end point titers of specific antibody to F protein and the X axis shows the time period in weeks.

Inactivation with 20% nanoemulsion was performed for 2 hours at room temperature and with 0.25% βPL for 16 hours at 4° C. followed by 2 hours at 37° C. The treated virus was passaged three times in Hep-2 cells and Western blot analysis was performed on cell lysate to determine presence of live virus. See FIG. 15. In particular, FIG. 15 shows the viral inactivation by Western blot assessment, with lanes containing: (1) $W_{80}5EC$ (Lane 1), (2) $W_{80}5EC+0.03\%$ B 1,3 Glucan (lane 2), (3) $W_{80}5EC+0.3\%$ Chitosan (medium molecular weight)+acetic acid (lane 3), (4) $W_{80}5EC+0.3\%$ P407 (lane 4), (5) $W_{80}5EC+0.3\%$ Chitosan (low molecular weight)+0.1% acetic acid (lane 5), (6) media alone (lane 6); (7) βPL-inactivated virus (lane 7), and (8) L19 positive control (lane 8).

RSV L19 was completely inactivated by the nanoemulsion formulations evaluated and by βPL. FIG. 15 shows that three consecutive passages of the NE-treated virus in a cell culture resulted in no detected viral antigen when blotted against RSV antibodies in a western blot. This three cell culture passage test is well established and accepted method for determining viral inactivation. Of note, all lanes in FIG. 15 have a thick background band, which is not a viral band, but is bovine serum albumin. Viral proteins can be detected only in the positive control (lane 8).

Example 11

The purpose of this example was to evaluate the short term stability of RSV vaccines.

Target doses of RSV L19 viral preparations were formulated to achieve a final nanoemulsion concentration of 20%. Vaccine was stored at room temperature (RT) and at 4° C. Stability test parameters included physical and chemical analysis (Table 16).

TABLE 16

Stability Test Parameters

| Stability Test | Acceptance Criteria |
|---|---|
| Physical Appearance | No separation |
| Mean Particle Size | ±10% of initial size |
| Zeta Potential | ±10% of initial charge |
| Western Blot | No change in G band intensity |

Physical appearance, mean particle size, zeta potential and Western Blot acceptance criteria with RSV strain L19 were met following 14 days of storage (longest tested) at RT and 4° C. with $W_{80}5EC+/-\beta PL$ inactivation. $W_{80}5EC+3\%$ P407, $W_{80}5EC+0.3\%$ Chitosan-LMW, and $W_{80}5EC+0.3\%$ Chitosan-MMW were tested for a maximum of 7-8 days and also demonstrated stability. The $W_{80}5EC/P188$ (1:1:5) and $W_{80}5EC/P188$ (1:5:1) formulations were also tested with a live virus RSV A2 strain as opposed to RSV L19 strain for a maximum of 14 days; the 1:1:5 formulation demonstrated stability whereas the 1:5:1 formulation demonstrated potential agglomeration (Table 17).

TABLE 17

Vaccine Stability by Physical and Chemical Parameters and Western Blot

| Viral Strain | Starting Adjuvant Composition (60%) | Condition | Z-average (nm) | # of peaks | PDI | Zeta Potential (mV) | Stability Based on G Protein pass/fail |
|---|---|---|---|---|---|---|---|
| βPL inactivated L19 | Reference | Fresh | 542.1 | 2 | 0.199 | 41.5 | NA |
| | $W_{80}5EC$ (1:6) | 4° C.-14 d | 548.6 | 2 | 0.241 | 43.5 | Pass |
| | | RT-14 d | 538.6 | 2 | 0.210 | 40.7 | Pass |
| L19 | Reference | Fresh | 588.5 | 2 | 0.234 | 39.3 | NA |
| | $W_{80}5EC$ (1:6) | 4° C.-14 d | 545.9 | 2 | 0.210 | 39.9 | Pass |
| | | RT-14 d | 535.6 | 2 | 0.234 | 41.1 | Pass |
| L19 + PEG | $W_{80}5EC$ + 3% P407 (external addition) | Fresh | 779.3 | 1 | 0.351 | 20.2 | NA |
| | | 4° C.-8 d | 654.8 | 1 | 0.313 | 30.4 | Pass |
| | | RT-8 d | 763.2 | 1 | 0.313 | 30.2 | Pass |
| L19 + PEG | $W_{80}5EC$ + 0.3% Chitosan-LMW External Addition | Fresh | 557.2 | 1 | 0.253 | 60.1 | NA |
| | | 4° C.-7 d | 534.7 | 1 | 0.234 | NA | Pass |
| | | RT-7 d | 534.7 | 1 | 0.229 | 62.4 | Pass |
| L19 + PEG | $W_{80}5EC$ + 0.3% Chitosan-MMW | Fresh | 528.4 | 1 | 0.226 | NA | NA |
| | | 4 C.-7 d | 532.0 | 1 | 0.229 | 63.5 | Pass |

TABLE 17-continued

Vaccine Stability by Physical and Chemical Parameters and Western Blot

| Viral Strain | Starting Adjuvant Composition (60%) | Condition | Z-average (nm) | # of peaks | PDI | Zeta Potential (mV) | Stability Based on G Protein pass/fail |
|---|---|---|---|---|---|---|---|
| | External Addition | RT-7 d | 568.0 | 1 | 0.254 | 64.9 | Pass |
| A2 | $W_{80}5EC/P188$ (1:1:5) | Fresh | 229.5 | 1 | 0.108 | 27.0 | NA |
| | | 4° C.-14 d | 259.0 | 2 | 0.206 | 27.0 | Pass |
| | | RT-14 d | 249.9 | 2 | 0.161 | 20.4 | Pass |
| A2 | $W_{80}5EC/P188$ (1:5:1) | Fresh | 396.1 | 2 | 0.164 | 37.1 | NA |
| | | 4° C.-14 d | 5544.0* | 2 | 0.619 | −4.3* | Pass |
| | | RT-14 d | 2010.0* | 2 | 0.753 | −17.1* | Pass |

*potential agglomeration

FIG. 16 shows an example of G bend Intensity of RSV strain L19 with $W_{80}$5EC+/−βPL inactivation by Western blot at day 0 (FIG. 16A) and following 14 days of storage at RT or 4° C. (FIG. 16B). In particular, FIG. 16 shows a Western blot analysis performed with anti-RSV antibody (anti-G); L19 virus $4\times10^6$ PFU/lane, $2\times10^6$ PFU/lane, and $1\times10^6$ PFU/lane+/−βPL inactivation combined with $W_{80}$5EC as indicated. Specimens were analyzed fresh (FIG. 16A) or after 14 days at 4° C. or room temperature (RT) (FIG. 16B).

Example 12

The purpose of this example was to evaluate the immunogenicity of an RSV vaccine in mice.

Mice were immunized intramuscularly as shown in Table 18. Mice received 50 µl of RSV adjuvanted vaccine IM at 0 weeks. Mice were bled on 0 and 3 weeks and tested for serum antibodies. Chitosan was used as an immune-modulator to enhance the immune response in addition to the adjuvant activity contributed to the nanoemulsion.

TABLE 18

| Different arms used in vaccination of the mice | | | |
|---|---|---|---|
| Arm # | Virus Preparation | NE formulation | # of animals |
| 1 | RSV L19 - 2 µg F | 2.5% $W_{80}$5EC + 0.1% Low Mol. Wt. Chitosan | 10 |
| 2 | RSV L19 - 2 µg F | 5% $W_{80}$5EC | 10 |
| 3 | RSV L19 - 2 µg F | 2.5% $W_{80}$5EC | 10 |
| 4 | RSV L19 - 2 µg F βPL inactivated | None | 10 |
| 5 | Naive - No vaccine | | 10 |

Mice vaccinated with nanoemulsion containing chitosan showed more enhanced immune response following a single dose of nanoemulsion adjuvanted RSV vaccine when compared to nanoemulsion without chitosan (FIG. 17). In particular, FIG. 17 shows the immune response (IgG, µg/ml) at week 3 following vaccination in mice vaccinated IM with different nanoemulsion formulations with and without chitosan: (1) RSV strain L19+2.5% $W_{80}$5EC+0.1% Low Mol. Wt. Chitosan; (2) RSV strain L19+5% $W_{80}$5EC; (3) RSV strain L19+2.5% $W_{80}$5EC; (4) RSV strain L19+βPL inactivated virus; and (5) naive mice (no vaccine). The results depicted in FIG. 17 show the highest levels of IgG were found in mice vaccinated with RSV strain L19+2.5% $W_{80}$5EC+0.1% Low Mol. Wt. Chitosan, with the next highest levels of IgG found in mice vaccinated with RSV strain L19+2.5% $W_{80}$5EC, followed by mice vaccinated with RSV strain L19+5% $W_{80}$5EC. The lowest levels of IgG observed in vaccinated mice were for RSV strain L19+βPL inactivated virus.

The strain of RSV identified as RSV strain L19 was deposited under the provisions of the Budapest Treaty at the American Type Culture Collection (ATCC) (Manassas, Va., USA) under accession number PTA-12106 on Sep. 22, 2011.

Example 13

The purpose of this example was to determine the immunogenicity of RSV vaccines according to the invention in Cotton rats.

Cotton rats are the accepted animal species for evaluating immunogenicity and efficacy of RSV vaccines. Using data generated in mice, two nanoemulsions were selected for evaluation in Cotton rats. The two initial formulations studied include the $W_{80}$5EC and the $W_{80}P_{188}$5EC (1:1:5) (see Tables 5 and 6 above).

Cotton rats received two doses of 30 µl IN of the nanoemulsion-adjuvanted vaccine containing 6.6 µg F-ptn. They were challenged with $5\times10^5$ pfu RSV strain A2 at week 23. Half of the animals were sacrificed at day 4 and half were sacrificed on day 8. The vaccination schedule is demonstrated in FIG. 18.

Immunogenicity data presented below show that upon IN immunization with an RSV-nanoemulsion vaccine, a positive immune response was observed. Upon the administration of the second dose, a rapid and significant increase in antibody titers were achieved. Data presented in FIG. 19 show that at week 21, the antibody level in all animals was about one tenth of the maximal values obtained shortly after the administration of the first boost at week 4. Administration of a second boost prior to the challenge yielded an Immune response that was almost identical to levels achieved at week 6, two weeks after the first boost. Both nanoemulsions were equally efficient in eliciting a strong and significant immune responses (FIGS. 19 and 20). (The Y axis in FIGS. 19 and 20 shows the end point titers or antibody quantity of specific antibody to F protein and the X axis shows the time period in weeks.)

ELISA Unit/µg/ml: The amount of specific antibody to F protein was calculated by area under the curve in the ELISA in relation to a defined reference serum which was assigned an arbitrary 100 EU.

Example 14

The purpose of this example was to determine the effect of RSV vaccines according to the Invention on neutralizing antibodies, as well as cross-reactivity of an RSV vaccine comprising RSV strain L19 against other RSV strains following IN administration.

Cotton rats were vaccinated with 30 µl of vaccine intranasally, boosted at 4 weeks, and bled at 0, 4, 6, and 8 weeks. Animals were challenged at week 23 with $5\times10^5$ pfu of RSV strain A2. Study groups included two groups that received 20% $W_{80}5EC$ nanoemulsion mixed with either $1.6\times10^5$ PFU RSV strain L19 containing 3.3 µg F protein (n=8) or $3.2\times10^5$ PFU RSV strain L19 containing 6.6 µg F protein (n=8), as well as two groups that received 20% $W_{80}P_{188}5EC$ nanoemulsion mixed with either $1.6\times10^5$ PFU RSV strain L19 containing 3.3 µg F protein (n=8) or $3.2\times10^5$ PFU L19 RSV containing 6.6 µg F protein (n=8).

Figure 21A:
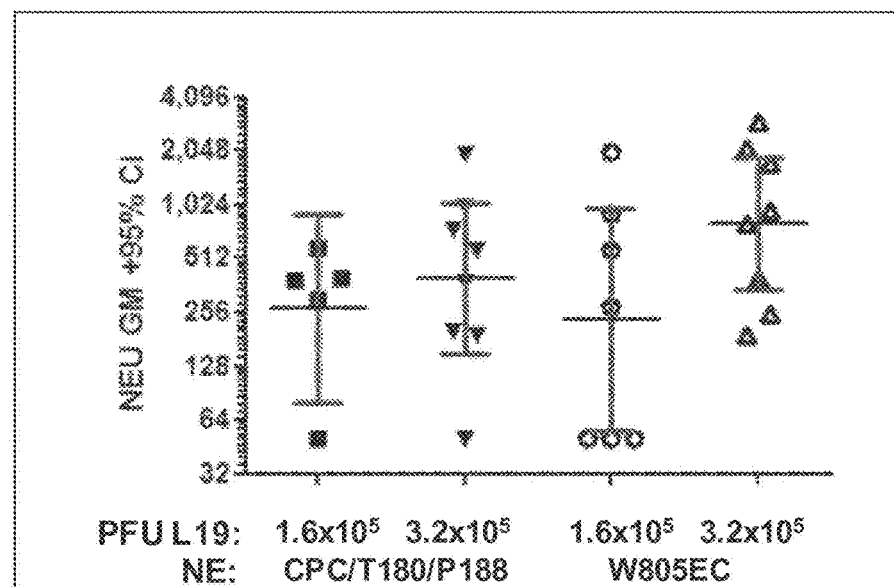
FIGS. 21A-21B: Shows the immunogenicity of RSV neutralization in cotton rats. Cotton rats were vaccinated with 30 µl of vaccine intranasally, boosted at 4 weeks, and bled at weeks 0, 4, 6, and 8. Study groups included two groups that received 20% $W_{80}5EC$ nanoemulsion mixed with either $1.6\times10^5$ PFU RSV strain L19 containing 3.3 µg F protein (n=8) or $3.2\times10^5$ PFU RSV strain L19 containing 6.6 µg F protein (n=8), as well as two groups that received 20% $W_{80}P_{188}5EC$ nanoemulsion mixed with either $1.6\times10^5$ PFU RSV strain L19 containing 3.3 µg F protein (n=8) or $3.2\times10^5$ PFU RSV strain L19 containing 6.6 µg F protein (n=8). Neutralization units (NEU) represent a reciprocal of the highest dilution that resulted in 50% plaque reduction. NEU measurements were performed at 4 weeks (pre boost) and at 6 weeks (2 weeks post boost). Specimens obtained at 6 weeks generated humoral immune responses adequate to allow for NEU analysis. Data is presented as geometric mean with 95% confidence interval (CI) (FIG. 21A). Correlation between EU and NEU is for all animals at 6 weeks using Spearman rho (FIG. 21B).
Figure 21B:
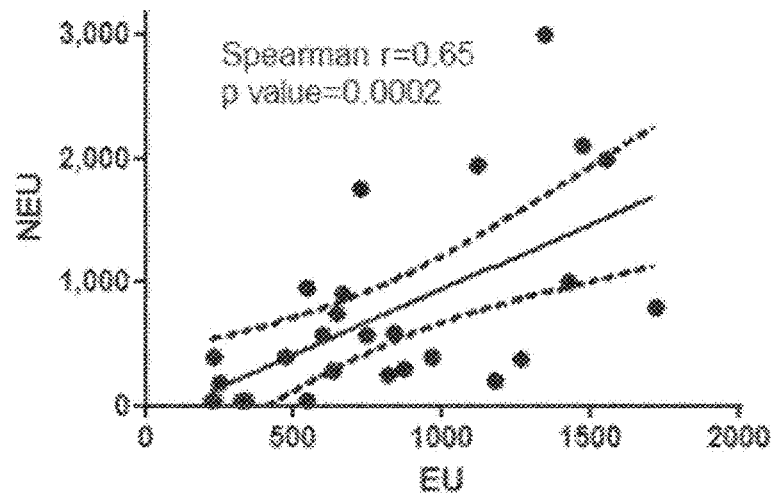

Half of the animals were sacrificed at Day 4 and half at Day 8. Individual cotton rats sera was tested for neutralizing antibodies. Neutralization units (NEU) represent a reciprocal of the highest dilution that resulted in 50% plaque reduction. NEU measurements were performed at 4 weeks (pre boost) and at 6 weeks (2 weeks post boost). Specimens obtained at 6 weeks generated humoral immune responses adequate to allow for NEU analysis. Data is presented as geometric mean with 95% confidence interval (CI) (FIG. 21A). Correlation between EU and NEU is for all animals at 6 weeks using Spearman rho (FIG. 21B).

Specifically, FIG. 21 shows neutralizing antibody titers at 6 weeks time point (FIG. 21A). It is noteworthy that all animals vaccinated with $3.2\times10^a$ PFU RSV as strain L19 inactivated with 60% $W_{80}5EC$ or 60% $W_{80}P_{188}5EC$ generated robust neutralizing antibodies. There is a statistically significant positive correlation between EU and neutralizing antibodies (NEU) (FIG. 218).

Neutralization Unit (NU): The reciprocal of the highest serum dilution that reduces viral plaques by 50%.

Figures 22A, 22B:
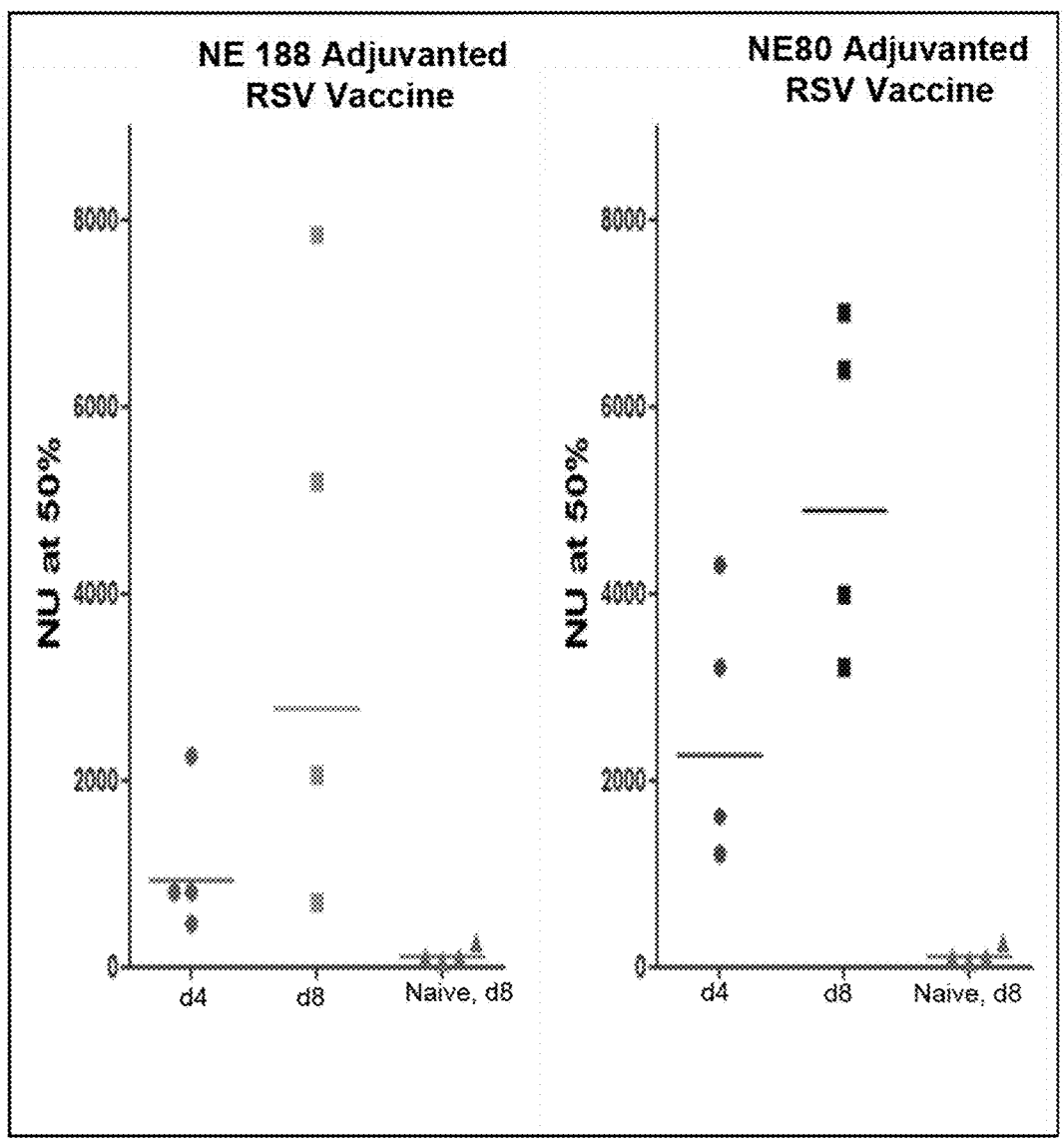
FIGS. 22A-22B: Shows neutralizing antibodies on day 4 and day 8.

Specific activity (NU/EU): Viral neutralizing antibody antibodies (NU) per the one EU F-protein antibody (FIG. 21B) FIG. 22 shows neutralizing antibodies on day 4 and day 8. FIG. 22A shows the results for $W_{80}P_{188}5EC$ nanoemulsion combined with RSV strain L19, and FIG. 22B shows the results for $W_{80}5EC$ nanoemulsion combined with RSV strain L19. All cotton rats demonstrated high neutralizing antibodies (NU) against the vaccine RSV strain L19. Neutralizing antibodies were rising steadily following the challenge (Y axis). Day 8 neutralizing units (NU) were higher than Day 4 NU. Naïve Cotton Rats did not show any neutralization activity in their sera. Serum neutralizing antibodies and specific activity showed a trend to increase from Day 4 to Day 8 post-challenge.

FIG. 23 shows the specific activity of serum antibodies. The specific activity (Neutralizing units/ELISA units) of the serum antibodies tends to increase on Day 8 when compared to Day 4 post-challenge. FIG. 23A shows the results for $W_{80}P_{188}5EC$ nanoemulsion combined with RSV strain L19 (NU/EU for the Y axis), at Day 4 and Day 8. FIG. 23B shows the results for $W_{80}5EC$ nanoemulsion combined with RSV strain L19 (NU/EU for the Y axis), at Day 4 and Day 8. All cotton rats demonstrated high neutralization activity (FIG. 23).

Figure 24A:
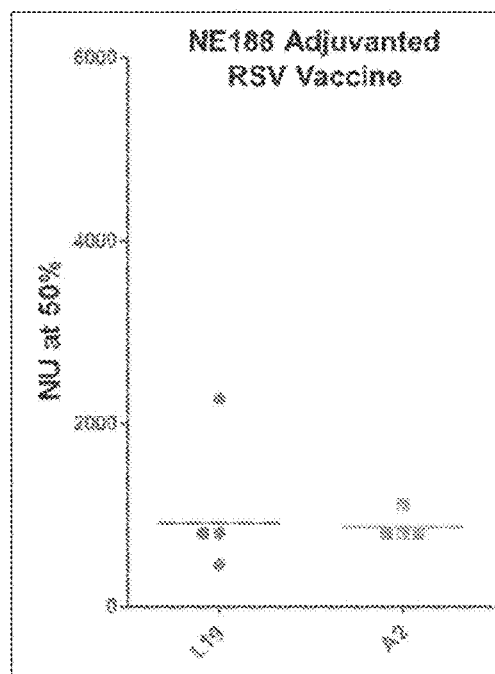
FIGS. 24A-24B: Shows cross protection at Day 4 for cotton rats that received 3 doses of RSV L19 adjuvanted vaccine, then challenged with RSV strain A2.
Figure 24B:
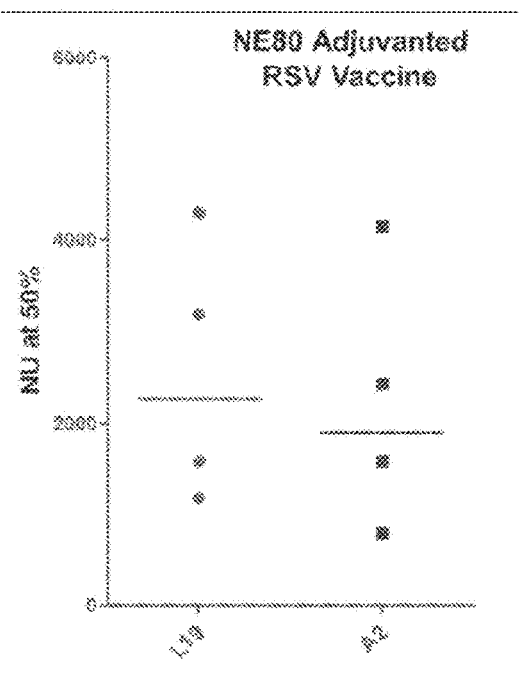
Figure 25:
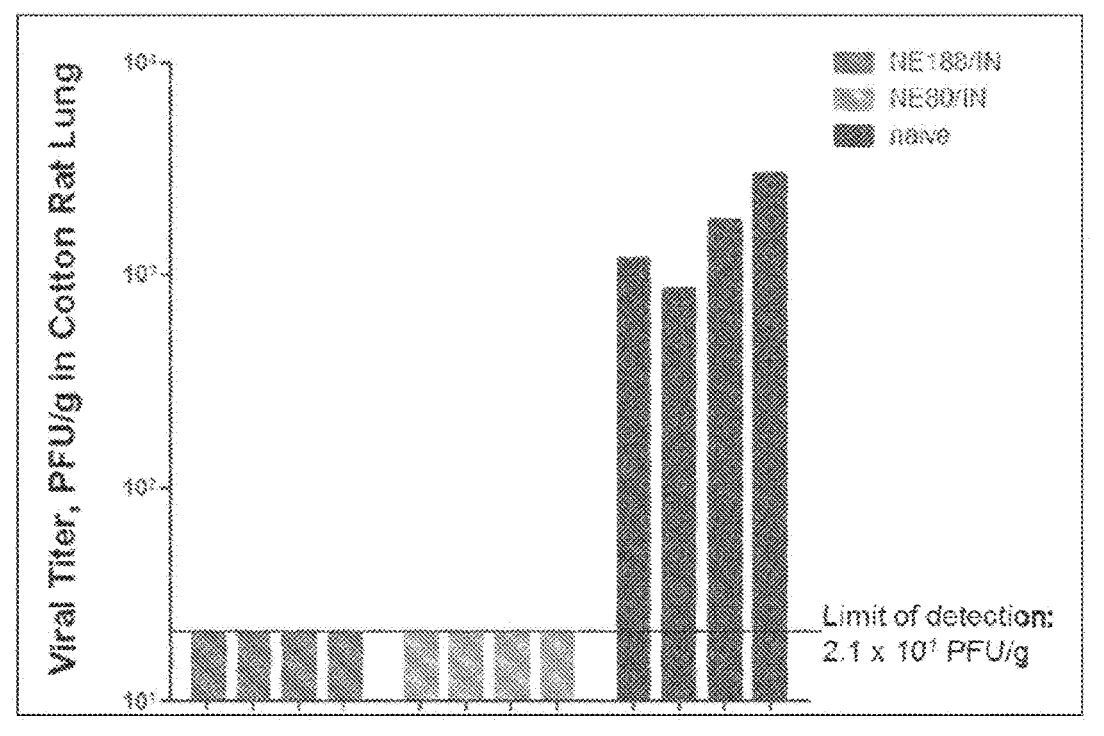

Serum of vaccinated cotton rats showed cross protection against RSV strain A2 (in addition to RSV strain L19) on Day 4 post-challenge (FIG. 24). Specifically, FIG. 24 shows cross protection at Day 4 for cotton rats that received 3 doses of RSV L19 adjuvanted vaccine, then challenged with RSV strain A2. FIG. 24A shows the results for $W_{80}P_{188}5EC$ nanoemulsion combined with RSV strain L19, and FIG. 24B shows the results for $W_{80}5EC$ nanoemulsion combined with RSV strain L19. Serum neutralization activity shows equivalent NU against RSV strain L19 or RSV strain A2, demonstrating cross protection between the two RSV strains. Vaccinated cotton rats cleared all challenged RSV virus on Day 4 post challenge when compared with naïve cotton rats (FIG. 25). As expected by day 8 all animals had cleared the virus. Specifically, FIG. 25 shows viral clearance at Day 4 in the lungs of the cotton rats, by measurement of the RSV strain A2 viral titer (PFU/g) in the lungs of the tested cotton rats. Vaccinated cotton rats (vaccinated with $W_{80}P_{188}5EC$ nanoemulsion combined with RSV strain L19, and $W_{80}5EC$ nanoemulsion combined with RSV strain L19), showed complete clearance of RSV strain A2 challenged virus from the lungs of the cotton rats. In contrast, naïve so animals shows $>10^3$ pfu RSV strain A2/gram of lung (limit of detection was $2.1\times10^1$ pfu/g).

Example 15

The purpose of this example was to evaluate Intramuscular vaccination of RSV vaccines according to the invention in Cotton Rats.

Figure 26:
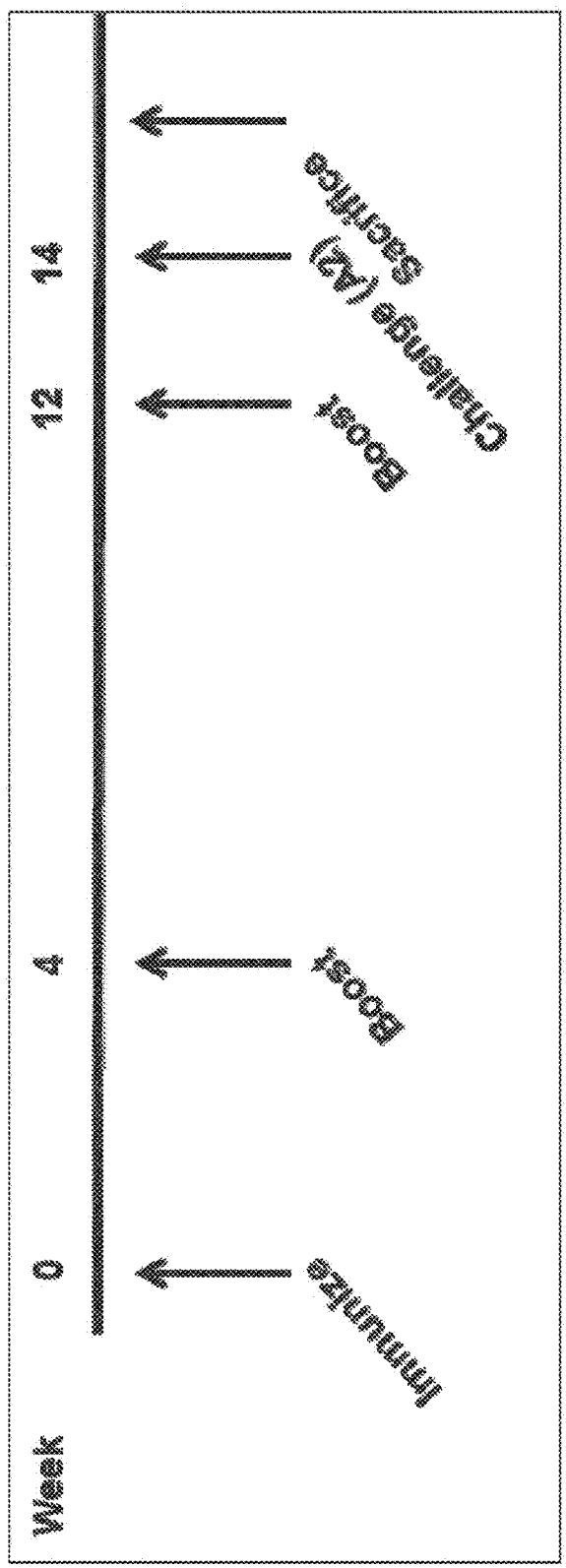
FIG. 26: Shows IM Cotton rat vaccination and challenge schedule.
Figure 27:
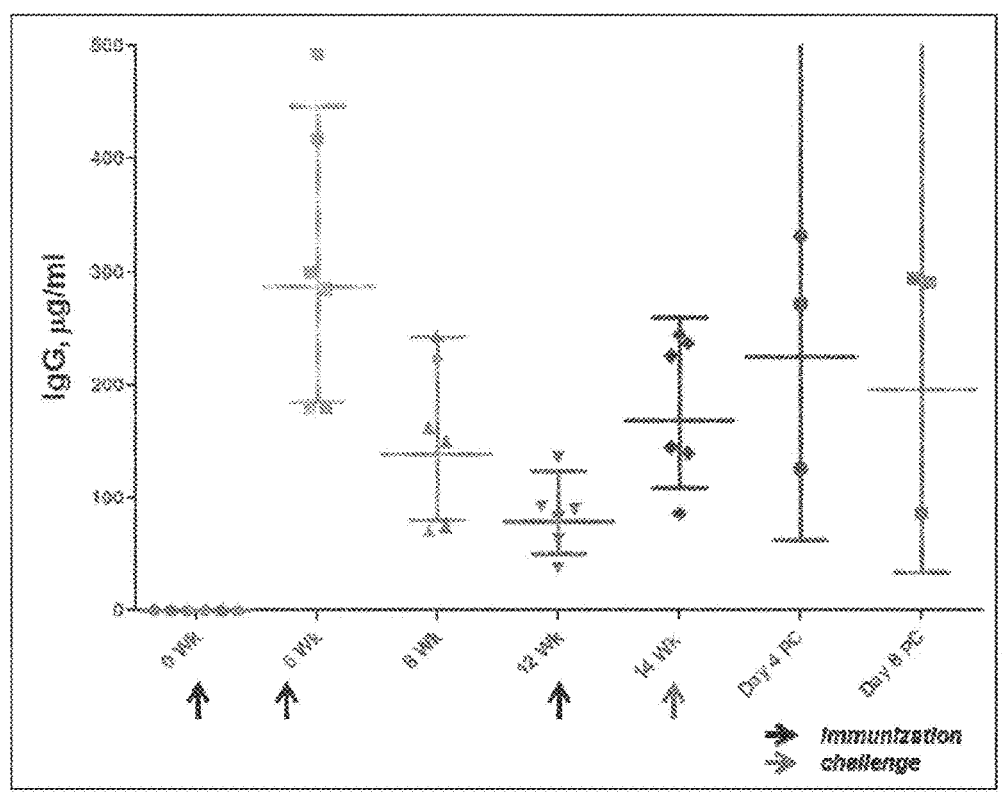
FIG. 27: Shows Serum immune response in cotton rats vaccinated IM with 20% W$_{80}$5EC nanoemulsion mixed with 1.6×10$^5$ PFU RSV strain L19 containing 3.3 µg F protein. The Y axis shows serum IgG, µg/mL, over a 14 week period, at day 4 post-challenge, and at day 8 post-challenge.
Figure 28:
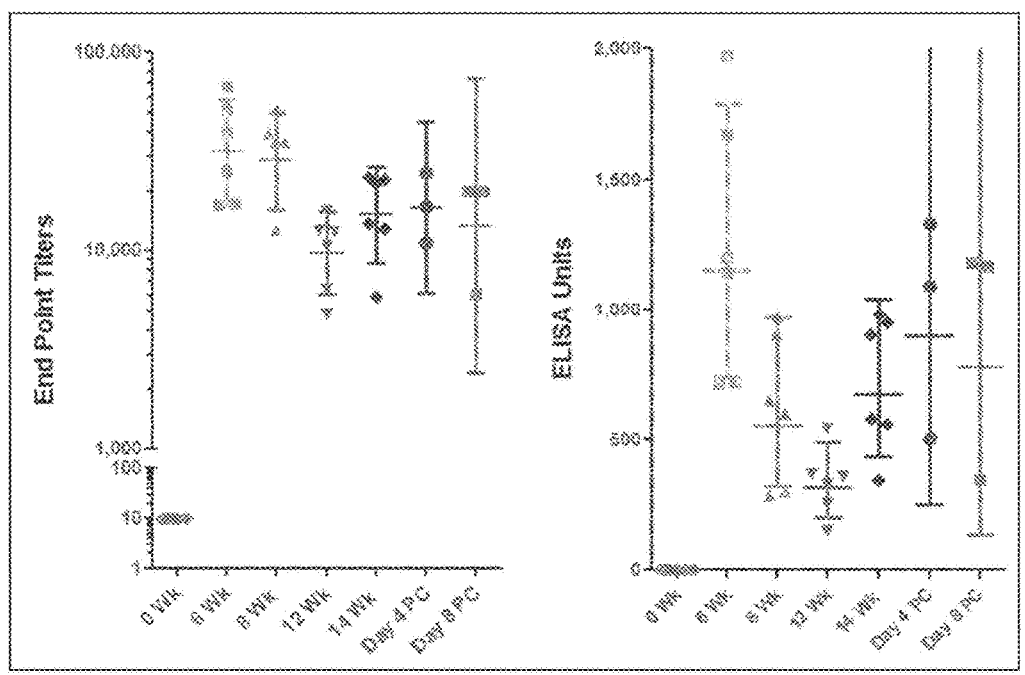
FIGS. 28A-28B: Shows Serum immune response in cotton rats vaccinated IM with 20% W$_{80}$5EC nanoemulsion mixed with 1.6×10$^5$ PFU RSV strain L19 containing 3.3 µg F protein.

Cotton rats were vaccinated IM according to the schedule shown in FIG. 26. Animals received 50 µl RSV adjuvanted RSV vaccine containing 3.3 µg F-protein (20% $W_{80}5EC$ nanoemulsion mixed with $1.6\times10^5$ PFU RSV strain L19 containing 3.3 µg F protein). Cotton rats produced a specific Immune response against RSV. The antibody levels were diminished until a second boost was administered on week 14. There was a slight increase in the antibody levels following the challenge (FIGS. 27 and 28). In particular, FIG. 27 shows the serum immune response in the vaccinated cotton rats. The Y axis shows IgG, µg/mL, over a 14 week period, at day 4 post-challenge, and at day 8 post-challenge. FIG. 28 shows the serum immune response in the vaccinated cotton rats. FIG. 28A shows the end point titers (Y axis) over a 14 week period, at day 4 post-challenge, and at day 8 post-challenge. FIG. 28B shows the ELISA units (Y axis) over a 14 week period, at day 4 post-challenge, and at day 8 post-challenge.

The efficacy of IM immunization was assessed by challenging the animals with a live A2 strain of RSV, which is a strain that causes disease in humans. A dose of $5\times10^5$ pfu of RSV strain A2 was administered to animals two weeks after booster immunization of the RSV L19 nanoemulsion-adjuvanted vaccine. A naïve age-matched group was also challenged. Half of the animals in each group were sacrificed on day 4 post challenge, at which time the maximum viral load was demonstrated in the lungs of Cotton Rats. The other half were sacrificed at day 8.

Figure 29:
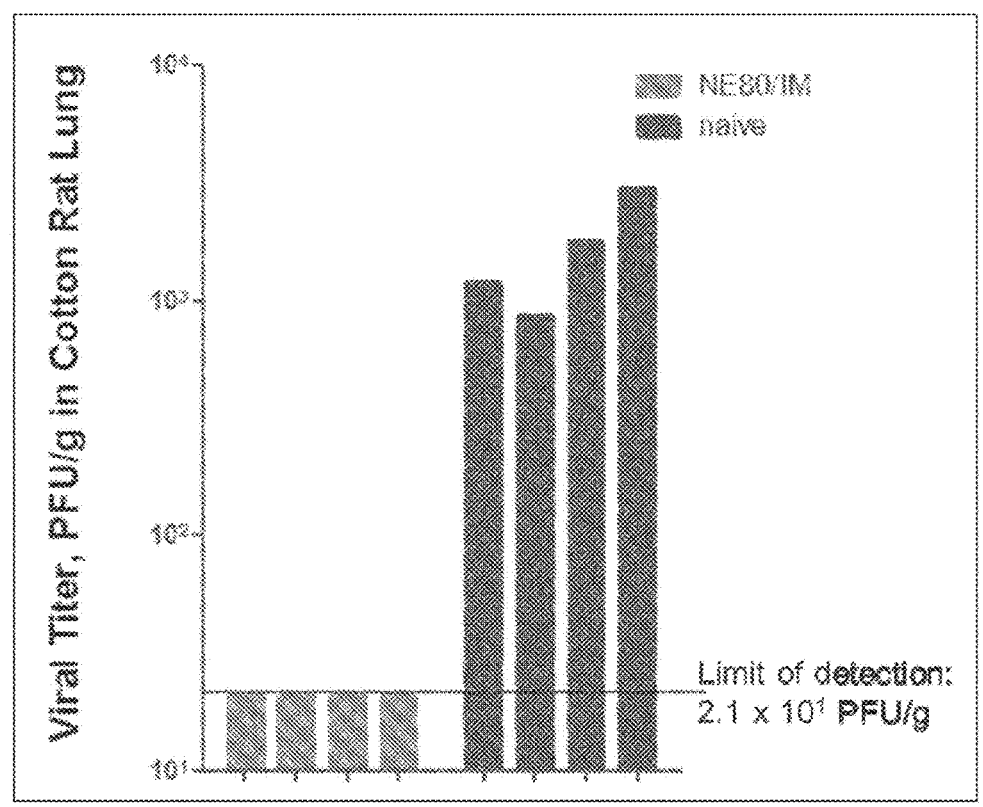
FIG. 29: Shows IM vaccinated cotton rats showed complete clearance of the RSV 4 days following the challenge compared to Naïve animals. Shows viral clearance (RSV strain A2) at Day 4 in lungs of Cotton Rats. IM vaccinated cotton rats (vaccinated with W$_{80}$5EC nanoemulsion combined with RSV strain L19) showed complete clearance of RSV strain A2 challenged virus from the lungs of cotton rats. Naïve animals were showing 10$^3$ pfu RSV strain A2 or greater/gram of lung.

Viral clearance: Lung culture showed that all vaccinated animals had no virus in their lungs at 4 days post challenge while naïve animals had virus loads of $10^3$ pfu RSV strain A2/g of lung tissue (FIG. 21). Specifically, FIG. 29 shows viral clearance at Day 4 In the lungs of the cotton rats, by measurement of the RSV strain A2 viral titer (PFU/g) in the lungs of the tested cotton rats. Vaccinated cotton rats (vaccinated with $W_{80}5EC$ nanoemulsion combined with RSV strain L19), showed complete clearance of RSV strain A2 challenged virus from the lungs of the cotton rats. In contrast, naïve animals showed viral loads of $10^3$ pfu RSV strain A2/gram of lung or greater (limit of detection was $2.1\times10^1$ pfu/g).

Cotton Rat Summary: All RSV vaccines formulated in nanoemulsion and administered IN or IM elicited a protective immune response that prevented infection of immunized animals. Moreover, nanoemulsIon-inactIvated and adjuvanted RSV L19 vaccines are highly immunogenic in the universally accepted cotton rat model. Cotton rats elicited a rise in antibody titers after one Immunization and a significant boost after the second immunization (approximately a 10-fold Increase). The antibodies generated are highly effective in neutralizing live virus and there is a linear relationship between neutralization and antibody titers. Furthermore, antibodies generated in cotton rats showed cross protection when immunized with the RSV L19 strain and challenged with the RSV A2 strain. Both IM and IN immunization established memory that can be invoked or recalled after an exposure to antigen either as a second boost or exposure to live virus.

Example 16

The purpose of this example was to compare intranasal (IN) versus intramuscular (IM) administration of a $W_{80}5EC$ nanoemulsion adjuvanted RSV vaccine.

Figure 30:
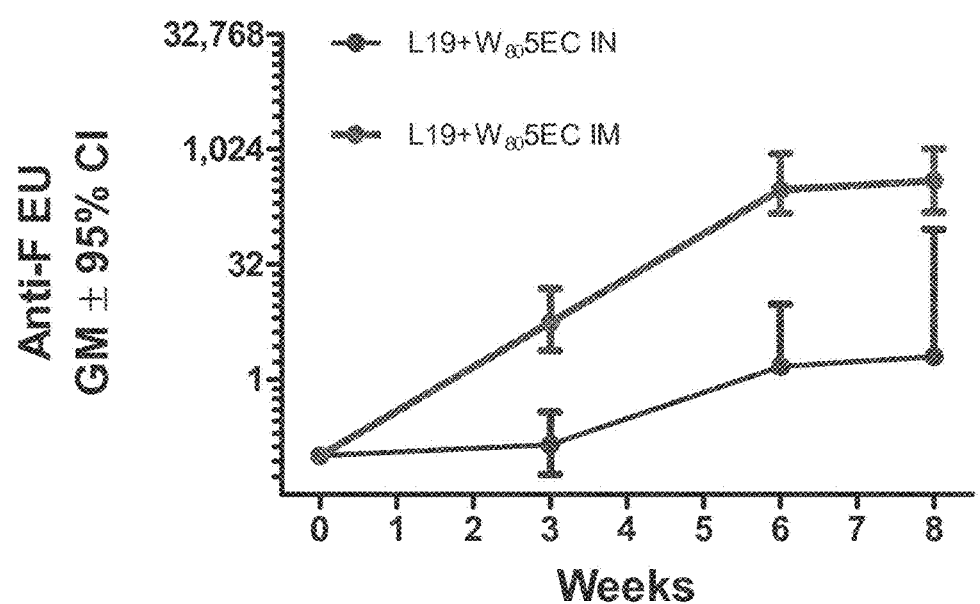
FIG. 30: Shows the measurement of anti-F antibodies (Y axis) over an 8 week period (X axis) for mice vaccinated either IM or IN with RSV vaccine containing 2×10$^5$ plaque forming units (PFU) of L19 RSV virus with 1.7 µg of F protein inactivated with 20% W$_{80}$5EC nanoemulsion adjuvant. BALB/C mice (n=10/arm) were vaccinated at weeks 0 and 4 IN or IM. Serum was analyzed for anti-F antibodies.
Figure 31:
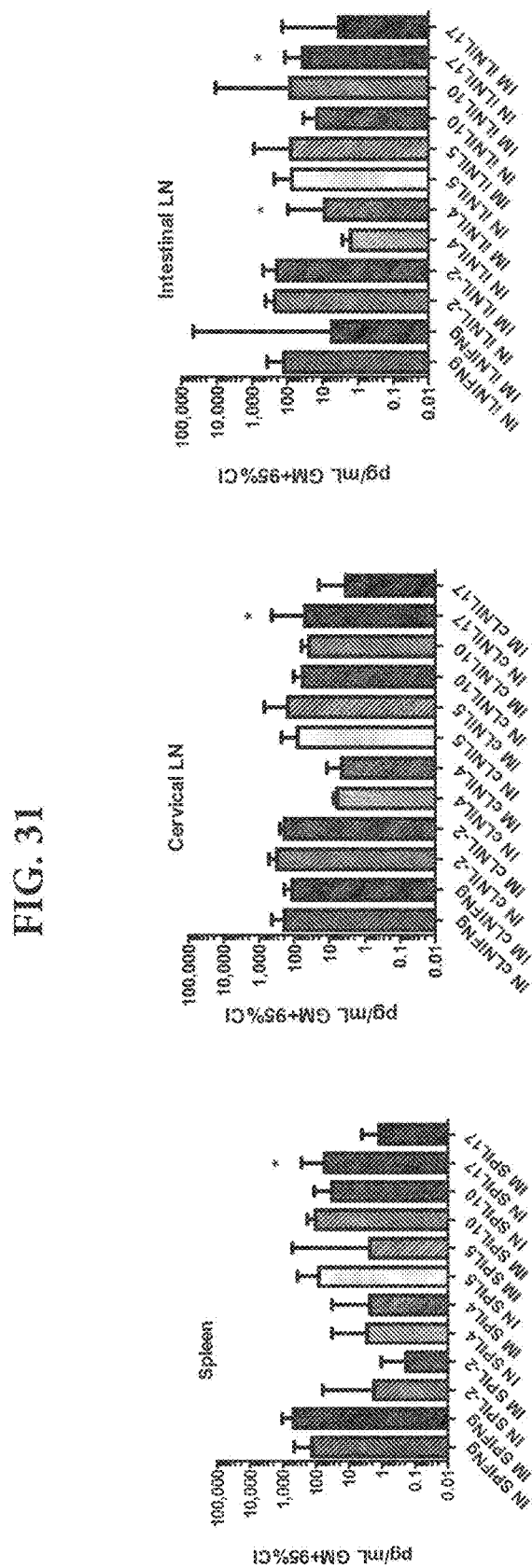
FIG. 31: Shows the measurement of RSV-specific cytokines. Cytokines were measured in cells from spleens, cervical and intestinal lymph nodes (LN) following vaccination of BALB/C mice (n=10/arm) at weeks 0 and 4 IN or IM with RSV vaccine containing 2×10$^5$ plaque forming units (PFU) of L19 RSV virus with 1.7 µg of F protein inactivated with 20% W$_{80}$5EC nanoemulsion adjuvant. Cytokines measured included IFNg, IL-2, IL-4, IL-5, IL-10, and IL-17.

Methods: RSV vaccine containing $2 \times 10^5$ plaque forming units (PFU) of L19 RSV virus with 1.7 µg of F protein was Inactivated with 20% $W_{80}5EC$ nanoemulsion adjuvant. BALB/C mice (n=10/arm) were vaccinated at weeks 0 and 4 IN or IM. Serum was analyzed for anti-F antibodies (FIG. 30). Cells from spleens, cervical and intestinal lymph nodes (LN) were analyzed for RSV-specific cytokines (FIG. 31). Mice were challenged oropharyngeally with $5 \times 10^5$ PFU L19 at 8 weeks. Airway hyperreactivity was assessed by plethysmography. Lungs were analyzed day 8 post challenge to assess mRNA of cytokines, viral proteins, and histopathology.

Figure 32:
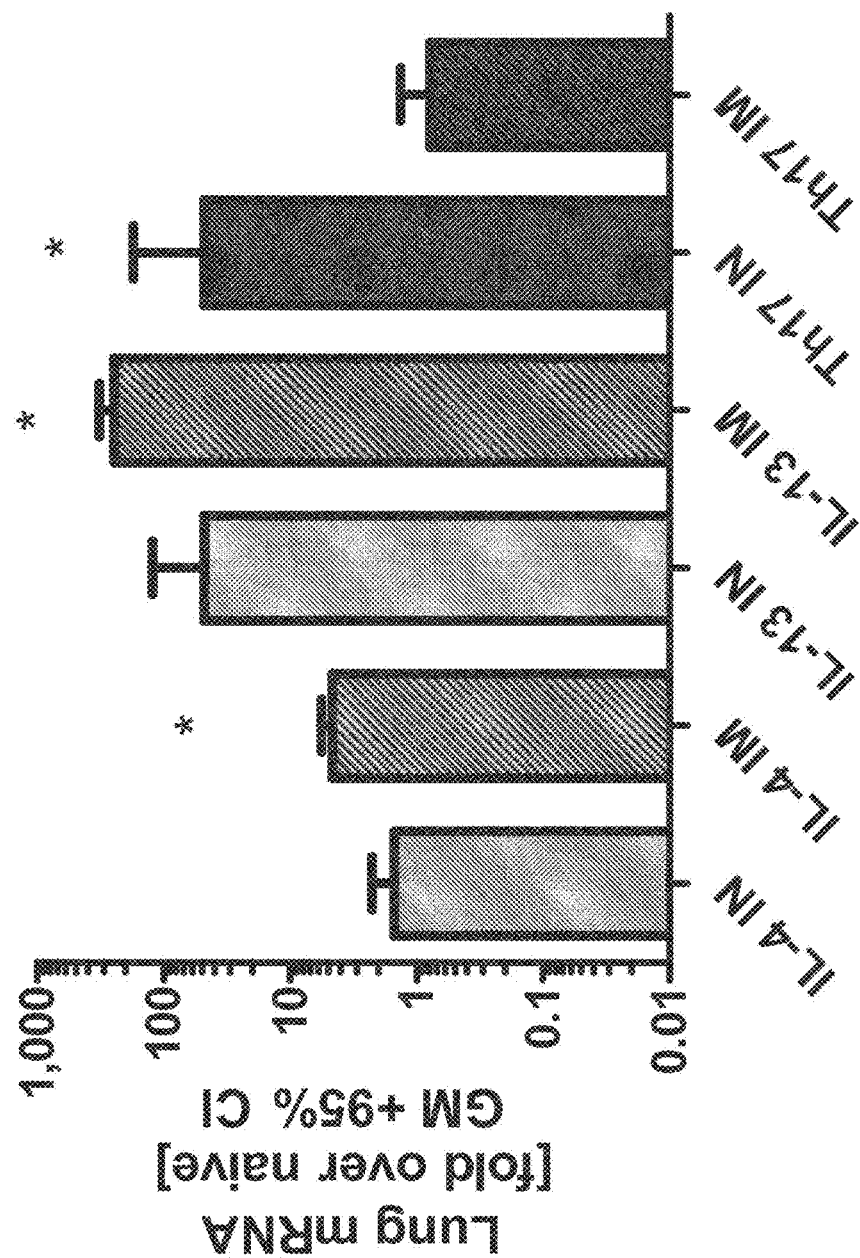
FIG. 32: Shows measurement of the cytokines IL-4, IL-13, and IL-17 in lung tissue following either IN or IM vaccination of BALB/C mice (n=10/arm) at weeks 0 and 4 IN or IM with RSV vaccine containing 2×10$^5$ plaque forming units (PFU) of L19 RSV virus with 1.7 µg of F protein inactivated with 20% W$_{80}$5EC nanoemulsion adjuvant. IL-4 and IL-13 showing greater expression following IM administration, with IL-17 showing greater expression following IN administration.
Figure 33:
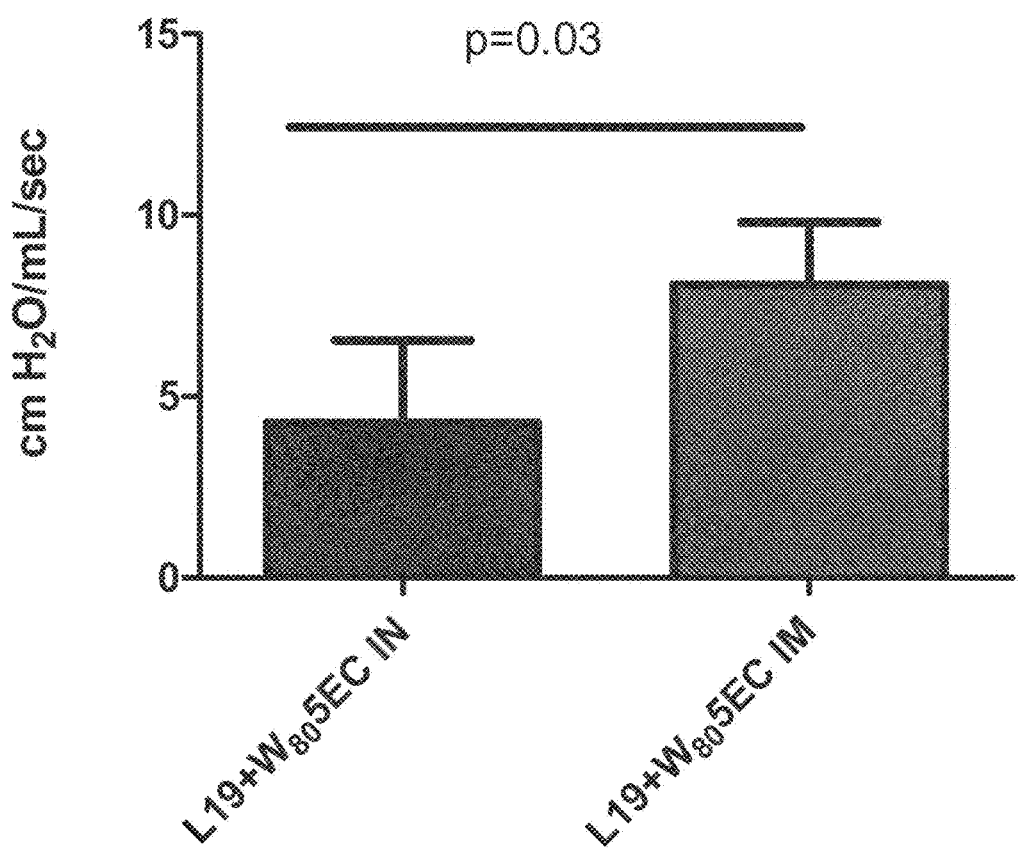
FIG. 33: Shows the measurement of airway resistance (cm H$_2$O/mL/sec) in mice following either IN or IM vaccination of BALB/C mice (n=10/arm) at weeks 0 and 4 IN or IM with RSV vaccine containing 2×10$^5$ plaque forming units (PFU) of L19 RSV virus with 1.7 µg of F protein.

Results: Mice vaccinated IM had higher anti-F antibodies (GM 396 [95% CI 240-652] vs. 2 [95% CI 0-91]) (FIG. 22) and generated more IL-4 and IL-13, after challenge (p<0.05) compared to mice vaccinated IN (FIG. 31). In contrast, IL-17 from spleen cells, cervical LN and Intestinal LN was higher after IN vs IM vaccination (GM: 57 vs 1, 119 vs 3 and 51 vs 4 µg/mL, respectively, p<0.05) (FIG. 31). FIG. 32 shows measurement of the cytokines IL-4, IL-13, and IL-17 In lung tissue following either IN or IM vaccination. IL-4 and IL-13 were expressed at higher so amounts following IM administration, with IL-17 showing greater expression following IN administration. Upon challenge, both routes of immunization resulted in clearance of F and G proteins, but airway resistance was higher in the IM group (p=0.03) with confirmatory histopathology (FIG. 33). Pulmonary IL-4 and IL-13 had a strong positive correlation (r=0.89; p=0.001 and r=0.8; p=0.007, respectively) with airway hyperreactivity. Pulmonary IL-17 was only generated in mice vaccinated IN (p=0.008) and had a strong negative correlation (r=0.81 p=0.007) with airway hyperreactivity.

Conclusion: Compared to IM vaccination, IN vaccination with a novel nanoemulsion adjuvant $W_{80}5EC$ resulted in less airway hyperreactivity, strongly correlated with high IL-17 production. IL-17 as generated by mucosal vaccination may be an important marker for reduced airway hyperreactivity in RSV infection.

FULL CITATIONS FOR DOCUMENTS REFERRED IN THE SPECIFICATION

1. Becker, Y. 2006. Respiratory syncytial virus (RSV) evades the human adaptive immunity system by skewing the Th1/Th2 cytokine balance toward Increased levels of Th2 cytokines and IgE, markers of allergy—a review. Virus Genes. 33:235-252.
2. Bielinska, A, Gerber M. Blanco L, et al. Induction of Th17 cellular immunity with a novel nanoemulsion adjuvant. 2010. Crit Rev Immunol. 30:189-199.
3. Boyoglu, S, Komal, V, et al. 2009. Enhanced delivery and expression of a nanoencapsulated DNA vaccine vector for respiratory syncytial virus. 5:463-472.
4. Castilow, E, Olson M, et al. 2007. Understanding respiratory syncytial (RSV) vaccine-enhanced disease. Immunol Res. 39:225-239.
5. Conti H R, Shen F, et al., Th17 and IL-17 receptor signaling are essential for mucosal host defenses against oral candidiasis. J Exp Med. 2009. 206:299-311.
6. Cyr, S, Jones, T et al. 2007. Intranasal proteosome-based respiratory syncytial virus (RSV) vaccine protect BALB/c mice against challenge without eosinophilia or enhanced pathology. Vaccine. 25:5378-5389.
7. DeLyrica E, Raymond W R, et al., Vaccination of mice with *H. pylori* induces a strong Th-17 response and immunity that is neutrophil dependent. Gastroent. 2009. 136:247-256.
8. Fu, Y, He, J, et al. 2009. Intranasal immunization with a replication-deficient adenoviral vector expressing the fusion glycoprotein of respiratory syncytial virus elicits protective Immunity in BALB/c mice. Biochem & Biophys Res Comm. 381:528-532.
9. Gomez, M., Mufson, M. at al. 2009. Phase-I study MEDI-534, of a live attenuated intranasal vaccine against respiratory syncytial virus and parainfluenza-3 virus in seropositive children. Ped Infect J. 28: 655-658.
10. Graham, B. 2011. Biological challenges and technological opportunities for respiratory syncytial virus vaccine development. Immunological Reviews. 239: 149-166.
11. Hacking, D., Hull, J. 2002. Respiratory syncytial virus—virus biology and host response. J. Infection. 45: 18-24.
12. Hamouda T, Chepurnov A, Mank N, et al. Efficacy, immunogenicity and stability of a novel intranasal nanoemulsion adjuvanted influenza vaccine in a murine model. Hum Vaccine. 2010. 6:585-594.
13. Haynes, L, Caldi, H. et al. 2009. Therapeutic monoclonal antibody treatment targeting respiratory syncytial virus (RSV) G protein mediates viral clearance and reduces pathogenesis of RSV infection in BALB/c mice. J Infect Dis. 200:439-447.
14. Huang K., Lawlor, H. 2010. Recombinant respiratory syncytial virus F protein expression is hindered by inefficient nuclear export and mRNA processing. Virus Genes. 40: 212-221.
15. Johnson, T, and Graham, B. 2004. Contribution of respiratory syncytial virus G antigenicity to vaccine-enhanced Illness and the implications for severe disease during primary respiratory syncytial virus infection. Pediatr Infect Dis J. 23:46-57.

16. Johnson, T, Teng, M, et al. 2004. Respiratory syncytial virus (RSV) G glycoprotein is not necessary for vaccine-enhanced disease induced by immunization with formalin-inactivated RSV. J Virol. 78:6024-6032.

17. Kim, S., J Jang., et al., 2010. Single mucosal immunization of recombinant adenovirus-based vaccine expressing F1 protein fragment Induces protective mucosal immunity against respiratory syncytial virus infection. Vaccine. 28: 3801-3808.

18. Kruijens D., Schijf, M. 2011. Local innate and adaptive immune responses regulate inflammatory cell Influx into the lungs after vaccination with formalin inactivated RSV. Vaccine. 29: 2730-2741.

19. Langley, J., Sales V., et al. 2009. A dose ranging study of a subunit Respiratory Syncytial Virus subtype A vaccine with and without aluminum phosphate adjuvantation in adults≥65 years of age. Vaccine. 27: 5913-5919.

20. Lindell D, Morris S, White M, et al. A novel inactivated intranasal respiratory syncytial virus vaccine promotes viral clearance without Th2 associated vaccine-enhanced disease. PLoS One. 2011. 7:e21823.

21. Lukacs, N, Smit J, et al. 2010. Respiratory virus-induced TLR7 activation controls IL-17-associated increased mucus via IL-23 regulation. J Immunol. 185:2231-2239.

22. Makidon, P, Bielinska, A, Nigavekar, S, et al. Preclinical evaluation of a novel nanoemulsion-based hepatitis B mucosal vaccine. PLOS-One. 2008. 3:e2954.

23. McLellan, J., Y Yang. at al., 2011. Structure of the Respiratory Syncytial Virus Fusion glycoprotein in the post-fusion conformation reveals preservation of neutralizing epitopes. J Virology. Epub. 1128/JVI00555-11.

24. Munir, S, Hillyer, P, et al. 2011. Respiratory syncytial virus interferon antagonist NS1 protein suppresses and skews the human T lymphocyte response. PLoS Pathog 7(4): e1001336. Doi:10.1371/journal.ppat.1001.6.

25. Nallet, S., Amacker, M. at al. 2009. Respiratory Syncytial Virus subunit vaccine based on a recombinant fusion protein expressed transiently in mammalian cells. 27: 6415-6419.

26. Olson, M, Hartwig, S, et al. 2011. The number of respiratory syncytial virus (RSV)-specific memory CD8 T cells in the lung is critical for their ability to inhibit RSV vaccine-enhanced pulmonary eosinophilia. J Immunol. 181: 7958-7968.

27. Olszewska, W, Suezer, Y, et al. 2004. Protective and disease-enhancing immune responses induced by recombinant modified vaccinia Ankara (MVA) expressing respiratory syncytial virus protein. Vaccine. 23:215-221.

28. Radu, G, Caidi, H. et al. 2010. Prophylactic treatment with a G glycoprotein monoclonal antibody reduces inflammation in a respiratory syncytial virus (RSV-G) challenge naïve and formalin-inactivated RSV-immunized BALB/c mice. J Virol. 84:9632-9636.

29. Rixon, H., Brown, C. et al. 2002. Multiple glycosylated forms of the respiratory syncytial virus fusion protein are expressed in virus-infected cells. J Gen Virology. 83: 61-66.

30. Schlender, J., Zimmer, G. 2003. Respiratory Syncytial Virus (RSV) fusion protein subunit F2, not attachment protein G, determines the specificity of RSV infection. J Virology. 77: 4609-4616.

31. Singh, S., Dennis, V. 2007. Immunogenicity and efficacy of recombinant RSV-F vaccine in a mouse model. Vaccine. 125: 6211-6223.

32. Wanson, K., Settembre, E. 2011. Structural basis for immunization with post-fusion respiratory syncytial virus fusion F glycoprotein (RSV F) to elicit high neutralizing antibody titers. PNAS. 108: 9619-9624.

33. Wu, H, Dennis, V, et al. 2009. RSV fusion (F) protein DNA vaccine provides protection against viral Infection. Vaccine. 145:39-47.

We claim:

1. A method for inducing an increased level of acquired immunity against diseases caused by respiratory syncytial viruses (RSV) comprising:
   (a) administering to a subject a first effective amount of a vaccine comprising:
      (i) at least one isolated RSV antigen, wherein the isolated RSV antigen is an isolated RSV F protein, an isolated RSV G protein, an isolated antigenic fragment of RSV F protein, an isolated antigenic fragment of RSV G protein, or any combination thereof;
      (ii) an immune-enhancing nanoemulsion or a dilution thereof, comprising droplets having an average size of about 1000 nm or less, an aqueous phase, at least one oil, at least one surfactant, and at least one organic solvent, wherein the at least one isolated RSV antigen is comprised within the nanoemulsion; and
   (b) administering to the subject a second boost amount of the same vaccine, wherein the level of acquired immunity is increased as compared to a subject that has not been administered the nanoemulsion.

2. The method of claim 1, wherein the second boost amount of the vaccine is administered at 4 weeks following administering the first effective amount of the vaccine.

3. The method of claim 1, wherein the isolated RSV antigen is from a human respiratory syncytial virus HRSV-L19.

4. The method of claim 1, wherein administering the first effective amount of the vaccine and/or administering the second boost amount of the vaccine comprises parenteral, oral or intranasal administration.

5. The method of claim 4, wherein the parenteral administration is by intradermal, subcutaneous, intraperitoneal or intramuscular injection.

6. The method of claim 1, wherein the vaccine further comprises isolated RSV virion particles.

7. The method of claim 6, wherein the RSV virion particles are from a human respiratory syncytial virus HRSV-L19.

8. The method of claim 6, wherein the RSV virion particles are inactivated by the nanoemulsion.

9. The method of claim 1, wherein the subject is an infant.

10. The method of claim 1, wherein the subject is elderly, has chronic obstructive pulmonary disease (COPD), is a transplant patient, or any combination thereof.

11. The method of claim 1, wherein the isolated RSV antigen is present in a fusion protein.

12. The method of claim 1, wherein the isolated RSV antigen is a peptide fragment of RSV F protein, a peptide fragment of RSV G protein, or any combination thereof.

13. The method of claim 1, wherein the isolated RSV antigen is multivalent.

14. The method of claim 13, wherein the multivalent antigen is RSV F protein, RSV G protein, an antigenic fragment of RSV F protein, an antigenic fragment of RSV G protein, or any combination thereof.

15. The method of claim 1, wherein administration of the immune enhancing nanoemulsion to the subject induces a Th1 immune response, a Th2 immune response, a Th17 immune response, or any combination thereof.

16. The method of claim 1, wherein the vaccine composition: (a) is not systemically toxic to the subject; (b) produces minimal or no inflammation upon administration; or (c) any combination thereof.

17. The method of claim 1, wherein the nanoemulsion droplets have an average diameter selected from the group consisting less than about 1000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, greater than about 50 nm, greater than about 70 nm, greater than about 125 nm, greater than about 125 nm and less than about 600 nm, and any combination thereof.

18. The method of claim 1, wherein the nanoemulsion comprises:
   (a) an aqueous phase;
   (b) about 1% oil to about 80% oil;
   (c) about 0.1% organic solvent to about 50% organic solvent; and
   (d) about 0.001% surfactant to about 10% surfactant.

19. The method of claim 18, wherein the surfactant is one or more nonionic surfactants and the nanoemulsion further comprises at least one cationic surfactant.

* * * * *